US012557989B2

(12) United States Patent
Buckley et al.

(10) Patent No.: US 12,557,989 B2
(45) Date of Patent: Feb. 24, 2026

(54) NEUROSURGICAL METHODS AND SYSTEMS FOR DETECTING AND REMOVING TUMOROUS TISSUE

(71) Applicant: Stryker European Operations Limited, Carrigtwohill (IE)

(72) Inventors: Kevin Buckley, Saint Lukes (IE); Gerard Nunan, Ballincollig (IE); Stephen Faul, Rochestown (IE); David Eustace, Carrigrohane (IE); Kevin Manley, Cobh (IE); Robert Mitchell Baldwin, Grand Rapids, MI (US); David Tallon, Shanagarry (IE)

(73) Assignee: Stryker European Operations Limited, Carrigtwohill (IE)

( * ) Notice: Subject to any disclaimer, the term of this patent is extended or adjusted under 35 U.S.C. 154(b) by 24 days.

(21) Appl. No.: 18/281,491

(22) PCT Filed: Mar. 14, 2022

(86) PCT No.: PCT/IB2022/052294
§ 371 (c)(1),
(2) Date: Sep. 11, 2023

(87) PCT Pub. No.: WO2022/190076
PCT Pub. Date: Sep. 15, 2022

(65) Prior Publication Data
US 2024/0148252 A1     May 9, 2024

Related U.S. Application Data

(60) Provisional application No. 63/160,099, filed on Mar. 12, 2021.

(51) Int. Cl.
*A61B 5/00* (2006.01)

(52) U.S. Cl.
CPC .......... *A61B 5/0071* (2013.01); *A61B 5/0084* (2013.01); *A61B 5/4064* (2013.01); *A61B 5/7271* (2013.01); *A61B 2560/04* (2013.01)

(58) Field of Classification Search
None
See application file for complete search history.

(56) References Cited

U.S. PATENT DOCUMENTS 4,375,313 A     3/1983  Anderson et al.
4,436,366 A     3/1984  Abramson
(Continued)

FOREIGN PATENT DOCUMENTS

CN     208808702 U     5/2019
CN     110996816 B     6/2023
(Continued)

OTHER PUBLICATIONS

English language abstract and machine-assisted English translation for KR 101343868 B1 extracted from espacenet.com database on Jan. 3, 2024, 16 pages.

(Continued)

*Primary Examiner* — Katherine L Fernandez
(74) *Attorney, Agent, or Firm* — Howard & Howard Attorneys PLLC

(57)     ABSTRACT

A neurosurgery system for probing brain tissue of a patient for tumorous tissue. The system including a suction tool, an excitation source, an optical instrument, and a controller. The suction tool including a suction cannula defining a lumen, an optical fiber configured to transmit fluorescence emitted by the brain tissue; and an indicator configured to selectively emit visible light. An excitation source is configured to emit an excitation light having a wavelength to induce the fluorescence in the tumorous tissue. The optical instrument is coupled to the optical fiber. The optical instru- (Continued)

ment configured to convert the fluorescence emitted by the brain tissue and transmitted by the optical and configured to determine that the brain tissue is tumorous based on the electrical signal and activate the indicator based on the determination.

23 Claims, 24 Drawing Sheets

(56)                     References Cited

U.S. PATENT DOCUMENTS

| | | | |
|---|---|---|---|
| 4,541,438 | A | 9/1985 | Parker et al. |
| 4,768,513 | A | 9/1988 | Suzuki |
| 4,878,900 | A * | 11/1989 | Sundt ..................... A61M 1/86 |
| | | | 433/91 |
| 4,952,022 | A | 8/1990 | Genovese |
| 5,128,717 | A | 7/1992 | Uchikawa et al. |
| 5,156,142 | A | 10/1992 | Anapliotis et al. |
| 5,200,345 | A | 4/1993 | Young |
| 5,269,777 | A | 12/1993 | Doiron et al. |
| 5,496,997 | A | 3/1996 | Pope |
| 5,569,254 | A | 10/1996 | Carlson et al. |
| 5,633,494 | A | 5/1997 | Danisch |
| 5,749,830 | A | 5/1998 | Kaneko et al. |
| 5,784,162 | A | 7/1998 | Cabib et al. |
| 5,902,246 | A | 5/1999 | McHenry et al. |
| 5,929,901 | A | 7/1999 | Adair et al. |
| 5,954,655 | A | 9/1999 | Hussman |
| 5,964,747 | A | 10/1999 | Eaton et al. |
| 5,986,693 | A | 11/1999 | Adair et al. |
| 5,999,844 | A | 12/1999 | Gombrich et al. |
| 6,043,839 | A | 3/2000 | Adair et al. |
| 6,048,104 | A | 4/2000 | Ohkubo et al. |
| 6,081,740 | A | 6/2000 | Gombrich et al. |
| 6,086,528 | A | 7/2000 | Adair |
| 6,129,683 | A | 10/2000 | Sutton et al. |
| D434,376 | S | 11/2000 | Connelly |
| 6,174,291 | B1 | 1/2001 | McMahon et al. |
| 6,189,533 | B1 | 2/2001 | Simon et al. |
| 6,190,877 | B1 | 2/2001 | Adair |
| 6,192,734 | B1 | 2/2001 | Rothfritz et al. |
| 6,211,904 | B1 | 4/2001 | Adair et al. |
| 6,246,901 | B1 | 6/2001 | Benaron |
| 6,270,494 | B1 | 8/2001 | Kovalcheck et al. |
| 6,275,255 | B1 | 8/2001 | Adair et al. |
| 6,289,229 | B1 | 9/2001 | Crowley |
| 6,304,766 | B1 | 10/2001 | Colvin, Jr. |
| 6,310,642 | B1 | 10/2001 | Adair et al. |
| 6,316,215 | B1 | 11/2001 | Adair et al. |
| 6,334,014 | B1 | 12/2001 | Nitta et al. |
| 6,361,490 | B1 | 3/2002 | Irion et al. |
| 6,377,841 | B1 | 4/2002 | Lin et al. |
| 6,393,312 | B1 | 5/2002 | Hoyns |
| 6,416,234 | B1 | 7/2002 | Wach et al. |
| 6,424,369 | B1 | 7/2002 | Adair et al. |
| 6,452,626 | B1 | 9/2002 | Adair et al. |
| 6,461,349 | B1 | 10/2002 | Elbrecht et al. |
| 6,488,414 | B1 | 12/2002 | Dawes et al. |
| 6,497,715 | B2 | 12/2002 | Satou |
| 6,510,338 | B1 | 1/2003 | Irion et al. |
| 6,534,618 | B1 | 3/2003 | Jacobs et al. |
| 6,571,118 | B1 | 5/2003 | Utzinger et al. |
| 6,575,989 | B1 | 6/2003 | Scheller et al. |
| 6,580,941 | B2 | 6/2003 | Webb |
| 6,594,518 | B1 | 7/2003 | Benaron et al. |
| 6,595,696 | B1 | 7/2003 | Zellak |
| 6,640,131 | B1 | 10/2003 | Irion et al. |
| 6,652,836 | B2 | 11/2003 | Luiken |
| 6,654,630 | B2 | 11/2003 | Zuluaga et al. |
| 6,678,398 | B2 | 1/2004 | Wolters et al. |
| 6,697,652 | B2 | 2/2004 | Georgakoudi et al. |
| 6,699,040 | B1 | 3/2004 | Hahn et al. |
| 6,703,621 | B2 | 3/2004 | Wolleschensky |
| 6,741,346 | B1 | 5/2004 | Gerstner et al. |
| 6,748,259 | B1 | 6/2004 | Benaron et al. |
| 6,750,037 | B2 | 6/2004 | Adair et al. |
| 6,753,160 | B2 | 6/2004 | Adair |
| 6,768,918 | B2 | 7/2004 | Zelenchuk |
| 6,806,953 | B2 | 10/2004 | Engelhardt et al. |
| 6,807,876 | B2 | 10/2004 | Beck et al. |
| 6,825,928 | B2 | 11/2004 | Liu et al. |
| 6,839,586 | B2 | 1/2005 | Webb |
| 6,860,879 | B2 | 3/2005 | Irion et al. |
| 6,862,036 | B2 | 3/2005 | Adair et al. |
| 6,863,650 | B1 | 3/2005 | Irion |
| 6,874,925 | B2 | 4/2005 | Page et al. |
| 6,882,785 | B2 | 4/2005 | Eichelberger et al. |
| 6,884,220 | B2 | 4/2005 | Aviv et al. |
| 6,912,412 | B2 | 6/2005 | Georgakoudi et al. |
| 6,955,680 | B2 | 10/2005 | Satou et al. |
| 6,982,740 | B2 | 1/2006 | Adair et al. |
| 6,982,742 | B2 | 1/2006 | Adair et al. |
| 6,984,220 | B2 | 1/2006 | Wuchinich |
| 6,984,498 | B2 | 1/2006 | Adair |
| 7,002,621 | B2 | 2/2006 | Adair et al. |
| 7,009,699 | B2 | 3/2006 | Wolleschensky et al. |
| 7,030,904 | B2 | 4/2006 | Adair et al. |
| 7,067,276 | B2 | 6/2006 | Adair |
| 7,110,808 | B2 | 9/2006 | Adair |
| 7,118,563 | B2 | 10/2006 | Weckwerth et al. |
| 7,119,898 | B2 | 10/2006 | Zimmermann et al. |
| 7,133,130 | B2 | 11/2006 | Storz et al. |
| 7,150,737 | B2 | 12/2006 | Purdy et al. |
| 7,154,602 | B2 | 12/2006 | Wachsmuth |
| 7,163,397 | B2 | 1/2007 | Hahn et al. |
| 7,181,106 | B2 | 2/2007 | Ushiro et al. |
| 7,202,947 | B2 | 4/2007 | Liu et al. |
| 7,223,961 | B2 | 5/2007 | Birk et al. |
| 7,245,696 | B2 | 7/2007 | Yun et al. |
| 7,250,045 | B2 | 7/2007 | Island et al. |
| 7,280,203 | B2 | 10/2007 | Olschewski |
| 7,282,724 | B2 | 10/2007 | Olschewski |
| 7,289,205 | B2 | 10/2007 | Yaroslavsky et al. |
| 7,292,323 | B2 | 11/2007 | Artsyukhovich et al. |
| 7,304,811 | B2 | 12/2007 | Chiang |
| 7,335,223 | B2 | 2/2008 | Obrebski |
| 7,356,225 | B2 | 4/2008 | Loebel |
| 7,369,073 | B2 | 5/2008 | Jess et al. |
| 7,385,176 | B2 | 6/2008 | Pfeiffer et al. |
| 7,402,158 | B2 | 7/2008 | Scheller et al. |
| 7,413,567 | B2 | 8/2008 | Weckwerth et al. |
| 7,427,165 | B2 | 9/2008 | Benaron et al. |
| 7,446,322 | B2 | 11/2008 | Riedmann et al. |
| 7,447,539 | B2 | 11/2008 | Genet et al. |
| 7,452,356 | B2 | 11/2008 | Grove et al. |
| 7,477,764 | B2 | 1/2009 | Haisch |
| 7,490,996 | B2 | 2/2009 | Sommer |
| 7,515,952 | B2 | 4/2009 | Balas et al. |
| 7,515,953 | B2 | 4/2009 | Madar et al. |
| 7,564,550 | B2 | 7/2009 | Yaroslavsky et al. |
| 7,566,173 | B2 | 7/2009 | Auld et al. |
| 7,570,988 | B2 | 8/2009 | Ramanujam et al. |
| 7,598,088 | B2 | 10/2009 | Balas |
| 7,618,177 | B2 | 11/2009 | Cazzini |
| 7,627,363 | B2 | 12/2009 | Yaroslavsky et al. |
| 7,635,330 | B2 | 12/2009 | Kang et al. |
| 7,647,092 | B2 | 1/2010 | Motz et al. |
| 7,649,185 | B2 | 1/2010 | Rice et al. |
| 7,653,429 | B2 | 1/2010 | Madar et al. |
| 7,668,587 | B2 | 2/2010 | Benaron et al. |
| 7,702,381 | B2 | 4/2010 | Gaeta et al. |
| 7,720,532 | B2 | 5/2010 | Hashimshony et al. |
| 7,725,162 | B2 | 5/2010 | Malackowski et al. |
| 7,731,710 | B2 | 6/2010 | Smith |
| 7,748,979 | B2 | 7/2010 | Nahlieli |
| 7,783,346 | B2 | 8/2010 | Smith et al. |
| 7,787,928 | B2 | 8/2010 | Frisch et al. |
| 7,812,945 | B2 | 10/2010 | Fortier et al. |
| 7,824,089 | B2 | 11/2010 | Charles |
| 7,837,372 | B2 | 11/2010 | Hickingbotham |
| 7,904,139 | B2 | 3/2011 | Chance |
| 7,952,718 | B2 | 5/2011 | Li et al. |
| 7,974,683 | B2 | 7/2011 | Balas et al. |

(56) References Cited

U.S. PATENT DOCUMENTS

| | | | |
|---|---|---|---|
| 7,981,111 | B2 | 7/2011 | Grove et al. |
| 8,012,146 | B2 | 9/2011 | Hickingbotham |
| 8,029,727 | B2 | 10/2011 | Hyde et al. |
| 8,029,740 | B2 | 10/2011 | Hyde et al. |
| 8,064,976 | B2 | 11/2011 | Ince |
| 8,114,346 | B2 | 2/2012 | Hyde et al. |
| 8,135,454 | B2 | 3/2012 | Daniels et al. |
| 8,139,211 | B2 | 3/2012 | Yaroslavsky et al. |
| 8,144,958 | B2 | 3/2012 | Nahm et al. |
| 8,147,423 | B2 | 4/2012 | Hashimshony et al. |
| 8,152,798 | B2 | 4/2012 | Smith |
| 8,162,496 | B2 | 4/2012 | Kang et al. |
| 8,162,924 | B2 | 4/2012 | Boyden et al. |
| 8,165,663 | B2 | 4/2012 | Hyde et al. |
| 8,173,432 | B2 | 5/2012 | Balas |
| 8,175,687 | B2 | 5/2012 | Kang et al. |
| 8,177,800 | B2 | 5/2012 | Spitz et al. |
| 8,180,436 | B2 | 5/2012 | Boyden et al. |
| 8,193,517 | B2 | 6/2012 | Ishihara |
| 8,195,282 | B2 | 6/2012 | Hashimshony |
| 8,206,315 | B2 | 6/2012 | Mark et al. |
| 8,207,510 | B2 | 6/2012 | Kempe et al. |
| 8,216,173 | B2 | 7/2012 | Dacey, Jr. et al. |
| 8,229,548 | B2 | 7/2012 | Frangioni |
| 8,265,724 | B2 | 9/2012 | Petersen |
| 8,267,934 | B2 | 9/2012 | Earley et al. |
| 8,277,048 | B2 | 10/2012 | Artsyukhovich et al. |
| 8,282,593 | B2 | 10/2012 | Dacey, Jr. et al. |
| 8,285,366 | B2 | 10/2012 | Hyde et al. |
| 8,285,367 | B2 | 10/2012 | Hyde et al. |
| 8,287,525 | B2 | 10/2012 | Stocks et al. |
| 8,300,310 | B2 | 10/2012 | Knebel |
| 8,306,600 | B2 | 11/2012 | Steffen et al. |
| 8,309,346 | B2 | 11/2012 | Zuckerman |
| 8,310,531 | B2 | 11/2012 | Nandy |
| 8,320,984 | B2 | 11/2012 | Kuhn et al. |
| 8,320,996 | B2 | 11/2012 | Panasyuk et al. |
| 8,343,086 | B2 | 1/2013 | Dacey, Jr. et al. |
| 8,343,434 | B2 | 1/2013 | Hyde et al. |
| 8,361,070 | B2 | 1/2013 | Hanlon et al. |
| 8,366,443 | B2 | 2/2013 | Nahlieli et al. |
| 8,366,652 | B2 | 2/2013 | Dacey, Jr. et al. |
| 8,380,268 | B2 | 2/2013 | Georgakoudi et al. |
| 8,382,812 | B2 | 2/2013 | Kang et al. |
| 8,396,539 | B2 | 3/2013 | Sharma et al. |
| 8,406,836 | B2 | 3/2013 | Kuhn et al. |
| 8,414,517 | B2 | 4/2013 | Dacey, Jr. et al. |
| 8,449,147 | B2 | 5/2013 | Papac et al. |
| 8,452,384 | B2 | 5/2013 | Ince |
| 8,460,229 | B2 | 6/2013 | Dacey, Jr. et al. |
| 8,463,343 | B2 | 6/2013 | Kuhn et al. |
| 8,467,843 | B2 | 6/2013 | Markle et al. |
| 8,480,279 | B2 | 7/2013 | Papac et al. |
| 8,485,972 | B2 | 7/2013 | Papac et al. |
| 8,498,506 | B2 | 7/2013 | Smith et al. |
| 8,542,962 | B2 | 9/2013 | Smith et al. |
| 8,551,104 | B2 | 10/2013 | Weckwerth et al. |
| 8,553,337 | B2 | 10/2013 | Webb et al. |
| 8,585,627 | B2 | 11/2013 | Dacey, Jr. et al. |
| 8,586,946 | B2 | 11/2013 | Beck et al. |
| 8,596,881 | B2 | 12/2013 | Umeno |
| 8,606,350 | B2 | 12/2013 | Ishihara |
| 8,614,851 | B2 | 12/2013 | Kuster |
| 8,620,410 | B2 | 12/2013 | Frangioni |
| 8,647,292 | B2 | 2/2014 | Dacey, Jr. et al. |
| 8,649,836 | B2 | 2/2014 | Shimizu et al. |
| 8,649,849 | B2 | 2/2014 | Liu et al. |
| 8,702,640 | B2 | 4/2014 | Dacey, Jr. et al. |
| 8,705,042 | B2 | 4/2014 | Haisch et al. |
| 8,705,184 | B2 | 4/2014 | Xu et al. |
| 8,706,184 | B2 | 4/2014 | Mohr et al. |
| 8,706,211 | B2 | 4/2014 | Dacey, Jr. et al. |
| 8,709,003 | B2 | 4/2014 | Island et al. |
| 8,734,718 | B2 | 5/2014 | Dacey, Jr. et al. |
| 8,743,362 | B2 | 6/2014 | Gono |
| 8,753,304 | B2 | 6/2014 | Dacey, Jr. et al. |
| 8,764,261 | B2 | 7/2014 | Smith |
| 8,767,059 | B2 | 7/2014 | Endo et al. |
| 8,777,935 | B2 | 7/2014 | Weckwerth et al. |
| 8,803,070 | B2 | 8/2014 | Fujiwara |
| 8,804,115 | B2 | 8/2014 | Yu et al. |
| 8,823,786 | B2 | 9/2014 | Beck et al. |
| 8,864,662 | B2 | 10/2014 | Grey et al. |
| 8,885,034 | B2 | 11/2014 | Adair et al. |
| 8,888,731 | B2 | 11/2014 | Dacey, Jr. et al. |
| 8,900,139 | B2 | 12/2014 | Yadlowsky et al. |
| 8,921,809 | B2 | 12/2014 | Lippert et al. |
| 8,923,955 | B2 | 12/2014 | Thiberville et al. |
| 8,929,973 | B1 | 1/2015 | Webb et al. |
| 8,935,127 | B2 | 1/2015 | Liedtke et al. |
| 8,936,551 | B2 | 1/2015 | Vayser et al. |
| 8,945,195 | B2 | 2/2015 | Oka et al. |
| 8,948,851 | B2 | 2/2015 | Leblond et al. |
| 8,970,688 | B2 | 3/2015 | Kalkbrenner et al. |
| 8,977,085 | B2 | 3/2015 | Walsh et al. |
| 8,983,581 | B2 | 3/2015 | Bawendi et al. |
| 8,988,771 | B2 | 3/2015 | Kleppe et al. |
| 9,002,159 | B2 | 4/2015 | Sutherland et al. |
| 9,005,263 | B2 | 4/2015 | Boyden et al. |
| 9,042,967 | B2 | 5/2015 | Dacosta et al. |
| 9,044,142 | B2 | 6/2015 | Hauger et al. |
| 9,046,448 | B2 | 6/2015 | Takats |
| 9,066,658 | B2 | 6/2015 | Hamel et al. |
| 9,067,059 | B2 | 6/2015 | Bissig et al. |
| 9,072,452 | B2 | 7/2015 | Vayser et al. |
| 9,072,454 | B2 | 7/2015 | Irion et al. |
| 9,091,823 | B2 | 7/2015 | Shen et al. |
| 9,107,730 | B2 | 8/2015 | Huculak et al. |
| 9,131,861 | B2 | 9/2015 | Ince et al. |
| 9,134,243 | B2 | 9/2015 | Wilson et al. |
| 9,149,648 | B2 | 10/2015 | Dacey, Jr. et al. |
| 9,151,907 | B2 | 10/2015 | Jiang et al. |
| 9,179,845 | B2 | 11/2015 | Farcy et al. |
| 9,186,052 | B1 | 11/2015 | Adair et al. |
| 9,186,067 | B1 | 11/2015 | Tearney et al. |
| 9,198,565 | B2 | 12/2015 | Adair et al. |
| 9,216,015 | B2 | 12/2015 | Wilson |
| 9,226,731 | B2 | 1/2016 | Liu et al. |
| 9,226,979 | B2 | 1/2016 | Hashimshony |
| 9,229,165 | B2 | 1/2016 | Vayser et al. |
| 9,241,636 | B2 | 1/2016 | Koizumi et al. |
| 9,271,710 | B2 | 3/2016 | Grey et al. |
| 9,282,985 | B2 | 3/2016 | Finkman et al. |
| 9,295,392 | B2 | 3/2016 | Douplik et al. |
| 9,297,992 | B2 | 3/2016 | Ganser et al. |
| 9,301,686 | B2 | 4/2016 | Montcuquet |
| 9,301,771 | B2 | 4/2016 | Auclair, Jr. et al. |
| 9,307,895 | B2 | 4/2016 | Adair et al. |
| 9,326,666 | B2 | 5/2016 | Frangioni |
| 9,332,893 | B2 | 5/2016 | Saadat et al. |
| 9,336,592 | B2 | 5/2016 | Fan et al. |
| 9,348,127 | B2 | 5/2016 | Kempe et al. |
| 9,364,213 | B2 | 6/2016 | Speziali |
| 9,364,982 | B2 | 6/2016 | Schaller |
| 9,370,447 | B2 | 6/2016 | Mansour |
| 9,372,334 | B2 | 6/2016 | Seyfried |
| 9,377,405 | B2 | 6/2016 | Möhler et al. |
| 9,402,643 | B2 | 8/2016 | Auld et al. |
| 9,411,113 | B2 | 8/2016 | Neuberger |
| 9,429,713 | B2 | 8/2016 | Thornton, Jr. |
| 9,451,882 | B2 | 9/2016 | Nie et al. |
| 9,451,885 | B2 | 9/2016 | Liu |
| 9,456,200 | B2 | 9/2016 | Ji et al. |
| 9,474,831 | B2 | 10/2016 | Boyden et al. |
| 9,476,766 | B2 | 10/2016 | Widzgowski |
| 9,498,136 | B2 | 11/2016 | Lucassen et al. |
| 9,528,938 | B2 | 12/2016 | Wang |
| 9,539,438 | B2 | 1/2017 | Pan et al. |
| 9,550,072 | B2 | 1/2017 | Trujillo et al. |
| 9,561,085 | B2 | 2/2017 | Yadlowsky et al. |
| 9,597,154 | B2 | 3/2017 | Simon et al. |
| 9,630,532 | B2 | 4/2017 | Schnell et al. |
| 9,651,765 | B2 | 5/2017 | Schreiber |
| 9,667,896 | B2 | 5/2017 | Adair et al. |

(56) References Cited

U.S. PATENT DOCUMENTS

| | | | |
|---|---|---|---|
| 9,675,235 B2 | 6/2017 | Lieponis | |
| 9,687,670 B2 | 6/2017 | Dacey, Jr. et al. | |
| 9,693,720 B2 | 7/2017 | Markle et al. | |
| 9,727,962 B2 | 8/2017 | Hauger et al. | |
| 9,730,576 B2 | 8/2017 | Yadlowsky et al. | |
| 9,743,836 B2 | 8/2017 | Tsubouchi et al. | |
| 9,757,147 B2 | 9/2017 | Mark et al. | |
| 9,763,744 B2 * | 9/2017 | Wilson | A61B 10/0275 |
| 9,772,224 B2 | 9/2017 | Ishiguro et al. | |
| 9,775,522 B2 | 10/2017 | Van Keersop et al. | |
| 9,788,728 B2 | 10/2017 | Perelman | |
| 9,820,655 B2 | 11/2017 | Ramanujam et al. | |
| 9,883,804 B2 | 2/2018 | Wilzbach | |
| 9,883,854 B2 | 2/2018 | Mak | |
| 9,913,752 B2 | 3/2018 | Hauger | |
| 9,931,039 B2 | 4/2018 | Huang et al. | |
| 9,952,155 B2 | 4/2018 | Foelling | |
| 9,956,053 B2 | 5/2018 | Diao et al. | |
| 9,958,392 B2 | 5/2018 | Hauger et al. | |
| 9,968,414 B2 | 5/2018 | Wilson | |
| 10,016,248 B2 | 7/2018 | Mirsepassi et al. | |
| 10,022,200 B2 | 7/2018 | Richmond | |
| 10,042,123 B2 | 8/2018 | Rinzler et al. | |
| 10,045,687 B2 | 8/2018 | Henig et al. | |
| 10,054,775 B2 | 8/2018 | Hauger et al. | |
| 10,068,173 B2 | 9/2018 | Vayser et al. | |
| 10,071,180 B1 | 9/2018 | Miao et al. | |
| 10,123,685 B2 | 11/2018 | Kermani | |
| 10,143,571 B2 | 12/2018 | Spence et al. | |
| 10,231,634 B2 | 3/2019 | Zand et al. | |
| 10,244,931 B2 | 4/2019 | Kern | |
| 10,251,695 B2 | 4/2019 | Fischer et al. | |
| 10,251,711 B2 | 4/2019 | Wood et al. | |
| 10,254,227 B2 | 4/2019 | Wang | |
| 10,267,999 B2 | 4/2019 | Van Der Mark et al. | |
| 10,285,583 B2 | 5/2019 | Parto et al. | |
| 10,285,759 B2 | 5/2019 | Lee et al. | |
| 10,292,783 B2 | 5/2019 | Bacher et al. | |
| 10,307,047 B2 | 6/2019 | Scheller et al. | |
| 10,307,290 B2 | 6/2019 | Kern et al. | |
| 10,325,366 B2 | 6/2019 | Mahadevan-Jansen et al. | |
| 10,342,416 B2 | 7/2019 | Bierhoff et al. | |
| 10,342,617 B2 | 7/2019 | Weckwerth et al. | |
| 10,342,618 B2 | 7/2019 | Grove et al. | |
| 10,362,942 B2 | 7/2019 | Mak et al. | |
| 10,363,099 B2 | 7/2019 | Ben Oren et al. | |
| 10,379,048 B2 | 8/2019 | Wang | |
| 10,398,465 B2 | 9/2019 | Darian | |
| 10,405,886 B2 | 9/2019 | Washburn, II et al. | |
| 10,413,167 B2 | 9/2019 | Gmeiner et al. | |
| 10,413,619 B2 | 9/2019 | Ikehara | |
| 10,426,396 B2 | 10/2019 | Lachenbruch et al. | |
| 10,426,857 B2 | 10/2019 | Boyden et al. | |
| 10,463,443 B2 | 11/2019 | Vayser | |
| 10,470,651 B2 | 11/2019 | Vijfvinkel | |
| 10,478,158 B2 | 11/2019 | Menard et al. | |
| 10,478,266 B2 | 11/2019 | Mirsepassi et al. | |
| 10,537,472 B2 | 1/2020 | Brennan et al. | |
| 10,582,843 B2 | 3/2020 | Klubben, III et al. | |
| 10,594,112 B1 | 3/2020 | Shang | |
| 10,610,408 B2 | 4/2020 | Farley | |
| 10,620,386 B2 | 4/2020 | Van Der Mark et al. | |
| 10,625,072 B2 | 4/2020 | Serrano Carmona | |
| 10,627,570 B2 | 4/2020 | Greene et al. | |
| 10,656,089 B2 | 5/2020 | Butte et al. | |
| 10,682,179 B2 | 6/2020 | Ransbury et al. | |
| 10,682,198 B2 | 6/2020 | McDowall et al. | |
| 10,687,912 B2 | 6/2020 | Dos Santos et al. | |
| 10,709,898 B2 | 7/2020 | Mori et al. | |
| 10,729,461 B2 | 8/2020 | Farley et al. | |
| 10,779,904 B2 | 9/2020 | Ransbury et al. | |
| 10,786,314 B2 | 9/2020 | Wood et al. | |
| 10,791,917 B2 | 10/2020 | Gmeiner et al. | |
| 10,806,537 B2 | 10/2020 | Mark et al. | |
| 10,813,554 B2 | 10/2020 | Lee et al. | |
| 10,842,587 B2 | 11/2020 | Mikus et al. | |
| 10,849,710 B2 | 12/2020 | Liu | |
| 10,850,046 B2 | 12/2020 | Isaacson et al. | |
| 10,859,748 B2 | 12/2020 | Mirsepassi et al. | |
| 10,863,890 B2 | 12/2020 | Lieponis | |
| 10,881,459 B2 | 1/2021 | Lim | |
| 10,888,227 B2 | 1/2021 | Kircher et al. | |
| 10,895,699 B2 | 1/2021 | Jochinsen | |
| 10,925,477 B2 | 2/2021 | Vayser et al. | |
| 10,939,815 B2 | 3/2021 | LaBelle et al. | |
| 10,945,615 B2 | 3/2021 | Franjic et al. | |
| 10,952,808 B2 | 3/2021 | Johnson | |
| 11,061,192 B2 | 7/2021 | Woodruff et al. | |
| 11,071,546 B2 | 7/2021 | Nicholas et al. | |
| 11,109,938 B2 | 9/2021 | Horn et al. | |
| 11,110,005 B2 | 9/2021 | Diao et al. | |
| 11,135,032 B2 | 10/2021 | Blus et al. | |
| 11,154,198 B2 | 10/2021 | Dacosta et al. | |
| 11,160,686 B2 | 11/2021 | Cook et al. | |
| 11,173,008 B2 | 11/2021 | Mirsepassi et al. | |
| 11,179,053 B2 | 11/2021 | Hashimshony et al. | |
| 11,185,234 B2 | 11/2021 | Beckman | |
| 11,206,987 B2 | 12/2021 | Yang et al. | |
| 11,241,587 B2 | 2/2022 | Lilge et al. | |
| 11,307,365 B2 | 4/2022 | Altshuler et al. | |
| 11,357,405 B2 | 6/2022 | Puppels et al. | |
| 11,369,366 B2 | 6/2022 | Scheib et al. | |
| 11,369,452 B2 | 6/2022 | Bacher et al. | |
| 11,395,713 B2 | 7/2022 | Grueebler et al. | |
| 11,399,898 B2 | 8/2022 | Gunn et al. | |
| 11,413,051 B2 | 8/2022 | Cushen et al. | |
| 11,426,196 B2 | 8/2022 | Rohl et al. | |
| 11,471,056 B2 | 10/2022 | Lee et al. | |
| 11,497,932 B2 | 11/2022 | Croll et al. | |
| 11,517,219 B2 | 12/2022 | Kaneko et al. | |
| 11,559,352 B2 | 1/2023 | Amirana et al. | |
| 11,701,013 B2 | 7/2023 | Franjic et al. | |
| 11,727,792 B2 | 8/2023 | Mirov | |
| 2001/0047136 A1 | 11/2001 | Domanik et al. | |
| 2002/0049386 A1 | 4/2002 | Yang et al. | |
| 2002/0068851 A1 | 6/2002 | Gravenstein et al. | |
| 2002/0135752 A1 * | 9/2002 | Sokolov | A61B 5/444 356/39 |
| 2003/0011764 A1 | 1/2003 | Braig et al. | |
| 2003/0078477 A1 | 4/2003 | Kang et al. | |
| 2003/0236458 A1 | 12/2003 | Hochman | |
| 2004/0039242 A1 | 2/2004 | Tolkoff et al. | |
| 2004/0152987 A1 | 8/2004 | Haisch | |
| 2004/0162503 A1 | 8/2004 | Dubnack et al. | |
| 2004/0249245 A1 | 12/2004 | Irion | |
| 2005/0165315 A1 | 7/2005 | Zuluaga et al. | |
| 2005/0234526 A1 | 10/2005 | Gilhuly et al. | |
| 2006/0004292 A1 | 1/2006 | Beylin | |
| 2006/0019220 A1 | 1/2006 | Loebel et al. | |
| 2006/0020310 A1 | 1/2006 | Loebel et al. | |
| 2006/0173353 A1 | 8/2006 | Uchida | |
| 2006/0211926 A1 | 9/2006 | Yu et al. | |
| 2007/0060804 A1 | 3/2007 | Thompson et al. | |
| 2007/0167836 A1 | 7/2007 | Scepanovic et al. | |
| 2007/0189031 A1 | 8/2007 | Delmar | |
| 2008/0108011 A1 | 5/2008 | Nahlieli | |
| 2008/0161748 A1 | 7/2008 | Tolkoff et al. | |
| 2009/0117053 A1 | 5/2009 | Li | |
| 2009/0117606 A1 | 5/2009 | Tunnell et al. | |
| 2009/0153850 A1 | 6/2009 | Nielsen et al. | |
| 2009/0266999 A1 | 10/2009 | Krattiger | |
| 2009/0310236 A1 | 12/2009 | Wu | |
| 2009/0326385 A1 | 12/2009 | Hendriks et al. | |
| 2010/0036261 A1 | 2/2010 | Weinberg et al. | |
| 2010/0081964 A1 | 4/2010 | Mark et al. | |
| 2010/0261965 A1 | 10/2010 | Beck et al. | |
| 2011/0007312 A1 | 1/2011 | Bushaw et al. | |
| 2011/0077465 A1 | 3/2011 | Mizuyoshi et al. | |
| 2011/0117025 A1 | 5/2011 | Dacosta et al. | |
| 2011/0118547 A1 | 5/2011 | Erikawa | |
| 2011/0149057 A1 | 6/2011 | Beck et al. | |
| 2011/0270092 A1 | 11/2011 | Kang et al. | |
| 2011/0275900 A1 | 11/2011 | Gilhuly et al. | |
| 2012/0010465 A1 | 1/2012 | Erikawa et al. | |

(56)  References Cited

U.S. PATENT DOCUMENTS

| | | | |
|---|---|---|---|
| 2012/0075619 A1 | 3/2012 | Nieman et al. | |
| 2012/0248333 A1 | 10/2012 | Fallert et al. | |
| 2012/0259231 A1 | 10/2012 | Tsubouchi et al. | |
| 2013/0006116 A1 | 1/2013 | Kim et al. | |
| 2013/0038479 A1 | 2/2013 | Eldar et al. | |
| 2013/0338479 A1 | 12/2013 | Pogue et al. | |
| 2014/0148729 A1 | 5/2014 | Schmitz et al. | |
| 2014/0207003 A1 | 7/2014 | Gilhuly et al. | |
| 2014/0235972 A1 | 8/2014 | Johnson et al. | |
| 2014/0236024 A1 | 8/2014 | Bierhoff et al. | |
| 2015/0038837 A1 | 2/2015 | Inoue et al. | |
| 2015/0088001 A1 | 3/2015 | Lindvold et al. | |
| 2015/0105668 A1 | 4/2015 | Ehrhardt et al. | |
| 2015/0148629 A1 | 5/2015 | Wilson et al. | |
| 2015/0238085 A1 | 8/2015 | Inoue et al. | |
| 2015/0304027 A1 | 10/2015 | Nciri | |
| 2015/0306428 A1 | 10/2015 | Darian | |
| 2015/0359525 A1 | 12/2015 | Hendriks et al. | |
| 2016/0129285 A1 | 5/2016 | Mikus et al. | |
| 2016/0151055 A1 | 6/2016 | Leblond et al. | |
| 2016/0178143 A1 | 6/2016 | Nciri et al. | |
| 2016/0245753 A1 | 8/2016 | Wang | |
| 2016/0287348 A1 | 10/2016 | Vayser et al. | |
| 2017/0020377 A1 | 1/2017 | Takeuchi et al. | |
| 2017/0020460 A1* | 1/2017 | Leblond | A61B 5/4842 |
| 2017/0035399 A1 | 2/2017 | Mak | |
| 2017/0045441 A1 | 2/2017 | Nciri | |
| 2017/0065346 A1* | 3/2017 | Weisberg | A61B 18/22 |
| 2017/0086938 A1 | 3/2017 | Mak et al. | |
| 2017/0156708 A1 | 6/2017 | Suehira et al. | |
| 2017/0176255 A1 | 6/2017 | Nciri | |
| 2017/0235118 A1 | 8/2017 | Kuster et al. | |
| 2017/0280988 A1 | 10/2017 | Barbato et al. | |
| 2017/0284940 A1 | 10/2017 | Butte et al. | |
| 2017/0290515 A1 | 10/2017 | Butte et al. | |
| 2018/0042482 A1 | 2/2018 | Stepp et al. | |
| 2018/0057852 A1 | 3/2018 | Takats et al. | |
| 2018/0070806 A1 | 3/2018 | Matsuo et al. | |
| 2018/0071030 A1 | 3/2018 | Wood et al. | |
| 2018/0153386 A1 | 6/2018 | Omori et al. | |
| 2018/0218508 A1 | 8/2018 | Lee et al. | |
| 2018/0270474 A1 | 9/2018 | Liu | |
| 2018/0310831 A1 | 11/2018 | Cheng et al. | |
| 2018/0325377 A1 | 11/2018 | Dacosta et al. | |
| 2018/0344993 A1 | 12/2018 | Ganz et al. | |
| 2018/0369458 A1 | 12/2018 | Mangual-Soto et al. | |
| 2019/0009102 A1 | 1/2019 | Mori et al. | |
| 2019/0108650 A1 | 4/2019 | De Haan et al. | |
| 2019/0117197 A1 | 4/2019 | Cheng et al. | |
| 2019/0246908 A1 | 8/2019 | Pyun et al. | |
| 2019/0262633 A1 | 8/2019 | Heijman et al. | |
| 2019/0267221 A1 | 8/2019 | Pringle et al. | |
| 2019/0376892 A1 | 12/2019 | Ishikawa et al. | |
| 2020/0093547 A1 | 3/2020 | Bendok et al. | |
| 2020/0100849 A1 | 4/2020 | Malackowski et al. | |
| 2020/0121384 A1 | 4/2020 | Mark et al. | |
| 2020/0138293 A1 | 5/2020 | Auner et al. | |
| 2020/0155004 A1 | 5/2020 | Kim et al. | |
| 2020/0170535 A1 | 6/2020 | Roberts et al. | |
| 2020/0179579 A1 | 6/2020 | Arnone et al. | |
| 2020/0246105 A1 | 8/2020 | Levesque et al. | |
| 2020/0261170 A1* | 8/2020 | Ziso | A61B 18/1477 |
| 2020/0297266 A1 | 9/2020 | Perelman | |
| 2020/0305696 A1 | 10/2020 | Abbas et al. | |
| 2020/0319108 A1 | 10/2020 | Butte et al. | |
| 2020/0352644 A1 | 11/2020 | Ransbury et al. | |
| 2020/0359901 A1 | 11/2020 | Phillips et al. | |
| 2020/0367818 A1 | 11/2020 | DaCosta et al. | |
| 2020/0383577 A1 | 12/2020 | Schie et al. | |
| 2021/0000521 A1 | 1/2021 | Tearney et al. | |
| 2021/0038304 A1 | 2/2021 | Bukesov et al. | |
| 2021/0045721 A1 | 2/2021 | Ruers et al. | |
| 2021/0052161 A1 | 2/2021 | Tsukashima et al. | |
| 2021/0059859 A1 | 3/2021 | O'Shea et al. | |
| 2021/0076940 A1 | 3/2021 | Schikora et al. | |
| 2021/0077796 A1 | 3/2021 | Hanson et al. | |
| 2021/0085194 A1 | 3/2021 | Franjic et al. | |
| 2021/0093168 A1 | 4/2021 | Deyanov | |
| 2021/0093412 A1 | 4/2021 | Yampolsky | |
| 2021/0137400 A1 | 5/2021 | Mirov | |
| 2021/0153731 A1 | 5/2021 | Murdeshwar | |
| 2021/0177540 A1 | 6/2021 | Abt | |
| 2021/0212670 A1 | 7/2021 | Babaris et al. | |
| 2021/0259552 A1 | 8/2021 | Dacosta et al. | |
| 2021/0298691 A1 | 9/2021 | Cohen et al. | |
| 2022/0034810 A1 | 2/2022 | Park | |
| 2022/0039744 A1 | 2/2022 | Koenig | |
| 2022/0054222 A1 | 2/2022 | Blus et al. | |
| 2022/0082500 A1 | 3/2022 | Dacosta et al. | |
| 2022/0087772 A1 | 3/2022 | Ryan et al. | |
| 2022/0219009 A1 | 7/2022 | Hata et al. | |
| 2022/0230334 A1 | 7/2022 | Lee et al. | |
| 2022/0276167 A1 | 9/2022 | Butte et al. | |
| 2022/0313300 A1 | 10/2022 | Buckley | |
| 2022/0400972 A1 | 12/2022 | Mattmueller | |
| 2022/0401094 A1 | 12/2022 | Zagatsky et al. | |
| 2022/0409325 A1 | 12/2022 | Kiel et al. | |
| 2023/0018956 A1 | 1/2023 | Leblond et al. | |
| 2023/0040005 A1 | 2/2023 | Charles | |
| 2023/0074634 A1 | 3/2023 | Albrecht et al. | |
| 2023/0133106 A1 | 5/2023 | Bush et al. | |
| 2023/0143152 A1 | 5/2023 | Major et al. | |

FOREIGN PATENT DOCUMENTS

| | | |
|---|---|---|
| CN | 111971005 B | 6/2023 |
| CN | 111481252 B | 7/2023 |
| EP | 1584285 A1 | 10/2005 |
| EP | 2704095 A1 | 3/2014 |
| EP | 2968922 B1 | 8/2018 |
| EP | 3973854 A1 | 3/2022 |
| EP | 3658044 B1 | 7/2023 |
| JP | 2004089533 A | 3/2004 |
| JP | 2004275569 A | 10/2004 |
| JP | 2006191989 A | 7/2006 |
| JP | 2008188160 A | 8/2008 |
| JP | 5467632 B2 | 4/2014 |
| KR | 101343868 B1 | 12/2013 |
| RU | 183278 U1 | 9/2018 |
| WO | 9721979 A1 | 6/1997 |
| WO | 9922814 A1 | 5/1999 |
| WO | 9942179 A1 | 8/1999 |
| WO | 0153871 A2 | 7/2001 |
| WO | 0228273 A2 | 4/2002 |
| WO | 02061405 A2 | 8/2002 |
| WO | 03024328 A2 | 3/2003 |
| WO | 03084601 A2 | 10/2003 |
| WO | 2004054439 A2 | 7/2004 |
| WO | 2004095359 A2 | 11/2004 |
| WO | 2005035059 A1 | 4/2005 |
| WO | 2005051215 A1 | 6/2005 |
| WO | 2005081795 A2 | 9/2005 |
| WO | 2005099563 A1 | 10/2005 |
| WO | 2006022970 A1 | 3/2006 |
| WO | 2007090591 A1 | 8/2007 |
| WO | 2008068685 A1 | 6/2008 |
| WO | 2008157476 A2 | 12/2008 |
| WO | 2010065827 A1 | 6/2010 |
| WO | 2011088571 A1 | 7/2011 |
| WO | 2012127378 A1 | 9/2012 |
| WO | 2013053876 A2 | 4/2013 |
| WO | 2013077808 A1 | 5/2013 |
| WO | 2013092740 A1 | 6/2013 |
| WO | 2013150745 A1 | 10/2013 |
| WO | 2013167824 A1 | 11/2013 |
| WO | 2013185087 A1 | 12/2013 |
| WO | 2014030344 A1 | 2/2014 |
| WO | 2014127379 A1 | 8/2014 |
| WO | 2014142741 A1 | 9/2014 |
| WO | 2015010213 A1 | 1/2015 |
| WO | 2015018844 A1 | 2/2015 |
| WO | 2015023990 A1 | 2/2015 |
| WO | 2015114379 A1 | 8/2015 |
| WO | 2015154187 A1 | 10/2015 |

(56) References Cited

FOREIGN PATENT DOCUMENTS

| WO | 2015156153 A1 | 10/2015 |
|---|---|---|
| WO | 2015164774 A1 | 10/2015 |
| WO | 2016127173 A1 | 8/2016 |
| WO | 2017021942 A1 | 2/2017 |
| WO | 2017079253 A1 | 5/2017 |
| WO | 2017079732 A1 | 5/2017 |
| WO | 2017109201 A1 | 6/2017 |
| WO | 2017110194 A1 | 6/2017 |
| WO | 2017135873 A1 | 8/2017 |
| WO | 2017173315 A1 | 10/2017 |
| WO | 2017177194 A8 | 12/2017 |
| WO | 2018019781 A1 | 2/2018 |
| WO | 2018156984 A1 | 8/2018 |
| WO | 2018195466 A1 | 10/2018 |
| WO | 2019114883 A1 | 6/2019 |
| WO | 2019147129 A2 | 8/2019 |
| WO | 2019148268 A1 | 8/2019 |
| WO | 2019191497 A1 | 10/2019 |
| WO | 2020068756 A1 | 4/2020 |
| WO | 2021074265 A1 | 4/2021 |
| WO | 2021151780 A1 | 8/2021 |
| WO | 2022051423 A1 | 3/2022 |
| WO | 2022069304 A1 | 4/2022 |
| WO | 2022190076 A1 | 9/2022 |
| WO | 2022238982 A1 | 11/2022 |

OTHER PUBLICATIONS

Henrich, Dominik et al., "Principles of Navigation in Surgical Robotics", Medical Robotics, Navigation and Visualisation, Remagen, Germany, Mar. 11-12, 2004, 10 pages.
Roberts, D.W. et al., "Coregistered fluorescence-enhanced tumor resection of malignant glioma: relationships between ?-aminolevulinic acid-induced protoporphyrin IX fluorescence, magnetic resonance imaging enhancement, and neuropathological parameters", Clinical article., J Neurosurg, vol. 114, No. 3, pp. 595-603.
RP Photonics Encyclopedia, "Fiber Couplers", https://www.rp-photonics.com/fiber_couplers.html, 2016-2023, 10 pages.
RP Photonics Encyclopedia, "Fiber Launch Systems", https://www.rp-photonics.com/fiber_launch_systems.html, 2016-2023, 10 pages.
Sanai, N et al. "Intraoperative Confocal Microscopy in the Visualization of 5-Aminolevulinic Acid Fluorescence in Low-Grade Gliomas", Journal of Neurosurgery, vol. 115, No. 4, 2011, pp. 740-748.
Shah, H.A, et al., "Utility of 5-ALA for fluorescence-guided resection of brain metastases: a systematic review", J Neurooncol, vol. 160, No. 3, pp. 669-675.
Signal Processing Devices, "Teledyne SP Devices ADQ108 Datasheet", https://www.mish.co.jp/doc/ADQ108.pdf, 2017, 10 pages.
Stummer, W. et al., "Technical Principles for Protoporphyrin-IX-Fluorescence Guided Microsurgical Resection of Malignant Glioma Tissue", Acta Neurochir (Wien), vol. 140, 1998, pp. 995-1000.
Stummer, W. et al., "Fluorescence-guided surgery with 5-aminolevulinic acid for resection of malignant glioma: a randomised controlled multicentre phase III trial", Lancet Oncol, vol. 7, No. 5, 2006, pp. 392-401.
Stummer, W., et al., "Extent of Resection and Survival in Glioblastoma Multiforme: Identification of and Adjustment for Bias", Neurosurgery, vol. 62, No. 3, 2008, pp. 564-576.
Stummer, Walter et al., "Fluorescence-Guided Surgery With 5-Aminolevulinic Acid for Resection of Malignant Glioma: A Randomised Controlled Multicentre Phase III Trial", The Lancet Oncology, vol. 7, No. 5, 2006, pp. 392-401.
Stummer, Walter et al., "Fluouescence-Guided Resection of Glioblastoma Multifome by Using 5-Aminolevulinic Acid-Induced Porphyrins: A Prospectiv Study in 52 Consecutive Patients", J Neurosurg, vol. 93, 2000, pp. 1003-1013.
Stummer, Walter et al., Interoperative Detection of Malignat Gliomas by 5-Aminolevulinic Acid-Induced Porphyrin Fluorescene, Neurosurgery, vol. 42, No. 3, Mar. 1998, pp. 518-526.

Stupp, R. et al., "Radiotherapy plus concomitant and adjuvant temozolomide for glioblastoma", N Engl J Med, vol. 325, No. 10, 2005, pp. 987-996.
Traylor, J.I. et al., "Molecular and Metabolic Mechanisms Underlying Selective 5-Aminolevulinic Acid-Induced Fluorescence in Gliomas", Cancers (Basel), vol. 13, No. 3, 2021, 15 pages.
U.S. Appl. No. 63/364,695, filed May 13, 2022.
Utsuki, S. et al., "Histological examination of false positive tissue resection using 5-aminolevulinic acid-induced fluorescence guidance", Neurol Med Chir (Tokyo), vol. 47, No. 5, 2007, Discussion 213-4, pp. 210-213.
Valdes, P.A. et al., "5-Aminolevulinic acid-induced protoporphyrin IX fluorescence in meningioma: qualitative and quantitative measurements in vivo", Neurosurgery, Suppl vol. 1, No. 1, Discussion 82-3, 2014, pp. 74-82.
Valdes, P.A. et al., "Optical technologies for intraoperative neurosurgical guidance", Neurosurg Focus, vol. 40, No. 3, 2016, p. E8.
Valdes, P.A. et al., "Quantitative fluorescence using 5-aminolevulinic acid-induced protoporphyrin IX biomarker as a surgical adjunct in low-grade glioma surgery", J Neurosurg, vol. 123, No. 3, 2015, pp. 771-780.
Valdes, P.A. et al., "System and methods for wide-field quantitative fluorescence imaging during neurosurgery", Opt Lett, vol. 38, No. 15, pp. 2786-278.
Valdes, Pablo A. et al., "Quantitative Fluorescence Using 5-Aminolevulinic Acid-Induced Protoporphyrin IX Biomarker as a Surgical Adjunct in Low-Grade Glioma Surgery", Journal of Neurosurgery, vol. 123, No. 3, 2015, pp. 771-780.
Valdes, Pablo A., et al. "?-Aminolevulinic Acid-induced Protoporphyrin IX Concentration Correlates With Histopathologic Markers of Malignancy in Human Gliomas: The Need for Quantitative Fluorescence-Guided Resection to Identify Regions of Increasing Malignancy." Neuro-oncology, vol. 13, No. 8, 2011, pp. 846-856.
Valdes, Pablo A., et al. "Quantitative Fluorescence in Intracranial Tumor: Implications for ALA-Induced PpIX as an Intraoperative Biomarker." Journal of Neurosurgery, vol. 115, No. 1, 2011, pp. 11-17.
Wang, G. et al., "Tumor-associated microglia and macrophages in glioblastoma: From basic insights to therapeutic opportunities", Front Immunol, vol. 13, 2022, p. 964898.
Widhalm, G. et al., "5-Aminolevulinic acid is a promising marker for detection of anaplastic foci in diffusely infiltrating gliomas with nonsignificant contrast enhancement", Cancer, vol. 116, No. 6, 2010, pp. 1545-1552.
Xia, Liang et al., "Relationship Between the Extent of Resection and the Survival of Patients With Low-Grade Gliomas: A Systematic Review and Meta-Analysis", BMC cancer, vol. 18, No. 48, 2018: 10 pages.
Zhang, Y. et al., "Single-cell RNA sequencing in cancer research", J Exp Clin Cancer Res, vol. 40, No. 1, 2021, p. 81.
Bettag, C. et al., "Endoscopic Fluorescence-Guided Resection Increases Radicality in Glioblastoma Surgery", Oper Neurosurg (Hagerstown), vol. 18, No. 1, 2020, pp. 41-46.
Bradley, R.S. et al., "A review of attenuation correction techniques for tissue fluorescence", J R Soc Interface, vol. 3, No. 6, 2006, pp. 1-13.
Brown, T.J. et al., "Association of the Extent of Resection With Survival in Glioblastoma: A Systematic Review and Meta-analysis", JAMA Oncol, vol. 2, No. 11, 2016, pp. 1460-1469.
Brown, T.J. et al., Management of Low-Grade Glioma: A Systematic Review and Meta-Analysis, Neuro-Oncology Practice, vol. 6, No. 4, 2019, pp. 249-258.
David, F.G. et al., "Glioblastoma incidence rate trends in Canada and the United States compared with England 1995-2015", Neuro Oncol, vol. 22, No. 2, 2020, pp. 301-302.
English language abstract and machine-assisted English language translation of claims (original document unavailable) for WO 2014/127379 A1 extracted from espacenet.com database on Sep. 14, 2023, 8 pages.
English language abstract and machine-assisted English translation for CN 208808702 U extracted from espacenet.com database on Sep. 14, 2023, 9 pages.

(56)  References Cited

OTHER PUBLICATIONS

English language abstract and machine-assisted English translation for JP 2004-275569 A extracted from espacenet.com database on Sep. 14, 2023, 5 pages.

English language abstract and machine-assisted English translation for JP 2008-188160 A extracted from espacenet.com database on Sep. 14, 2023, 13 pages.

English language abstract and machine-assisted English translation for JP 5467632 B2 extracted from espacenet.com database on Sep. 14, 2023, 13 pages.

English language abstract and machine-assisted English translation for WO 2007/090591 A1 extracted from espacenet.com database on Sep. 14, 2023, 9 pages.

English language abstract and machine-assisted English translation for WO 2013/053876 A2 extracted from espacenet.com database on Sep. 14, 2023, 22 pages.

English language abstract and machine-assisted English translation for WO 99/42179 A1 extracted from espacenet.com database on Sep. 14, 2023, 16 pages.

English language abstract for CN 110996816 B extracted from espacenet.com database on Sep. 14, 2023, 2 pages.

English language abstract for CN 111481252 B extracted from espacenet.com database on Sep. 14, 2023, 2 pages.

English language abstract for CN 111971005 B extracted from espacenet.com database on Sep. 14, 2023, 2 pages.

English language abstract for WO 03/024328 A2 extracted from espacenet.com database on Sep. 14, 2023, 1 page.

English language abstract for WO 2013/150745 A1 extracted from espacenet.com database on Sep. 14, 2023, 2 pages.

English language abstract for WO 2013/167824 A1 extracted from espacenet.com database on Sep. 14, 2023, 2 pages.

English language abstract for WO 2014/030344 A1 extracted from espacenet.com database on Sep. 14, 2023, 2 pages.

English language abstract for WO 2015/018844 A1 extracted from espacenet. com database on Sep. 14, 2023, 2 pages.

English language abstract for WO 2015/156153 A1 extracted from espacenet.com database on Sep. 14, 2023, 2 pages.

English language abstract for WO 2017/021942 A1 extracted from espacenet.com database on Sep. 14, 2023, 2 pages.

English language abstract for WO 2017/110194 A1 extracted from espacenet.com database on Sep. 14, 2023, 1 page.

English language abstract for WO 2019/114883 A1 extracted from espacenet. com database on Sep. 14, 2023, 2 pages.

English language abstract for WO 2021/074265 A1 extracted from espacenet.com database on Sep. 14, 2023, 2 pages.

English language abstract for WO 2021/151780 A1 extracted from espacenet.com database on Sep. 14, 2023, 1 page.

Ewelt, C. et al., "Finding the anaplastic focus in diffuse gliomas: the value of Gd-DTPA enhanced MRI, FET-PET, and intraoperative, ALA-derived tissue fluorescence", Clin Neurol Neurosurg, vol. 113, No. 7, 2011, pp. 541-547.

Fluke Networks, "What's an Expanded Beam Fiber Connector?", https://www.flukenetworks.com/blog/cabling-chronicles/whats-expanded-beam-fiber-connector, https://www.flukenetworks.com/blog/cabling-chronicles/whats-expanded-beam-fiber-connector, Feb. 9, 2021, 6 pages.

Golebiewska, A. et al., "Side population in human glioblastoma is non-tumorigenic and characterizes brain endothelial cells", Brain, vol. 136, Part 5, 2013, pp. 1462-1475.

Hadjipanayis, C. G. et al.., "What is the Surgical Benefit of Utilizing 5-ALA for Fluorescence-Guided Surgery of Malignant Gliomas?", Neurosurgery, vol. 77, No. 5, Nov. 2015, pp. 663-673.

Haj-Hosseini, Neda et al., "Optical Touch Pointer for Fluorescence Guided Glioblastoma Resection Using 5-Aminolevulinic Acid", Lasers in Surgery and Medicine, vol. 42, 2010, 6 pages.

Hosmann, A. et al., "5-ALA Fluorescence is a Powerful Prognostic Marker during Surgery of Low-Grade Gliomas (WHO Grade II)-Experience at Two Specialized Centers", Cancers (Basel), vol. 13, No. 11, 2021, 15 pages.

Inomed, "Dynamic Continuous Mapping of the Corticospinal Tract Brochure", 2015, 4 pages.

International Search Report for Application No. PCT/IB2022/052294 dated Jun. 20, 2022, 3 pages.

Jaber, M. et al., "The Value of 5-Aminolevulinic Acid in Low-grade Gliomas and High-grade Gliomas Lacking Glioblastoma Imaging Features: An Analysis Based on Fluorescence, Magnetic Resonance Imaging, 18F-Fluoroethyl Tyrosine Positron Emission Tomography, and Tumor Molecular Factors", Neurosurgery, vol. 78, No. 3, Discussion 411, 2016, pp. 401-411.

Kaneko, S. et al., "Fluorescence real-time kinetics of protoporphyrin IX after 5-ALA administration in low-grade glioma", J Neurosurg,, vol. 136, No. 1, 2022, pp. 9-15.

Knowledge Development for POF S.L., "Feasibility Analysis of Different Optical Connectivity Technologies", May 12, 2020, 20 pages.

Lacroix, M. et al., A Multivariate Analysis of 416 Patients with Glioblastoma Multiforme: Prognosis, Extent of Resection, and Survival, Journal of Neurosurgery, vol. 95, No. 2, 2001, pp. 190-198.

Lieber, Chad A. et al., "Automated Method for Subtraction of Fluorescence from Biological Raman Spectra", Applied Spectroscopy, vol. 57, No. 11 2003, pp. 1363-1367.

Louis, D.N. et al., The 2021 WHO Classification of Tumors of the Central Nervous System: a summary:, Neuro Oncol, vol. 23, No. 8, 2021, pp. 1231-1251.

Machine-assisted English language abstract and machine-assisted English translation for RU 183278 U1 extracted from espacenet.com database on Sep. 14, 2023, 9 pages.

McNicholas, K., "In order for the light to shine so brightly, the darkness must be present—why do cancers fluoresce with 5-aminolaevulinic acid?", Br J Cancer, vol. 121, No. 8, 2019, pp. 631-639.

Morshed, Ramin A., et al. "Wavelength-Specific Lighted Suction Instrument for 5-aminolevulinic Acid Fluorescence-Guided Resection of Deep-Seated Malignant Glioma." Journal of Neurosurgery vol. 128, 2018, pp. 1448-1453.

Novotony, A. et al., "Mechanisms of 5-aminolevulinic acid uptake at the choroid plexus", J Neurochem, 2000. vol. 75, No. 1, pp. 321-328.

O'Haver, Tom, "A Pragmatic Introduction to Signal Processing—Curve Fitting C: Non-Linear Iterative Curve Fitting", Department of Chemistry and Biochemistry, The University of Maryland, https://terpconnect.umd.edu/~toh/spectrum/CurveFittingC.html, Jul. 2021, 25 pages.

Oscopes, "Digitizer and Oscilloscope—Equal Alternatives?", http://www.oscopes.info/basics/2320-digitizer-or-oscilloscope, 2022-2023, 6 pages.

Raabe, M.D., Andreas et al., "Continuous Dynamic Mapping of the Corticospinal Tract During Surgery of Motor Eloquent Brain Tumors; Evaluation of a New Method", Department of Neurosurgery, Bern, Switzerland, 2014, 10 pages.

Reinert, M. et al., "Quantitative Modulation of PpIX Fluorescence and Improved Glioma Visualization", Front Surg, vol. 6, 2019, p. 41.

Richards-Kortum, Rebecca, "Quantitative Optical Spectroscopy for Tissue Diagnosis", Annu. Rec. Phys. Chem. 1996, pp. 555-606.

English language abstract and machine-assisted English translation for JP 2004-089533 A extracted from espacenet. com database on Nov. 18, 2025, 12 pages.

English language abstract and machine-assisted English translation for JP 2006-191989 A extracted from espacenet. com database on Nov. 18, 2025, 10 pages.

* cited by examiner

116

Tissue Detection System

208

User Interface

Display

212

Power Supply

220

Microcontroller

215

224   Optical System   216

Spectrometer

Optical Block

228

Excitation Source(s)

204

Controller

265

Mapping Module

266

Electrode

Sample Element

296

Indicator Element

264

Detection Fiber

NEUROSURGICAL METHODS AND SYSTEMS FOR DETECTING AND REMOVING TUMOROUS TISSUE

CROSS-REFERENCE TO RELATED APPLICATIONS

This application is the National Stage of International Patent Application No PCT/IB2022/052294, filed on Mar. 14, 2022, which claims priority to and all the advantages of U.S. Provisional Patent Application No. 63/160,099, filed on Mar. 12, 2021, the contents of which are incorporated herein by reference.

BACKGROUND

Glioma tumors may start in the glial cells of the brain or the spine. A surgical procedure, more specifically tumor resection, is often performed to resect the tumor. The goal of a surgical procedure for tumor resection is to achieve gross total resection (GTR). A very aggressive form of glioma is glioblastoma. In patients with glioblastoma, GTR has been shown to prolong the life of a patient by about 40% (e.g., from 10 months to 14 months). In patients with lower-grade gliomas, GTR increases the overall chances of survival.

5-Aminolevulinic Acid (5-ALA) is often given to patients a couple hours before surgery. 5-ALA is a compound that occurs naturally in the hemoglobin synthesis pathway. In cancer cells, the hemoglobin synthesis is disrupted and the pathway stalls at an intermediate compound called Protoporphyrin IX (PPIX). During surgery, the healthcare professional may illuminate an area of brain tissue with excitation light (i.e., blue light) from a surgical microscope. The surgery may be carried out in a darkened or dimmed operating room environment. High-grade tumor cells containing PPIX absorb the excitation light and emit fluorescence (i.e., red fluorescence) having specific optical characteristics. The fluorescence may be observed by the healthcare professional from the surgical microscope.

Once the target tissue has been identified, the healthcare professional switches the surgical microscope back to standard white light illumination and continues to resect the target tissue. The healthcare professional switches back and forth between illuminating the tissue with white light and the excitation light throughout the surgical procedure to ensure the appropriate target tissue is being resected until the tumor resection is complete. Each time the target area is illuminated with the excitation light from the surgical microscope, the PPIX present at the tumor site may degrade due to photo-bleaching from being illuminated by the strong excitation light.

Fluorescence guided surgery increases the chances of GTR in high-grade tumors such as with glioblastoma tumors. At present, GTR of lower grade tumors is comparatively low because 5-ALA cannot be used to improve the outcome of lower-grade tumor resection as the tumor cells only emit a low level of fluorescence and the human eye is not sensitive enough to detect such low levels of fluorescence even with the use of the surgical microscope. A need exists for an improved system for fluorescence guided surgery that improves the chances of achieving GTR.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In a feature, a neurosurgery system for probing brain tissue of a patient for tumorous tissue is described. The neurosurgery system includes a suction tool configured to apply suction to tissue of the patient. The suction tool includes a suction cannula defining a lumen, an optical fiber, coupled to the suction cannula, the optical fiber being configured to transmit a fluorescence emitted by the brain tissue, and an indicator coupled to the suction cannula and configured to selectively emit visible light. The visible light being different from the fluorescence transmitted by the optical fiber. The neurosurgery system also includes an excitation source configured to emit an excitation light. The excitation light having a wavelength to induce the fluorescence in the tumorous tissue. The neurosurgery system also includes an optical instrument coupled to the optical fiber. The optical instrument is configured to convert the fluorescence emitted by the brain tissue and transmitted by the optical fiber into an electrical signal. The neurosurgery system also includes a controller that is coupled to the indicator and the optical instrument and configured to determine that the brain tissue is tumorous based on the electrical signal and activate the indicator based on the determination that the brain tissue is tumorous.

In a feature, a neurosurgical method for detecting whether brain tissue of a patient includes tumorous tissue is described. The neurosurgical method performed using a surgical system including a suction tool with an optical fiber and an indicator each coupled to the suction tool, an excitation source, an optical instrument coupled to the optical fiber, and a controller coupled to the excitation source, the optical instrument, and the indicator. The neurosurgical method comprising applying, with the suction tool, suction to the brain tissue of the patient. The neurosurgical method also includes emitting, with excitation light having a predetermined wavelength from the excitation source, to induce a fluorescence in the tumorous tissue. The neurosurgical method also includes collecting, with the optical fiber, the fluorescence emitted from brain tissue. The neurosurgical method also includes converting, with the optical instrument, the fluorescence into an electrical signal. The neurosurgical method also includes activating, with the controller, the indicator based on the electrical signal when the controller determines that the electrical signal indicates that the brain tissue is tumorous.

In a feature, a neurosurgical method for detecting whether target brain tissue is tumorous under ambient light conditions in an operating room using a surgical system is described. The surgical system includes a working tool including at least one optical fiber and an indicator, an optical instrument coupled to the at least one optical fiber, and an excitation source coupled to the at least one optical fiber, and a controller connected to the optical instrument and the indicator. The neurosurgical method for detecting target tissue including detecting fluorescence emitted from the target brain tissue during a surgical procedure. The step of detecting the fluorescence includes emitting blue light from the excitation source to induce fluorescence emission of the target brain tissue. The step of detecting the fluorescence also includes receiving, with the optical instrument, the fluorescence of the target brain tissue from the at least one optical fiber. The step of detecting the fluorescence also includes converting, with the optical instrument, the fluorescence into an electrical signal. The neurosurgical method also includes determining, with the controller, that the target brain tissue is tumorous based on the electrical signal. The neurosurgical method also includes activating, with the controller, the indicator of the working tool in response to the determination that the target brain tissue is tumorous.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

4

Figure 18A:
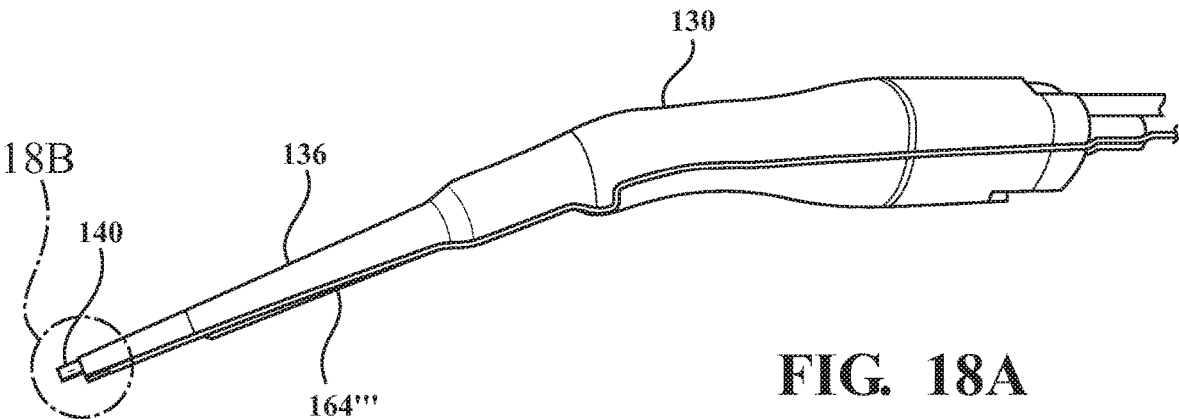
Figure 18B:
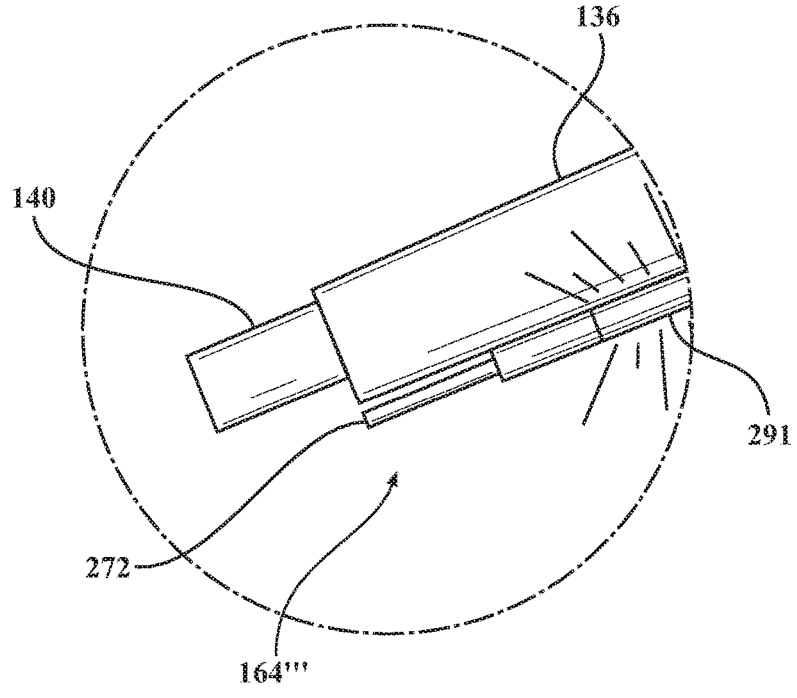

FIGS. 18A and 18B depict a sample element of a tissue detection system coupled to an ultrasonic handpiece assembly according to the teachings of the present disclosure.

Figure 19A:
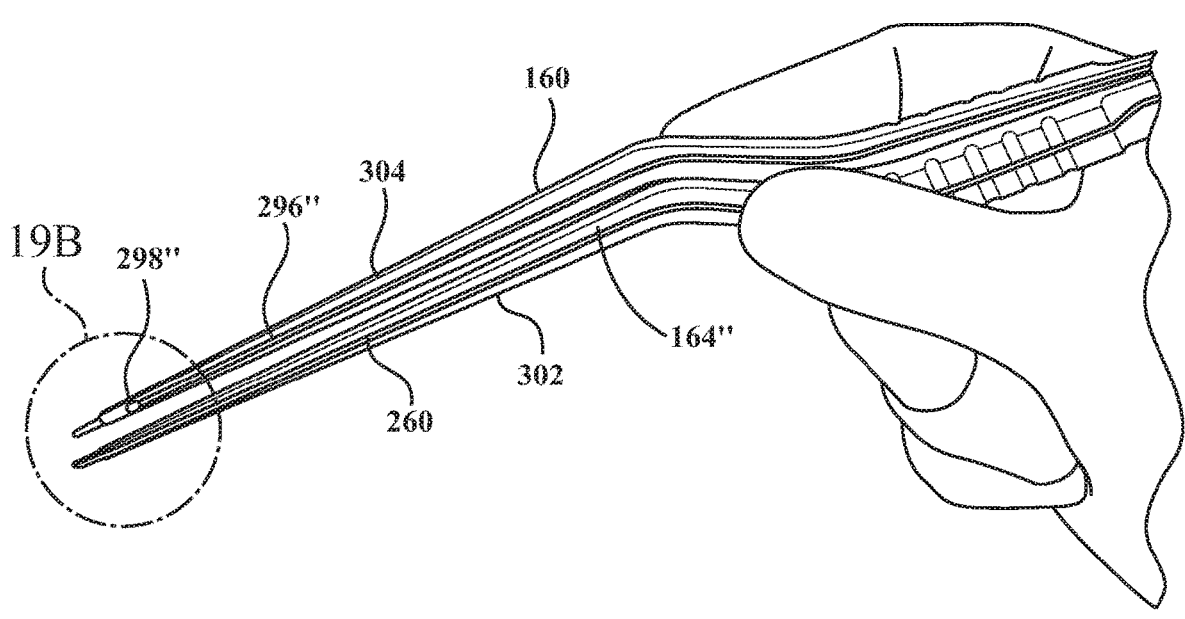
Figure 19B:
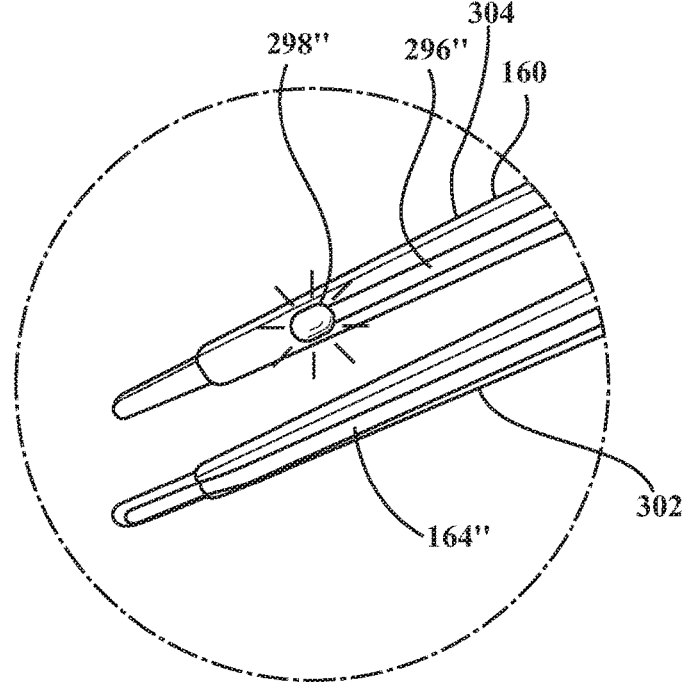

FIGS. 19A and 19B depict a sample element and an indicator element of a tissue detection coupled to bipolar forceps of a surgical system according to the teachings of the present disclosure.

Figure 20:
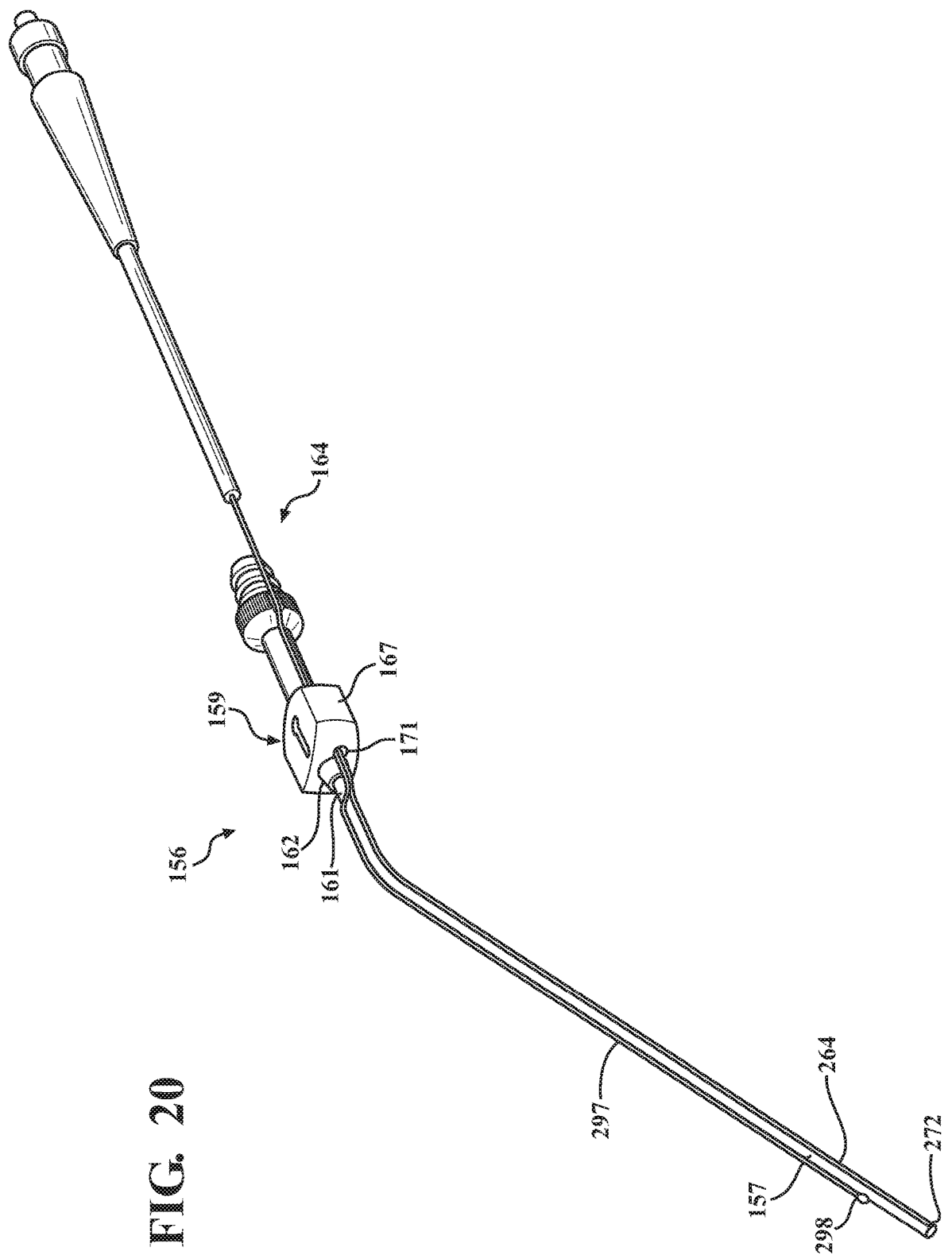

FIG. 20 depicts a sample element coupled to a suction tool of a suction system with a jacket removed according to the teachings of the present disclosure.

Figure 21:
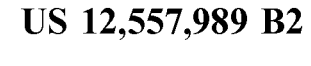

FIG. 21 depicts a sample element coupled to a suction tool of a suction system according to the teachings of the present disclosure.

Figure 22:
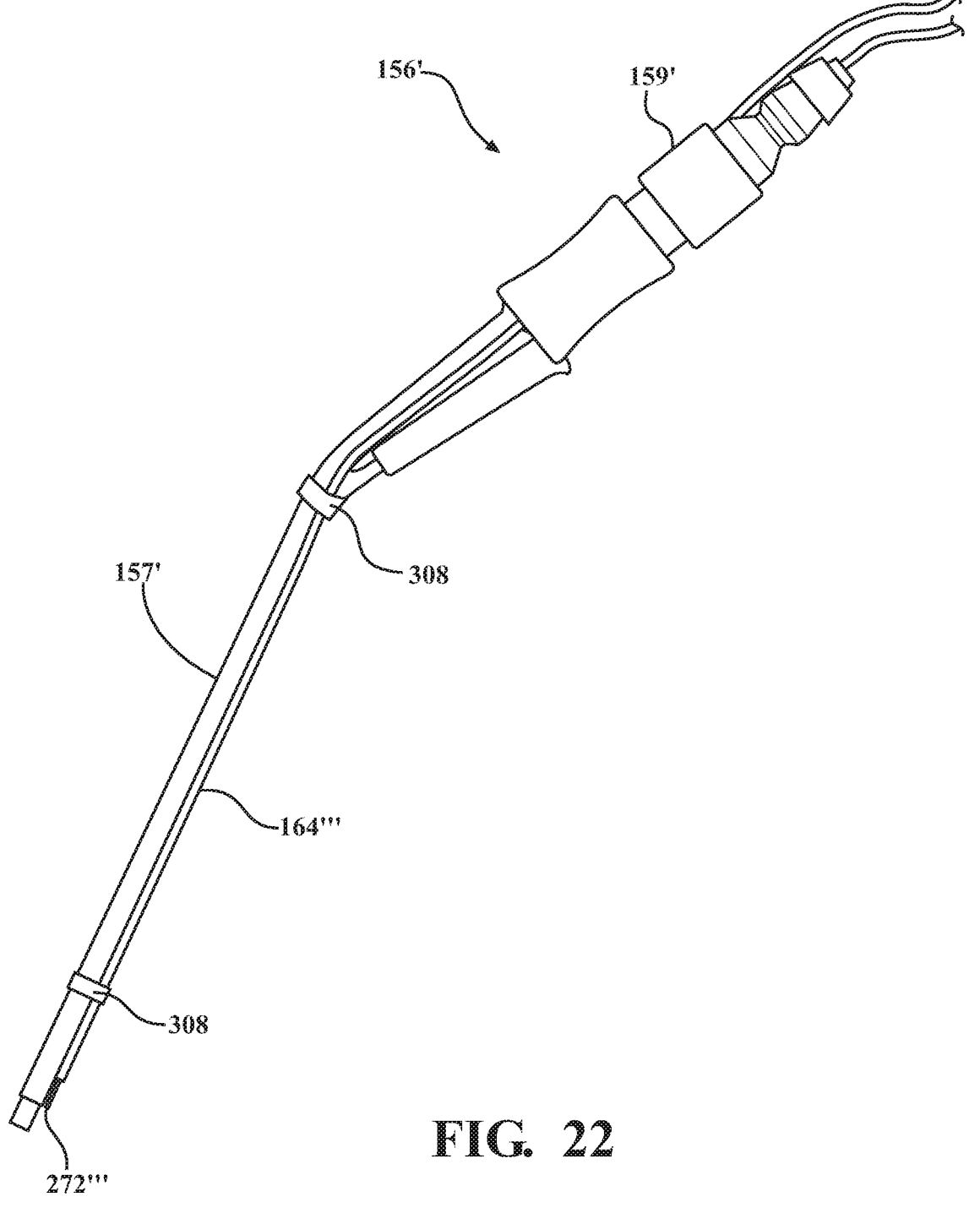

FIG. 22 depicts a sample element coupled to a suction tool of a suction system according to the teachings of the present disclosure.

In the drawings, reference numbers may be reused to identify similar and/or identical elements.

DETAILED DESCRIPTION

The present inventors realized that there exists a need for a neurosurgical tumor resection system and/or method that is capable of detecting low levels of fluorescence in white light operating conditions (i.e., not requiring a darkened or dimmed operating room) while in the process of resecting the tumor. There also exists a need for a system that can reduce the amount of time that the target area is illuminated with excitation light to reduce the effects of photo-bleaching. Additionally, there exists a need for a system that can illuminate excitation light in deep cavities as surgical microscope fail to adequately illuminate excitation light in deep cavities. Lastly, there exists a need for a system that assists in intraoperative detection of the anaplastic focus of the tumor which is of importance because finding the anaplastic focus is imperative for precise histopathological diagnosis and optimal patient treatment.

While the disclosure specifically discusses a surgical procedure related to resection of target tissue of a brain tumor with the administration of 5-ALA to visualize fluorescence of PPIX, the teachings of the present disclosure may be extended to other types of surgical procedures, to detect other types of tissue, and to detect other types of fluorophores (Hypericin, Hexvix, Idocyanine Green "ICG", etc.). For example, ICG may be administered to help a healthcare professional visualize blood vessels during the surgical procedure. ICG may bond to plasma protein found in blood. ICG is excited by near infrared light and emits near infrared light having a slightly longer wavelength than the near infrared light that excited the ICG.

Figure 1:
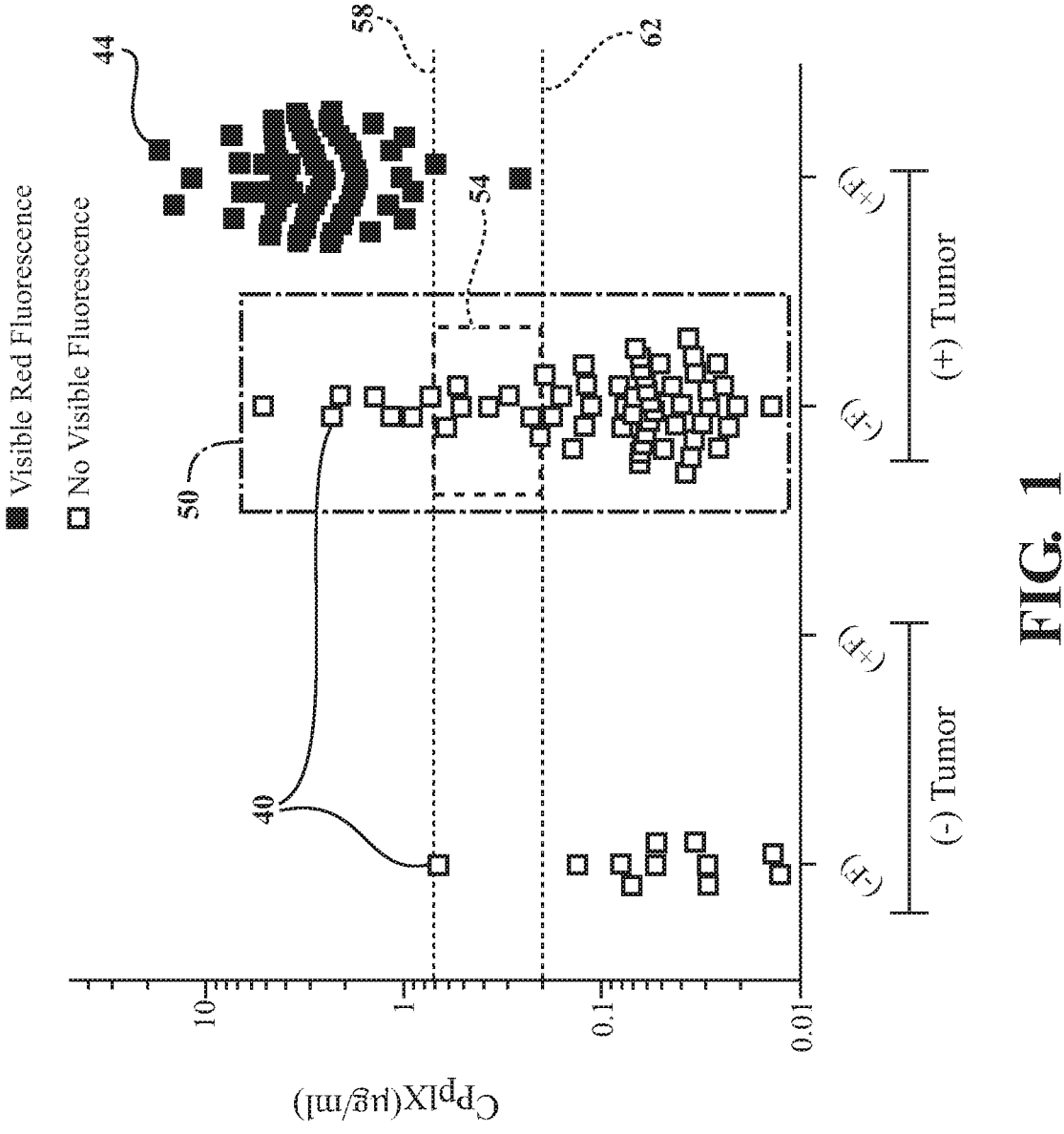
FIG. 1 depicts a chart depicting the visibility of red fluorescence of tumor tissue when viewed from a surgical microscope according to the teachings of the prior art.

With respect to FIG. 1, chart 10 depicts the visibility of the red fluorescence of PPIX when viewed from a surgical microscope. During brain tumor resection surgery, target tissue (i.e., tumor tissue) including elevated concentrations of PPIX may inadvertently be missed when tumor resection surgery is performed according to the systems of the prior art (i.e., with a surgical microscope) which leads to less than GTR. Thus, a more accurate way of detecting elevated concentrations of PPIX would prove to be very beneficial in helping to achieve GTR. Hollow squares 40 indicate specimens that produce no visible fluorescence and solid squares 44 indicate specimens that produce visible fluorescence. The y-axis shows the accumulated levels of $C_{PPIX}$ above a threshold of 0.1 μg/mL. The x-axis indicates visible fluorescence (+F) and non-visible fluorescence (−F) for healthy tissue and for target tissue. Region 50 represents a false negative region in which PPIX was present in the specimen but did not produce visible light. In particular, a sub-region 54 within the region 50 includes specimens below a level 58 that when viewed from a surgical microscope but still considered to include elevated levels 62 of $C_{PpIX}$. Thus, if the healthcare professional were to miss PPIX corresponding to the sub-region, GTR would not be achieved.

Figure 2:
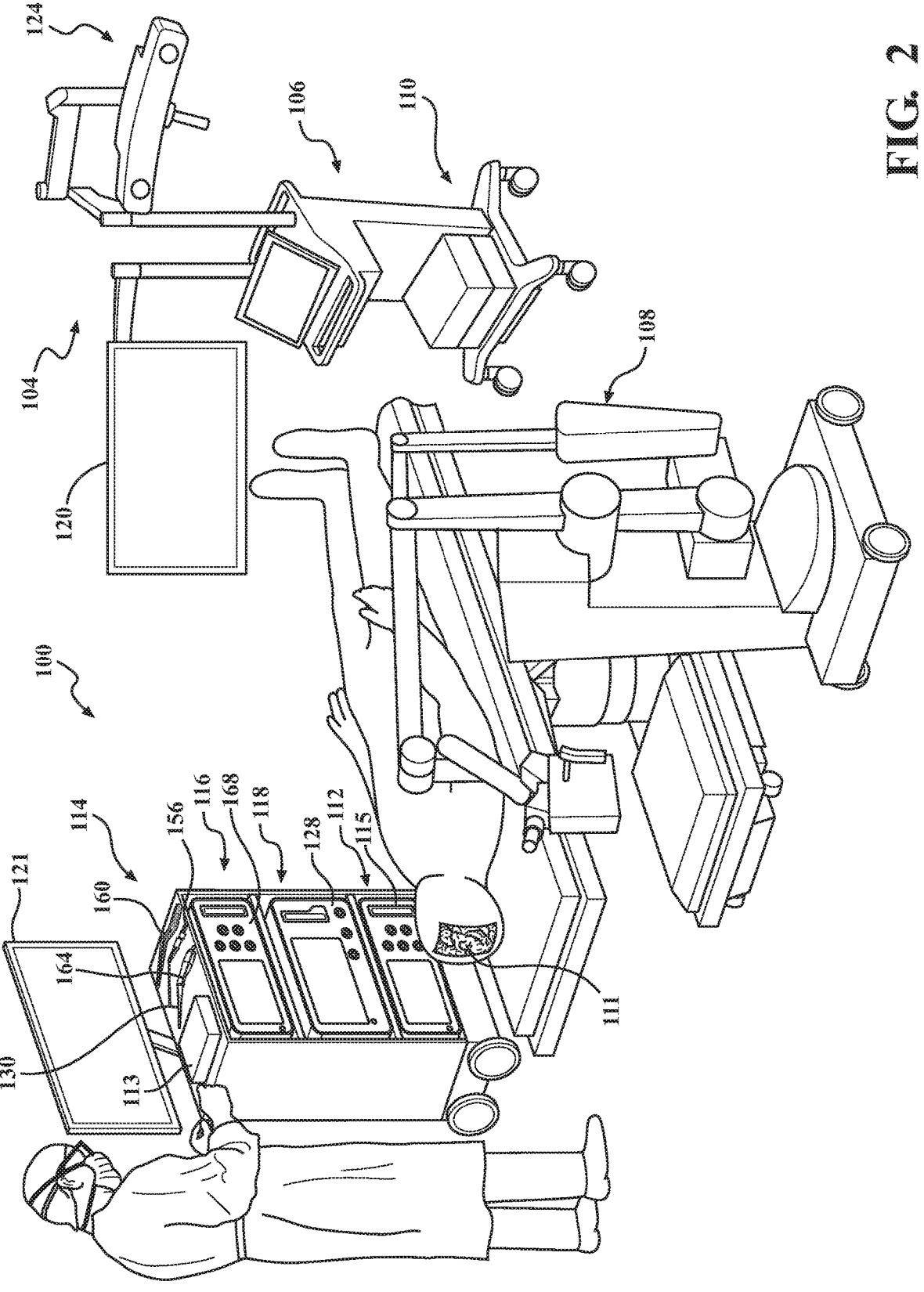
FIG. 2 depicts a neurosurgical system according to the teaching of the present disclosure.

With reference to FIG. 2, the neurosurgical system 100 is provided that solves the shortcomings of the prior art. The neurosurgical system 100 may include a surgical navigation system 104, a surgical microscope 108, a surgical cart 114, and a suction system 113. The surgical navigation system 104 includes a cart assembly 106 that houses a navigation computer 110. The navigation computer 110 may also be referred to as the navigation controller. A navigation interface is in operative communication with the navigation computer 110. The navigation interface may include one or more input devices may be used to input information into the navigation computer 110 or otherwise to select/control certain aspects of the navigation computer 110. The navigation interface includes one or more displays 120. Such input devices may include interactive touchscreen displays/menus, a keyboard, a mouse, a microphone (voice-activation), gesture control devices, or the like.

The navigation computer 110 may be configured to store one or more pre-operative or intra-operative images of the brain. Any suitable imaging device may be used to provide the pre-operative or intra-operative images of the brain. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), positron emission tomography (PET), optical coherence tomography (OCT). The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities.

The navigation computer 110 may generate the one or more images of the brain on a display 120. The navigation computer 110 may also be connected with the surgical microscope 108. For example, the display 120 may show an image corresponding to the field of view of the surgical microscope 108. When the navigation computer 110 may include more than one display, with one such display showing the field of view of the surgical microscope 108 while the other such display may show a pre-operative or intra-operative image of the brain.

The tracking system 124 is coupled to the navigation computer 110 and is configured to sense the position of one or more tracking elements attached to a surgical tool or the patient. The tracking system 124 may be configured to track active or passive infrared tracking elements attached to the surgical tool or the patient. An example of a surgical navigation system 104 that may be used is Nav3i™ that is commercially available from Stryker. A surgical navigation system 104 may have various functions and features as described in U.S. Pat. No. 7,725,162 B2 and U.S. Pat. Pub. No. 2020/0100849 A1 which are hereby incorporated by reference in their entireties.

The surgical microscope 108 includes one or more objectives configured to provide magnification in a range (e.g., from about 2 times to about 50 times). The surgical microscope 108 can have a field of view having an area of a predetermined range. The surgical microscope 108 is configured for fluorescence microscopy, for example, to detect PPIX. The surgical microscope 108 may include one or more excitation sources (e.g., an excitation source configured to emit light in the visible light spectrum or an excitation source configured to emit light in the infrared spectrum) for illuminating the brain tissue 111 with excitation light to cause the PPIX to fluorescence. The surgical microscope 108 may also include a camera capable of detecting radiation at the fluorescent wavelengths of PPIX or ICG.

The surgical cart 114 may include a surgical system 112, a suction system 113, a tissue detection system 116, and an ultrasonic surgical system 118. A display 121 may be coupled to the surgical cart and operatively connected to the surgical system 112, the tissue detection system 116, and/or the ultrasonic surgical system 118 to display information related with each respective system 112, 116, and 118. A healthcare professional may use the ultrasonic surgical system 118 and/or the surgical system 112 to ablate target tissue of the brain of the patient. The ultrasonic surgical system 118 may include an ultrasonic control console 128 and an ultrasonic handpiece assembly 130.

The suction system 113 may include a suction tool 156 and suction unit 117 to control various aspects of the suction tool 156. A suction tube may connect the suction tool 156 to the suction system 113. The suction system 113 may receive suction from a vacuum source, such as a vacuum outlet of a medical facility. The suction system 113 may include one or more regulators or one or more adjustment valves for controlling the suction pressure received from the vacuum source. The suction system 113 may also include one or more containers for storing the waste collected by the suction tool 156. In an example, the suction system 113 may correspond to a wall suction unit. In another example, the suction system 113 may correspond to a portable suction unit. The suction system 113 and the suction tool 156 may have various features, as described in U.S. Pat. No. 9,066,658 and U.S. Pat. Pub. No. 20180344993 which are hereby incorporated herein by reference in its entirety.

The surgical system 112 may include a surgical tool, such as bipolar forceps 160, and a surgical control console 115 to control various aspects of the surgical tool. The healthcare professional may also use the surgical tool to perform any surgical operation on the tissue. For example, to ablate the tissue or to cauterize the tissue. The bipolar forceps may have features, as described in U.S. Pat. No. 8,361,070 B2 which is hereby incorporated by reference in its entirety. While the disclosure discusses and illustrates that the surgical tool may include bipolar forceps 160, the surgical system 112 and surgical tool may include other tools, such as a neuro stimulator, a dissector, or an ablation device (e.g., an RF ablation device and/or a laser ablation device). For example, the surgical system and/or surgical tools may have various features as described in U.S. Pat. No. 8,267,934, which is hereby incorporated by reference in its entirety. Any number of surgical systems and any number of surgical tools may be employed by the healthcare professional in performing the surgical procedure.

The tissue detection system 116 may include a control console 168 and a sample element 164 (illustrated as coupled to the ultrasonic handpiece assembly 130). The control console 168 may provide the healthcare professional with a real-time indication via the sample element 164 when brain tissue 111 corresponds to the target tissue. The sample element 164 may also be coupled to the bipolar forceps 160, the suction tool 156, or other surgical tools as will be described in greater detail below. The tissue detection system 116 determines when the brain tissue 111 corresponds to target tissue based on fluorescence emitted by the target tissue caused by the fluorophore. In an example, the fluorophore may correspond to PPIX. In another example, the fluorophore may correspond to ICG. As will be discussed in greater detail below, based on the intensity and the wavelengths of the fluorescence emitted by PPIX, the tissue detection system 116 may determine that the target tissue is present.

Figure 3:
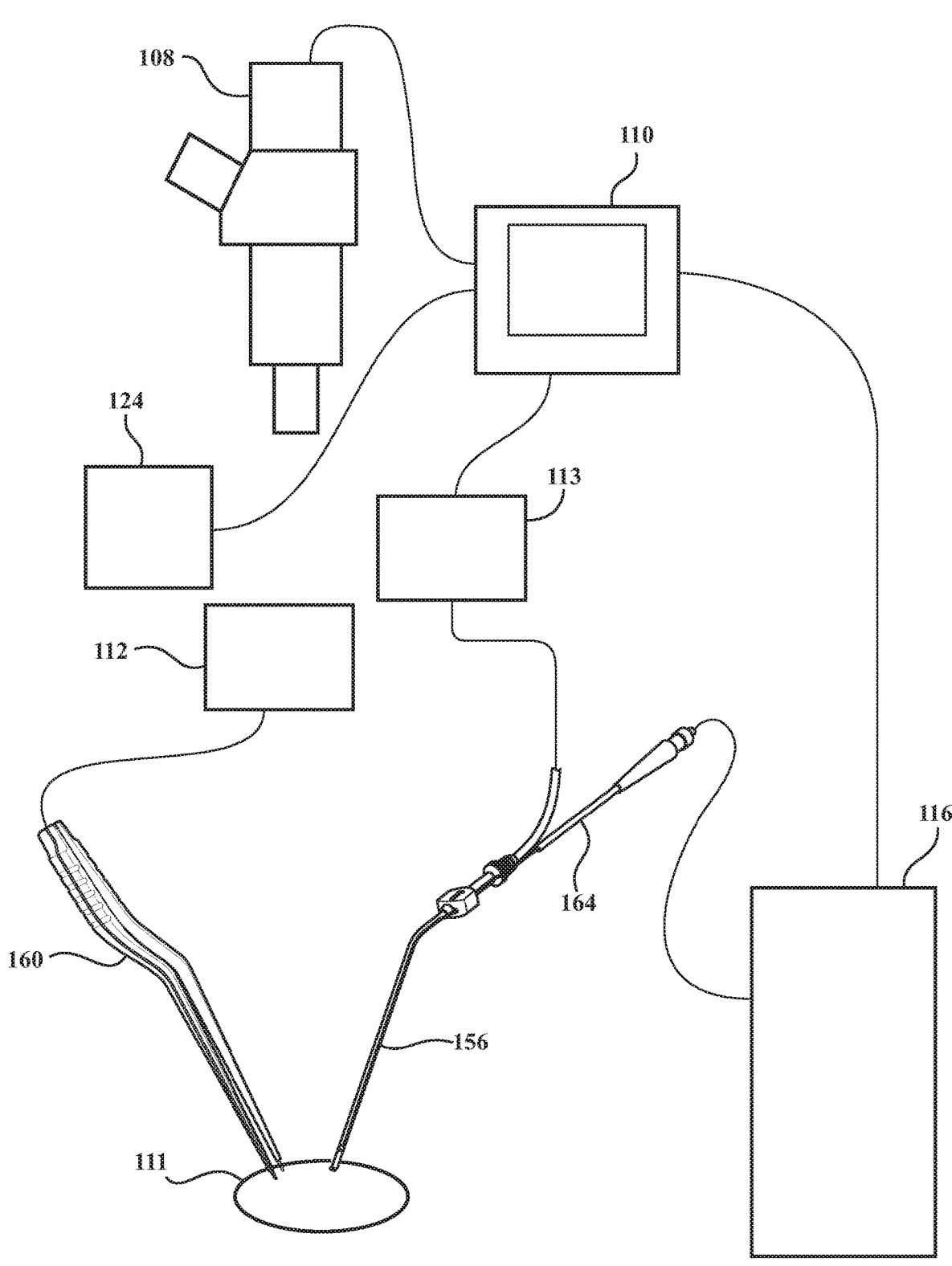
FIG. 3 depicts a functional block diagram of a neurosurgical system according to the teachings of the present disclosure.

With reference to FIG. 3, a schematic of the neurosurgical system 100 is shown. The tissue detection system 116, although capable of performing a similar function (i.e., allowing the healthcare professional to detect the presence of PPIX) to the surgical microscope 108, may be used in conjunction with the surgical microscope 108 to improve the outcome of a tumor resection procedure and the chances of achieving GTR.

During the surgical procedure, the healthcare professional may initially view the brain tissue 111 of the patient with the surgical microscope 108 under excitation light (e.g., the blue light) to identify which portion of the brain tissue 111 corresponds to the target tissue evidenced by the red fluorescence. The healthcare professional may switch the surgical microscope 108 back to standard white light illumination for better visibility and begin resection of the target tissue. Since the sample element 164 is coupled to the suction tool 156, the healthcare professional does not have to account for any additional surgical tools (i.e., optical probes or the like) in the sterile field. The healthcare professional may perform the resection of the target tissue with the bipolar forceps 160 in the one hand and the suction tool 156 in the other hand.

As the healthcare professional is resecting the target tissue, the control console 168 may function to provide the healthcare professional with a real-time indication of the target tissue in the brain tissue 111 by activation of an indicator (discussed in greater detail below) of the sample element 164. The tissue detection system 116 according to the teachings of the present disclosure prevents the healthcare professional from having to switch back and forth between the various illumination settings of the surgical microscope 108 (i.e., illuminating the tissue with excitation light and white light) as the healthcare professional is performing resection of the target tissue. This becomes especially important as the healthcare professional approaches the margin of the target tissue because it is desirable for the healthcare professional to achieve GTR but to leave as much healthy tissue intact as possible.

Figure 4:
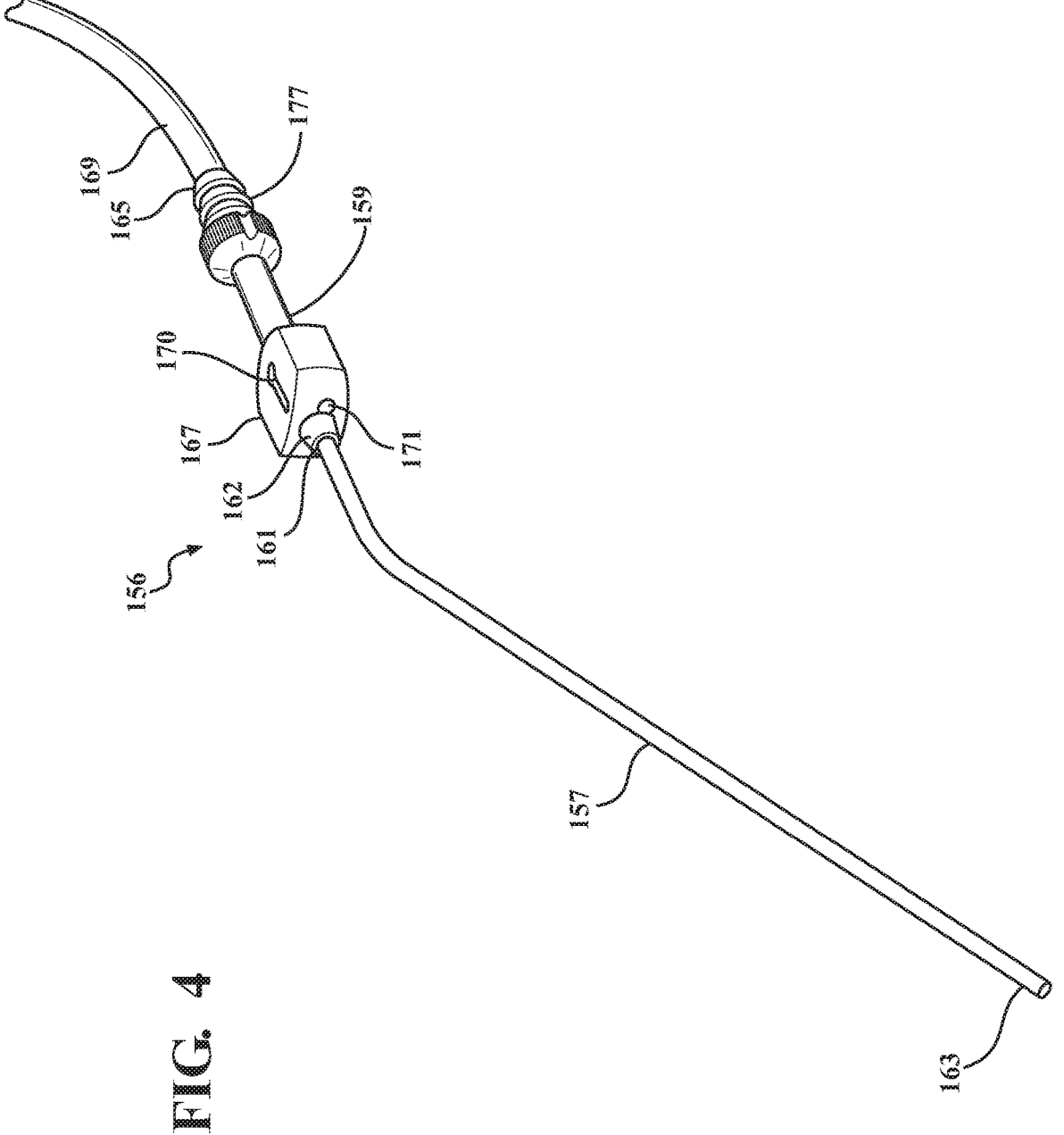
FIG. 4 depicts an example suction tool of the neurosurgical system according to the teachings of the present disclosure.

With reference to FIG. 4, the suction tool includes a suction cannula 157 and a handle 159. The suction cannula 157 defines a lumen for suctioning fluid, debris, and tissue from a patient. The handle 159 is tubular shaped with a control portion 167 that may be square shaped. A distal end 162 may be tapered and is configured to receive a proximal end 161 of a suction cannula 157. A distal end 165 of the handle 159 includes a vacuum fitting which may be configured to receive a suction tube 169 which is connected to the vacuum source which generates the suction pressure. The vacuum fitting may be a standard barbed fitting, quick disconnect, or any other suitable fitting known in the art to allow the suction tube to be fluidly coupled to a vacuum source.

Figures 5A, 5B:
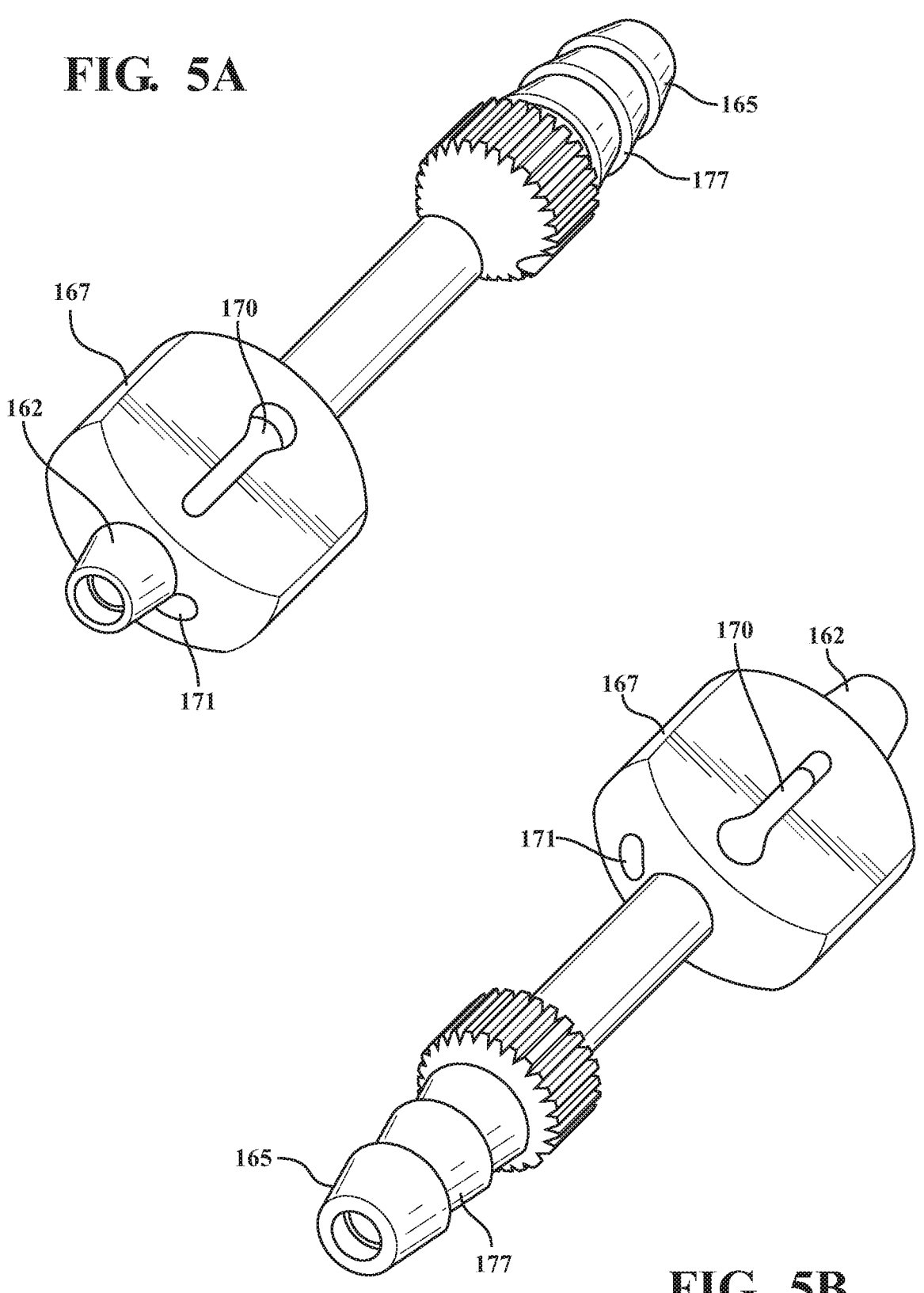
FIGS. 5A and 5B depict an example handle of a suction tool of the neurosurgical system according to the teachings of the present disclosure.

With additional reference to FIGS. 5A and 5B, the control portion 167 may include a teardrop shaped control 170 for regulation of suction pressure. For example, when no portion of the teardrop shaped control 170 is covered by the healthcare professional, suction pressure may be minimal, and when the teardrop shaped control 170 is covered completely, suction pressure may be at its maximum. While the control portion 167 is described as including a teardrop shaped control, the control portion 167 may include another suitable input such as a button or different shaped control to allow the healthcare professional to vary the suction pressure. The control portion includes a through bore 171 for receiving the sample element 164, as will be discussed in greater detail below. The healthcare professional holds the suction tool 156 from its handle 159, manipulating the suction tool 156 so that the distal end 163 contacts the tissue of the patient during the surgical procedure in order to provide suction at the desired location. While the suction tool 156 is described as having a Fukushima configuration, other configurations are contemplated such as a Frazier or Poole configuration.

Figure 6:
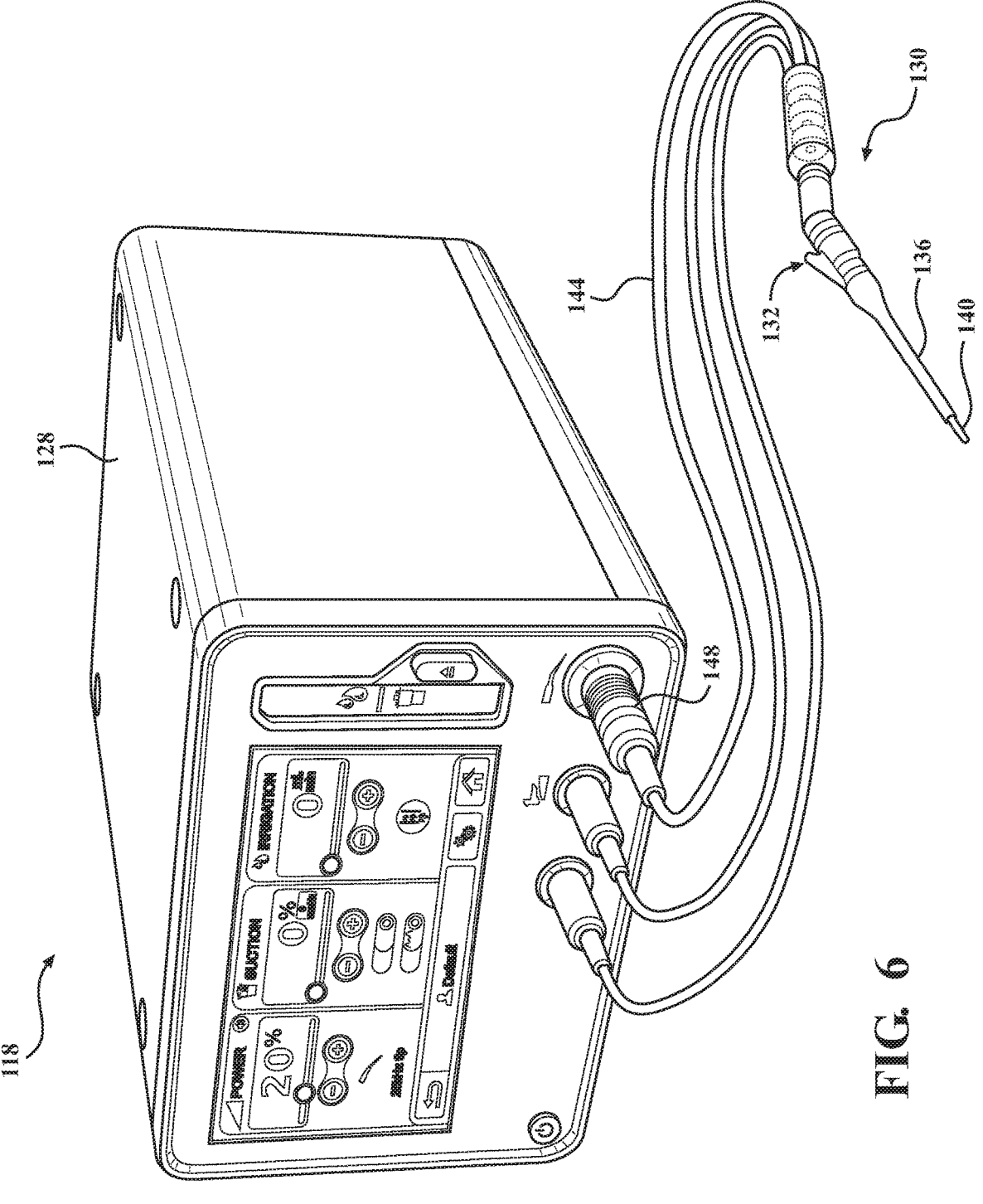
FIG. 6 depicts an ultrasonic surgical system of a neurosurgical system according to the teachings of the present disclosure.

With reference to FIG. 6, the ultrasonic handpiece assembly 130 may comprise an ultrasonic handpiece 132 comprising a proximal end and distal end. The ultrasonic handpiece assembly 130 may further comprise sleeve 136 and an ultrasonic tip 140 that may be coupled to the distal end of the ultrasonic handpiece 132. The sleeve 136 may be configured to provide irrigation to the ultrasonic tip 140 and/or the surgical site. It is further contemplated that the sleeve 136 may also be configured to provide aspiration to the ultrasonic tip 140. The ultrasonic tip 140 may comprise a cutting feature that is configured to ablate, cut, shape, and/or remove biological tissue. The ultrasonic handpiece assembly 130 may have various features, as described in U.S. Pat. Nos. 6,497,715 B2; 6,955,680 B2; and 6,984,220 B2 and PCT Publication WO 2020/068756 A1; which are hereby incorporated herein by reference in their entirety.

The ultrasonic handpiece assembly 130 may also comprise a cable 144 or other power cord comprising a power connector 148 or adapter configured to couple the ultrasonic handpiece assembly 130 to a power supply, such as the ultrasonic control console 128 configured to regulate the various aspects of the ultrasonic handpiece assembly 130. The ultrasonic control console 128 may also be configured to provide irrigation and/or aspiration via one or more tubes (not shown) connected to the handpiece assembly 130 and regulate the irrigation and/or aspiration functions of the ultrasonic handpiece assembly 130 to optimize performance of the ultrasonic handpiece assembly 130. An example of ultrasonic surgical systems that may be used are commercially available from Stryker including Sonopet IQ Ultrasonic Aspirator. The ultrasonic control console 128 may control various operation parameters based on signals received from the tissue detection system 116.

Figure 7:
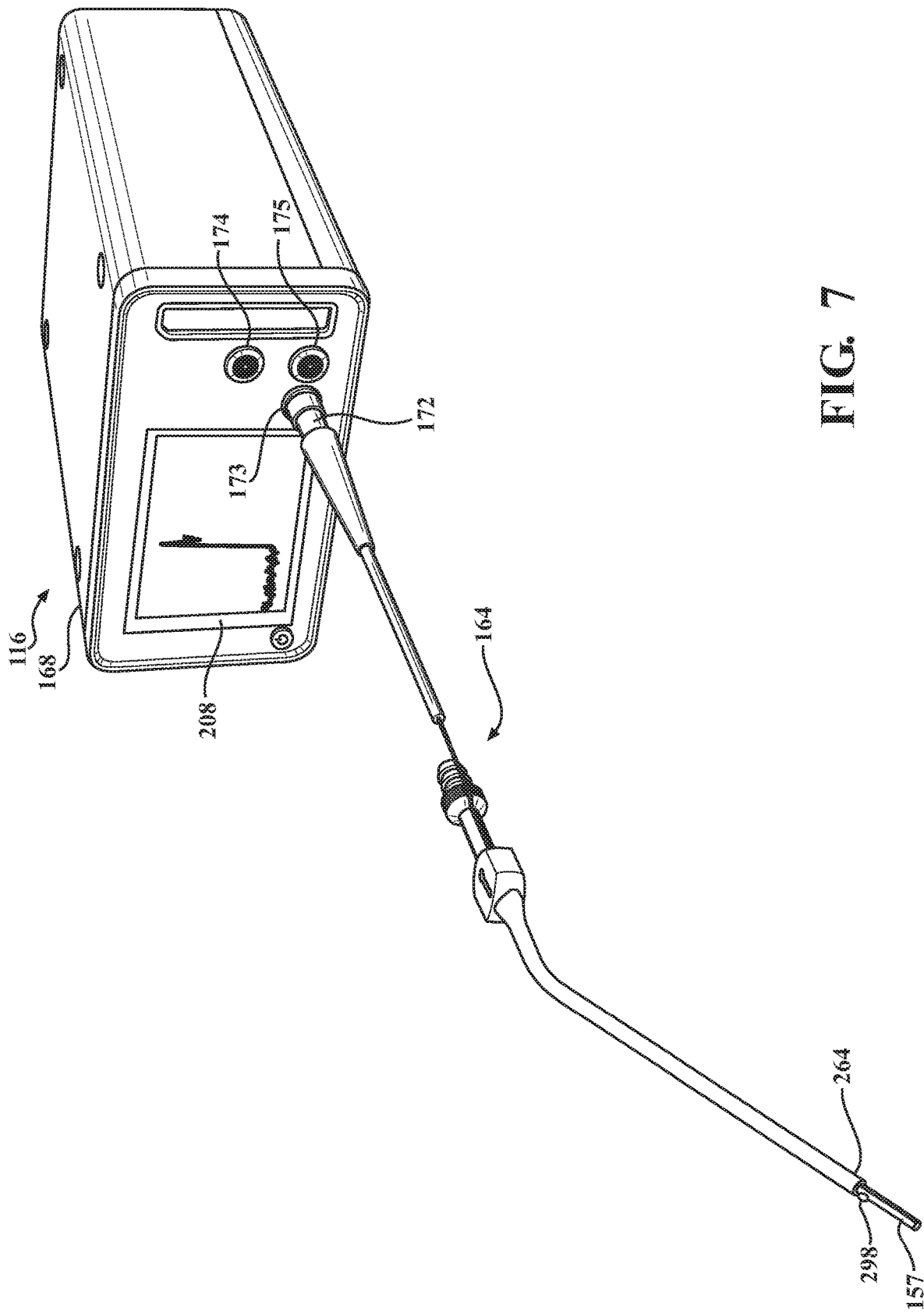
FIG. 7 depicts a tissue detection system of a neurosurgical system according to the teachings of the present disclosure.
Figure 8:
FIG. 8 depicts a functional block diagram of a tissue detection system of a neurosurgical system according to the teachings of the present disclosure.

With reference to FIGS. 7 and 8, the tissue detection system 116 includes a sample element 164 and a control console 168. The sample element 164 is connected to the control console 168 via connector 172. The sample element 164 may include a detection fiber 264, an indicator element 296, and an electrode 266 as discussed in greater detail below. The control console 168 may include a controller 204, a user interface 208, a power supply 212, an optical system 215, a microcontroller 220, and a mapping module 265. The optical system 215 may include an optics block 216, a spectrometer 224, an excitation source 228, and an optical connector 229. The function of each component will be discussed in greater detail below.

The user interface 208 may include a display for displaying output from the controller 204. The user interface 208 may also include one or more inputs (e.g., a push button, a touch button, a switch, etc.) configured for engagement by the healthcare professional. The power supply 212 may supply power to various components of the control console 168. The control console 168 may include a probe port 173 in which the connector 172 of the sample element 164 is connected. The detection fiber 264 may then be connected to the optics block 216 via the optical connector 229. The control console 168 may also include an electrical port 174 for establishing communication link to the surgical system 112 and the ultrasonic surgical system 118. The control console 168 may also include an indicator port 175 for connection to an indicator element 164, as will be discussed in greater detail below.

The mapping module 265 may include a device configured to generate stimulation signals for an electrode 266 that is configured to deliver the stimulation signals to the brain tissue 111. During surgical resection of the target tissue, the healthcare professional may need to map the brain tissue 111 in order to determine which areas of the brain tissue 111 correspond to functionally important areas. For example, functionally important areas of the brain that are responsible for speech or motor skills may be chosen to be avoided even when it is determined that these areas include target tissue if the target tissue cannot be removed without impacting the underlying function of the area. The device may be configured to generate an electric current which is then applied to the brain tissue 111 by the healthcare professional via an electrode. The electrode may be a standalone electrode disposed or coupled to an outer surface of the sample element 164 or the electrode may be integrated within the sample element 164, as discussed in greater detail below. The mapping module 265 and/or electrode 266 may have various functions and features as described in International Publication No. WO2021074265A1 and U.S. Pat. No. 7,150,737 B2 which are hereby incorporated by reference in their entirety. The controller 204 may be configured to generate an alert based on the results of the stimulation of the electrode 266 on the brain tissue 111. For example, the controller 204 may generate an alert to be displayed on the user interface 208, the display 120, or the display 121. The alert may indicate to the healthcare professional whether or not the brain tissue 111 corresponds to a functionally important area such as an area associated with motor function or speech function.

The excitation source 228 may illuminate the target tissue with excitation light via the detection fiber 264. The excitation source 228 may be configured to emit the excitation light (e.g., blue light at about 405 nm or blue light in the range of 400 nm to 500 nm). The excitation source 228 may also be configured to emit excitation light corresponding to other wavelengths such as wavelengths associated with the rest of the visible light spectrum other than blue light (e.g., greater than 500 nm but less than 700 nm), wavelengths associated with ultraviolet light spectrum (less than 400 nm) and/or infrared light spectrum (greater than 700 nm). The excitation source 228 may include any number of light sources such as a light emitting diode (LED), a pulsed laser, a continuous wave laser, a modulated laser, a filtered white light source, etc.

In certain instances, the excitation source may be further configured to emit excitation light corresponding to different wavelengths than described above. In this implementation, the excitation sources may be referred to as a first excitation source 228 and a second excitation source, with the first excitation source 228 being configured to emit a first excitation light at the predetermined wavelength of the visible light spectrum and the second excitation source configured to emit infrared light at a second wavelength range corresponding to the infrared light spectrum (e.g., 700 nm to 1 mm). When two excitation sources are present, the first excitation source 228 may be configured to emit light which would excite a first fluorophore such as PPIX, while the second excitation source is configured to emit light which would excite a second fluorophore such as ICG.

The controller 204 may control operation of the excitation source 228. The controller 204 may control operation of the excitation source 228 by varying operating parameters of the excitation source 228. The operating parameters may correspond to a time setting, a power setting, or another suitable setting. The time setting may include a pulse width. The pulse width may be based on the integration time of the spectrometer 224. The integration time of the spectrometer 224 is discussed in greater detail below.

The detection fiber 264 may be coupled to the optical connector 229. When the sample element 164 is coupled to the surgical tool (i.e., the ultrasonic handpiece assembly 130, the suction tool 156, or the bipolar forceps 160) the distal end 272 of the detection fiber 254 is adjacent to the working portion of the surgical tool and allows for excitation light to be delivered to the target tissue.

Figures 9A, 9B:
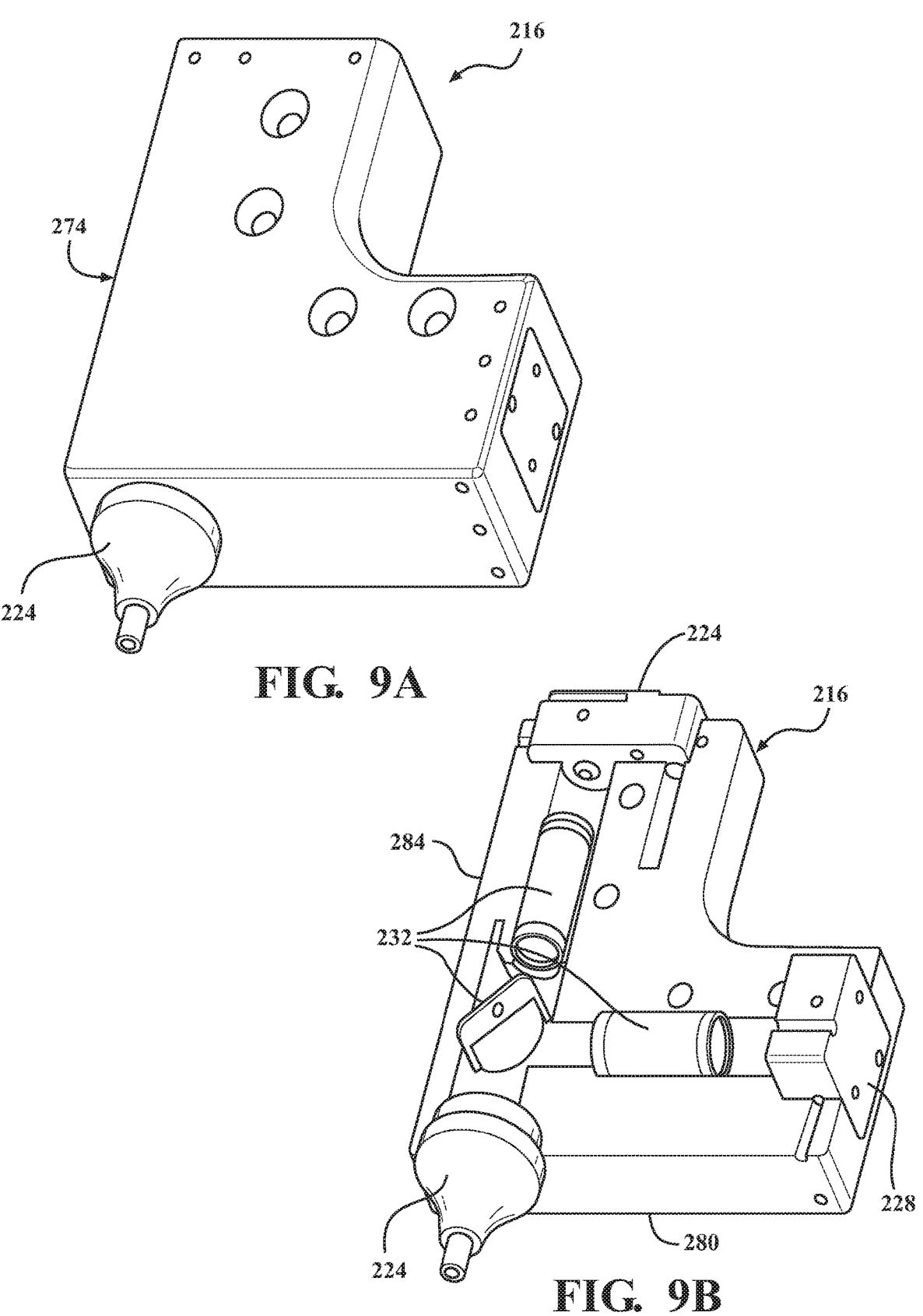
FIGS. 9A and 9B depict an optical system of a tissue detection system according to the teachings of the present disclosure.

With reference to FIGS. 9A and 9B, the optics block 216 is shown. The optical connector 229 may be coupled to the optics block 216. The optics block 216 may include an outer casing 274 constructed of metal or another suitable material and may fully enclose components 232 of the optics block 216. FIG. 7B shows the optics block 216 with the top of the casing removed such that the components 232 of the optics block 216 are visible. The optics block 216 may be L-shaped and include a first portion 280 and a second portion 284. The excitation source 228 may be coupled to the first portion 280 of the optics block 216. The spectrometer 224 may be coupled to the second portion 284 of the optics block 216.

Figure 10A:
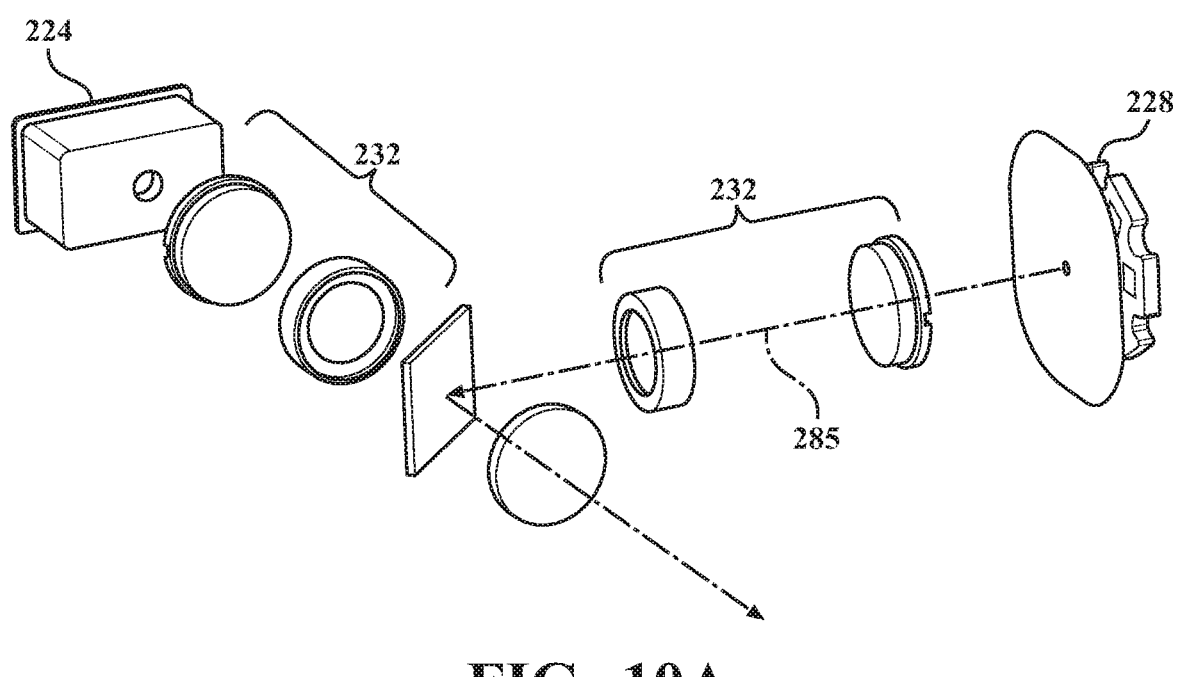
FIGS. 10A and 10B depict an exploded view of some components of the optical system of a tissue detection system according to the teachings of the present disclosure.
Figure 10B:
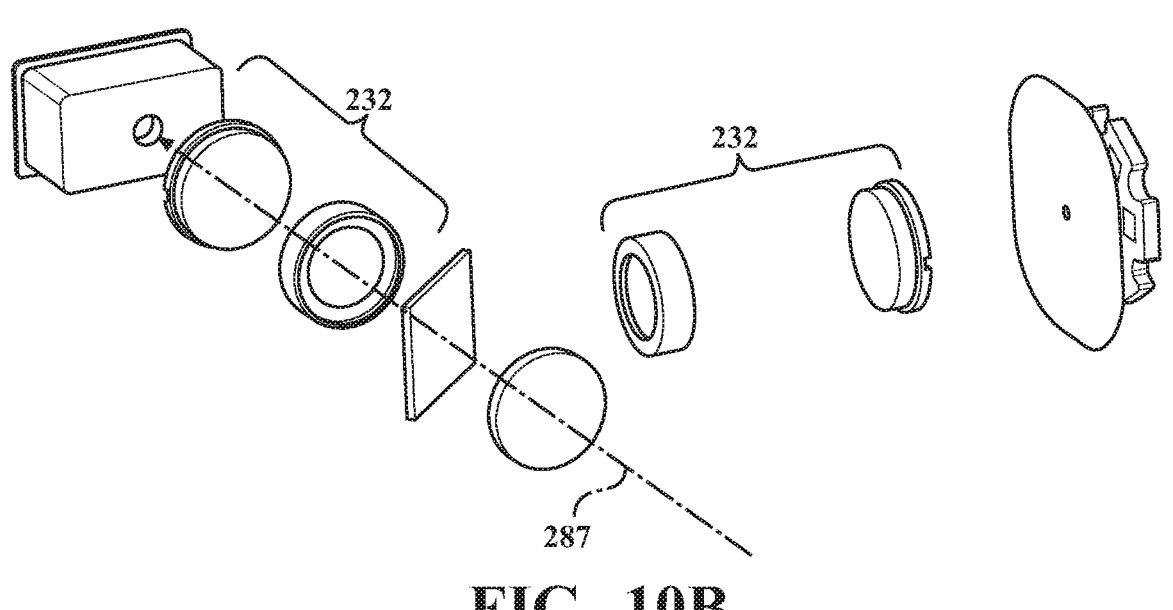

With additional reference to FIGS. 10A and 10B, an exploded view of the components 232 of the optical system 215 is shown illustrating an optical path 285 for the excitation light and the optical path 287 for light collected from the brain tissue 111. The first portion 280 may include the optical path 285 for the excitation light to travel from the one or more excitation sources 228 to the brain tissue 111 via the detection fiber 264. The optical path 285 may be defined by the components 232 in the first portion 280 of the optical block. The second portion 284 may include the optical path 287 for the collected light to travel from the brain tissue 111 via the detection fiber 264 to the spectrometer 224. The optical path 287 may be defined by the components 232 in the second portion 284 of the optical block. The components 232 of the optical block may optical components such as one or more laser line filters and one or more long-pass filters. The optics block 216 may include other optical components such as one or more mirrors, lenses, optical connectors, optical fiber, and/or any other suitable optical components.

In FIG. 10A, the excitation source 228 emits the excitation light which travels through one or more components 232, such as a laser line filter and/or long pass filter. The laser line filter or bandpass filter may be configured to reject unwanted noise (e.g., lower level transitions, plasma, and glows) generated by the excitation source 228. Stated differently, the laser line filter may be configured to clean up the excitation light or make the excitation light more monochromatic. The long-pass filter may be configured to reflect the light down the detection fiber 264 and to the brain tissue 111. The excitation source 228 may be configured to deliver unfiltered excitation light (i.e., the filters may be omitted) via the detection fiber 264 to the target tissue. The detection fiber 264 may guide the excitation light to the brain tissue 111 via the sample element 164.

The detection fiber 264 may be configured to collect light (i.e., fluorescence and ambient light) from the brain tissue 111. The coupling of the sample element 164 to the surgical tool results in the distal end 272 being adjacent to the working portion of the surgical tool as to allow for the light to be collected from the target tissue.

Due to the presence of ambient light and/or background light caused by various sources in the operating room such as the surgical microscope 108, surgical lamps, or any other devices in the operating room, the light collected from the brain tissue 111 may include the ambient light and/or background light. With reference to FIG. 10B, the light collected by the detection fiber 264 passes through the components 232, such as the long pass filter, of the second portion 284 of the optics block 216. After the light passes through the components 232, the light may enter the spectrometer 224 which is coupled to the optics block 216.

The detection fiber 264 may be coupled to the optical connector 229. As discussed in greater detail below, the distal end 272 of the detection fiber 264 may include a lens or other transparent material such that when the sample element 164 is positioned on a surgical tool (i.e., the ultrasonic handpiece, the suction tool or the bipolar forceps) the coupling of the sample element 164 to the surgical tool results in the distal end 272 of the detection fiber 264 being adjacent to the working portion of the surgical tool as to allow for the excitation light to be delivered to the target tissue.

Figure 11:
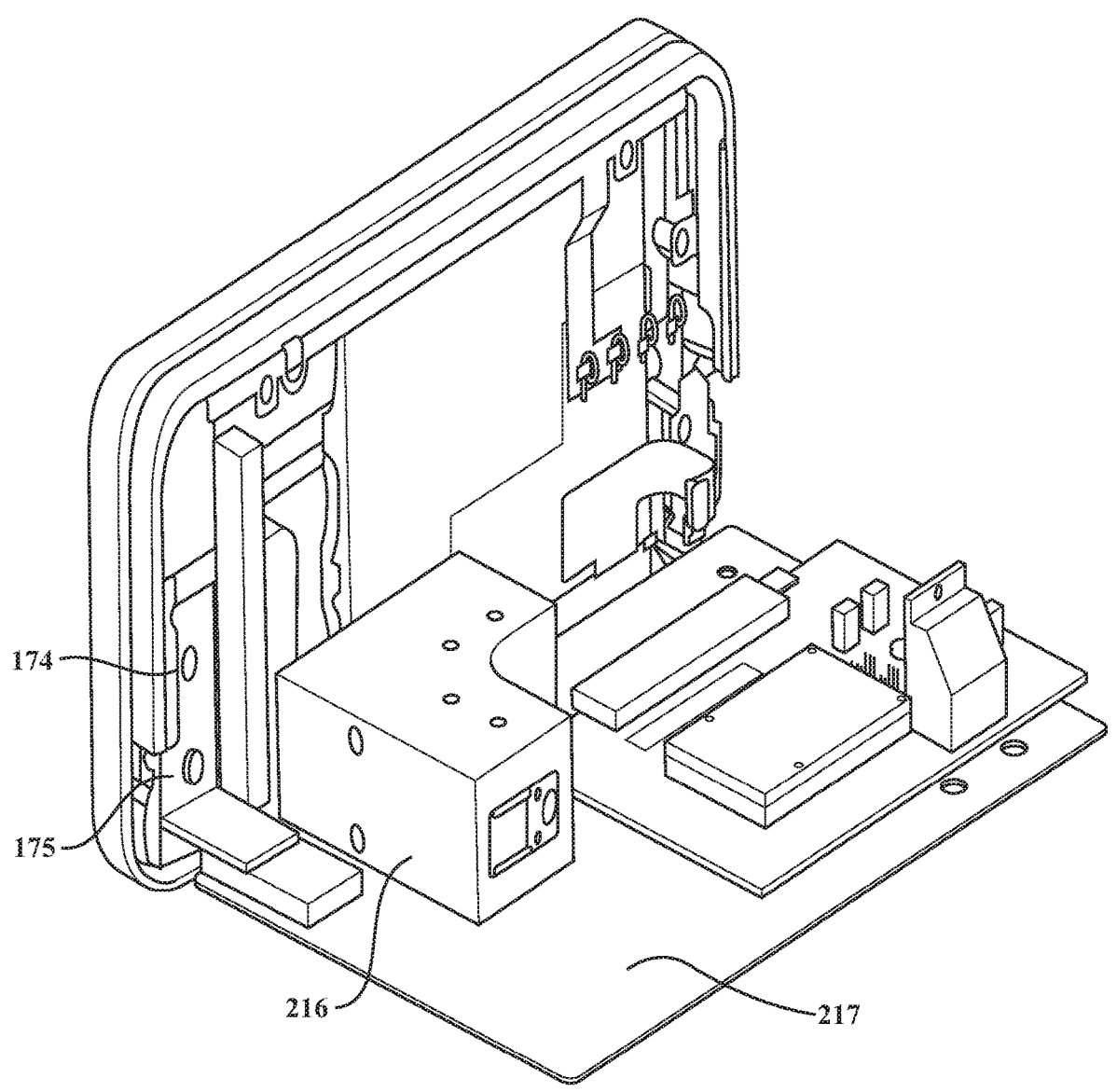
FIG. 11 depicts a view of an interior portion of a control console of a tissue detection system according to the teachings of the present disclosure.

With reference to FIG. 11, a view of the control console 168 with the outer casing removed is shown. The optics block 216 may be fixed (e.g., via bolts) directly to a base 217 of the control console 168 to allow for heat dissipation for heat generated by one or more components of the optical system 215. The control console 168 may include enough void space such that more than one optics block 216 may be stacked inside the control console 168. For example, a second optics block with various optical components inside may be stacked on top of the optics block 216. The second excitation source may be coupled to the second optics block. The second optics block may include components that define an optical path for light generated by the second excitation source to reach the target tissue.

Figure 12A:
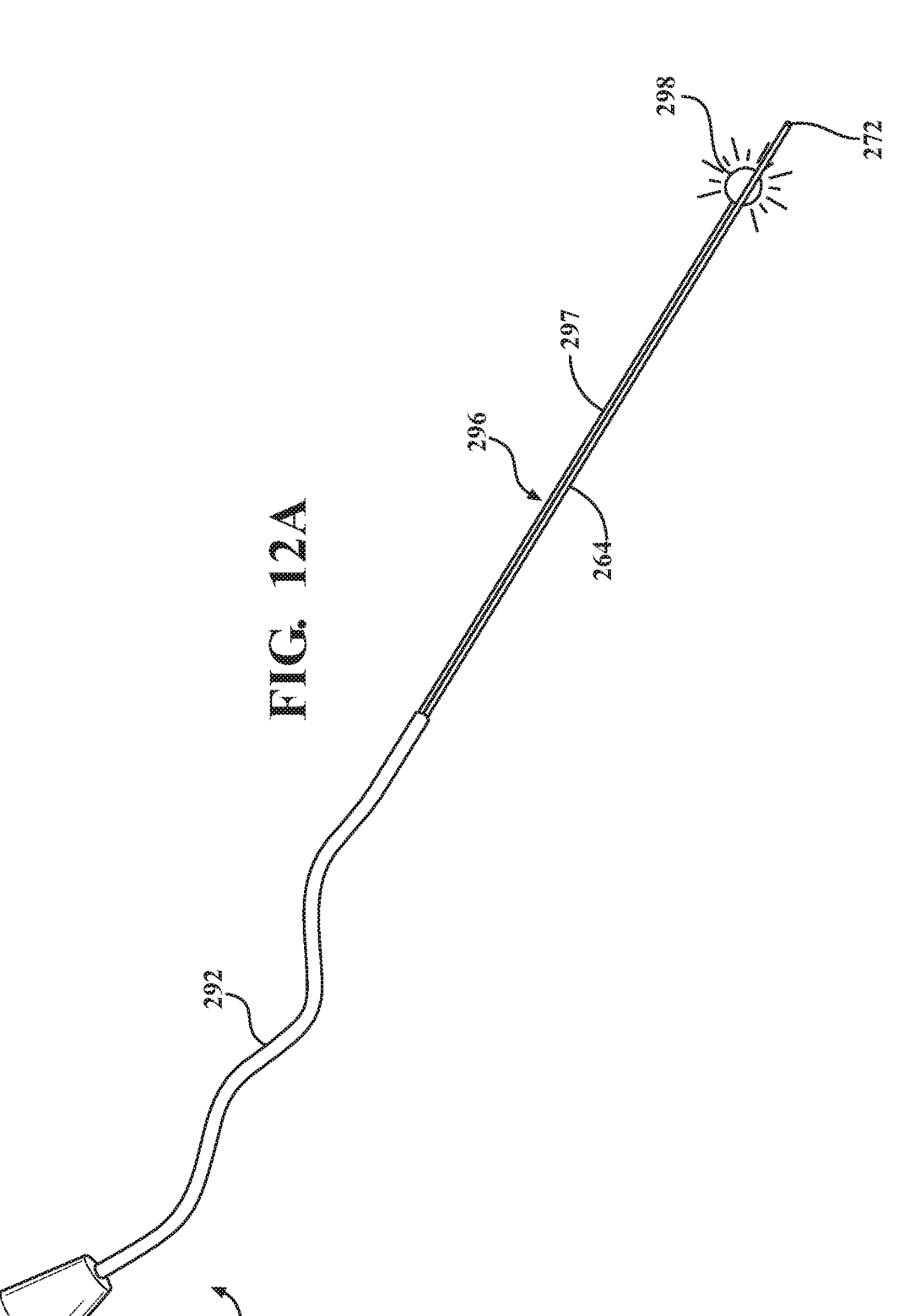
FIGS. 12A-E depict a sample element of a tissue detection system according to the teachings of the present disclosure.

With reference to FIG. 12A, the sample element 164 shown. The sample element 164 may also include an indicator element 296. The indicator element 296 may include a transmission member 297 connected to an indicator 298. The indicator 298 may include one or more light emitting diodes or another suitable light source. The indicator 298 is configured to emit light in response to detection of tumorous or target tissue by the controller 204. The indicator 298 may be sphere shaped, dome shaped, cylinder shaped, or another suitable shape. A jacket 292 may enclose part of the detection fiber 264 and part of the indicator element 296, specifically the transmission member 297. Stated differently, the jacket 292 may terminate well in advance of the distal end 272 of the detection fiber 264 leaving the transmission element 297, the indicator 298 and the detection fiber 264 at least partially exposed. The jacket 292 may be made from any one of polyvinyl chloride, polyethylene, chlorinated polyethylene, and chlorosulfonated polyethylene/neoprene or another suitable material. The electrode 266 although not shown in FIG. 12A may be integrated with the sample element 164. For example, a distal end of the electrode may be positioned adjacent to a distal end of the detection fiber 264 so that the distal end of the electrode 266 may contact the brain tissue 111.

As previously discussed, the detection fiber 264 may carry the excitation light from the optical system 215 to the brain tissue 111 and the detection fiber 264 may also collect light from the brain tissue 111 and deliver the light to the optical system 215 which in turn provides filtered optical signals to the spectrometer 224.

The sample element 164 may be coupled to any surgical tool (i.e., the ultrasonic handpiece assembly 130, the suction tool 156 or the bipolar forceps 160) such that the distal end 272 of the detection fiber 264 is proximal to the working portion of the surgical tool. The distal end 272 of the detection fiber 264 may include a lens, a collimator, or another suitable optical component that allows the detection fiber 264 to deliver excitation light to the brain tissue 111 and the detection fiber 264 to collect light from the brain tissue 111.

While the example is provided that the detection fiber 264 functions to deliver excitation light to the tissue and also collect light from the tissue, the system may include two separate fibers such as a collection fiber and an excitation fiber instead. The collection fiber may collect light from the tissue and the excitation fiber may deliver excitation light to the tissue. While the detection fiber 264 and any other fibers discussed herewith are contemplated as single fibers for simplicity, it is understood that each of the fibers may include more than one fiber. For example, the detection fiber 264 may include a bundle of detection fibers all being connected in similar fashion to the single fiber connections discussed above. In another example, the detection fiber 264 may include any number of fibers connected in series.

Figure 12B:
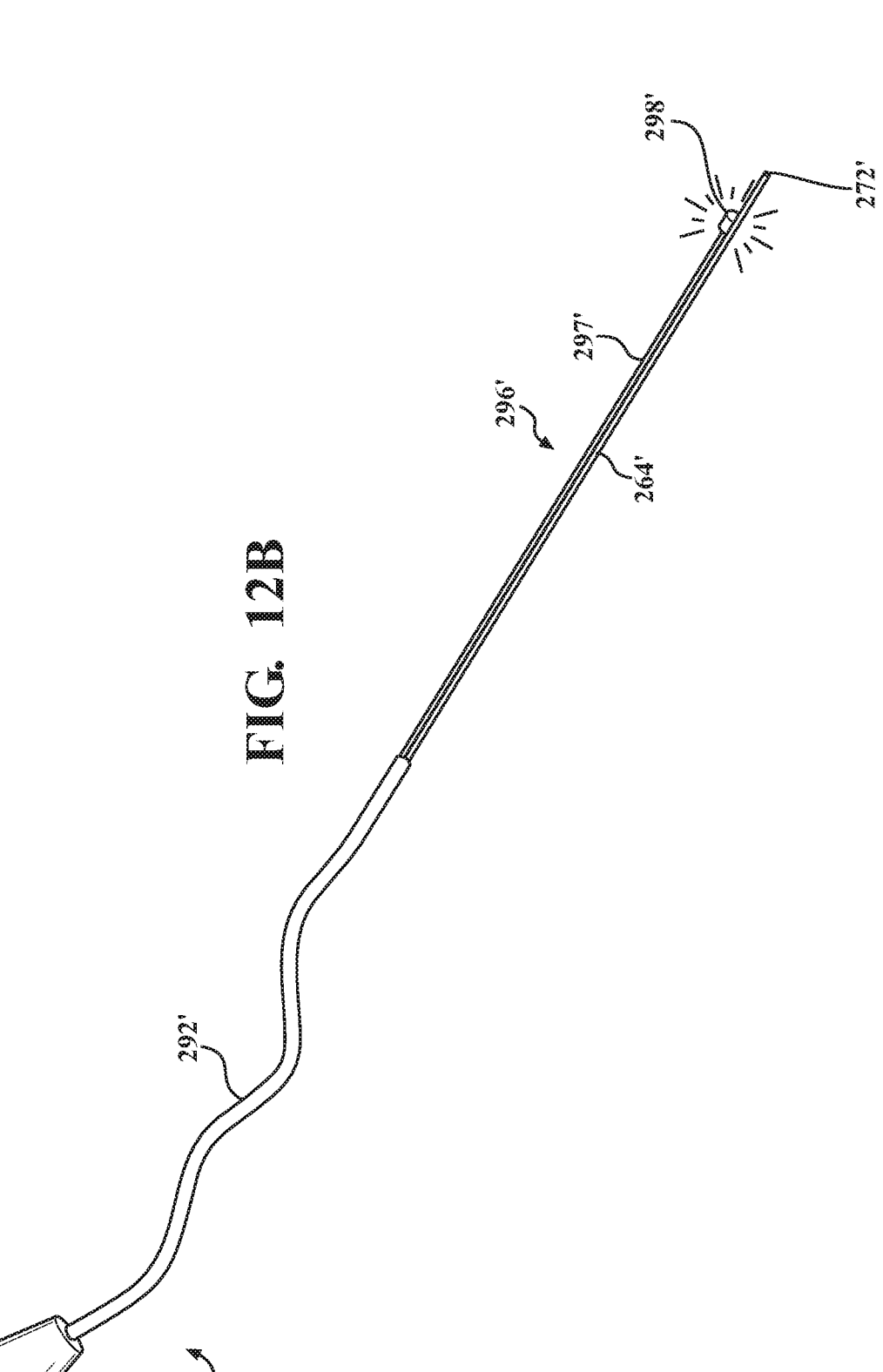

With reference to FIG. 12B, a second alternative configuration of the sample element 164 is shown. The sample element 164' shown is functionally equivalent to the sample element 164 shown in FIG. 12A so a detailed discussion of the functionally of equivalent parts, is hereby omitted. The indicator 298' shown is cylinder shaped as opposed to the sphered shaped indicator 298 shown in FIG. 12A.

Figures 12C, 12D:
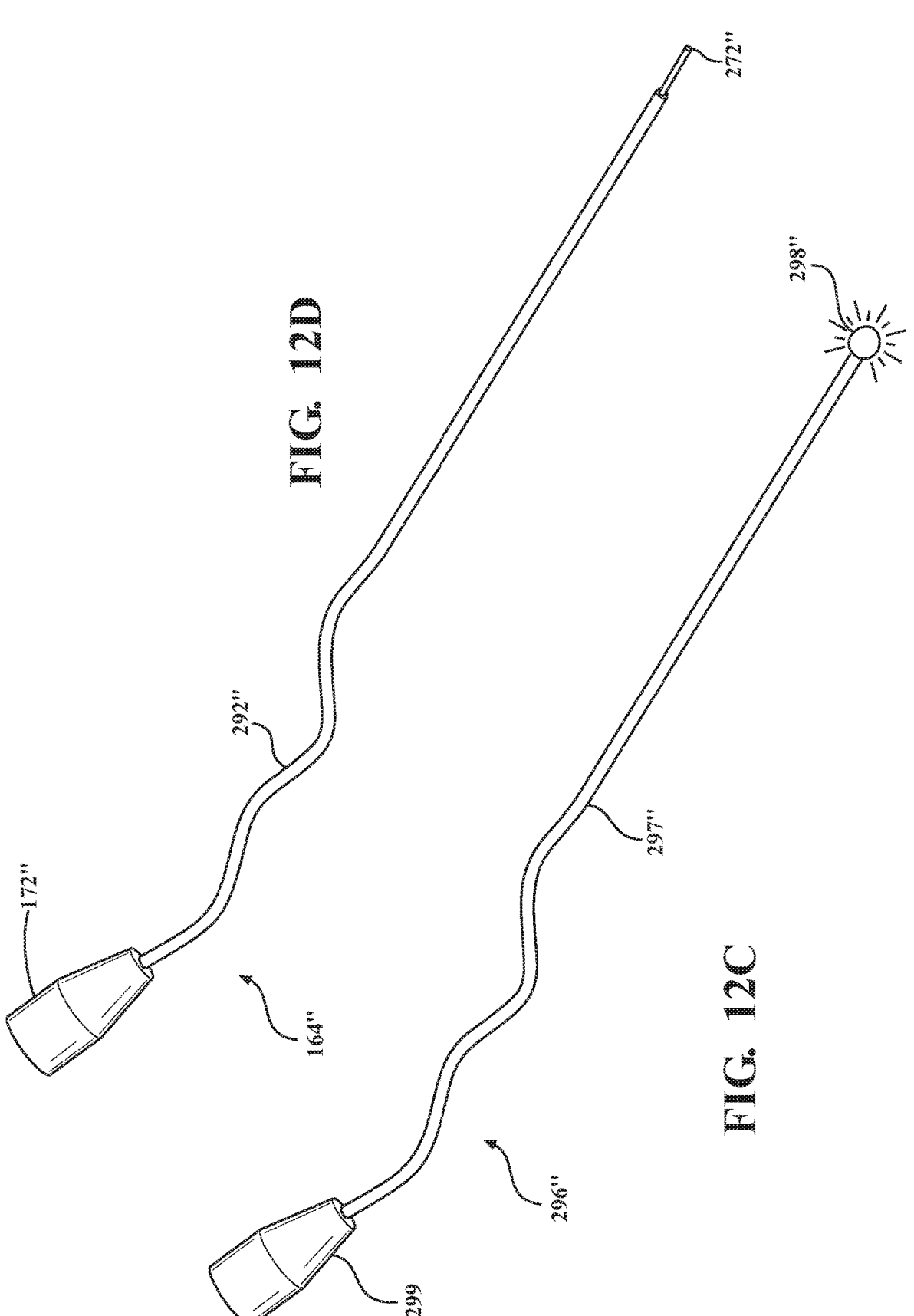
Figure 12E:
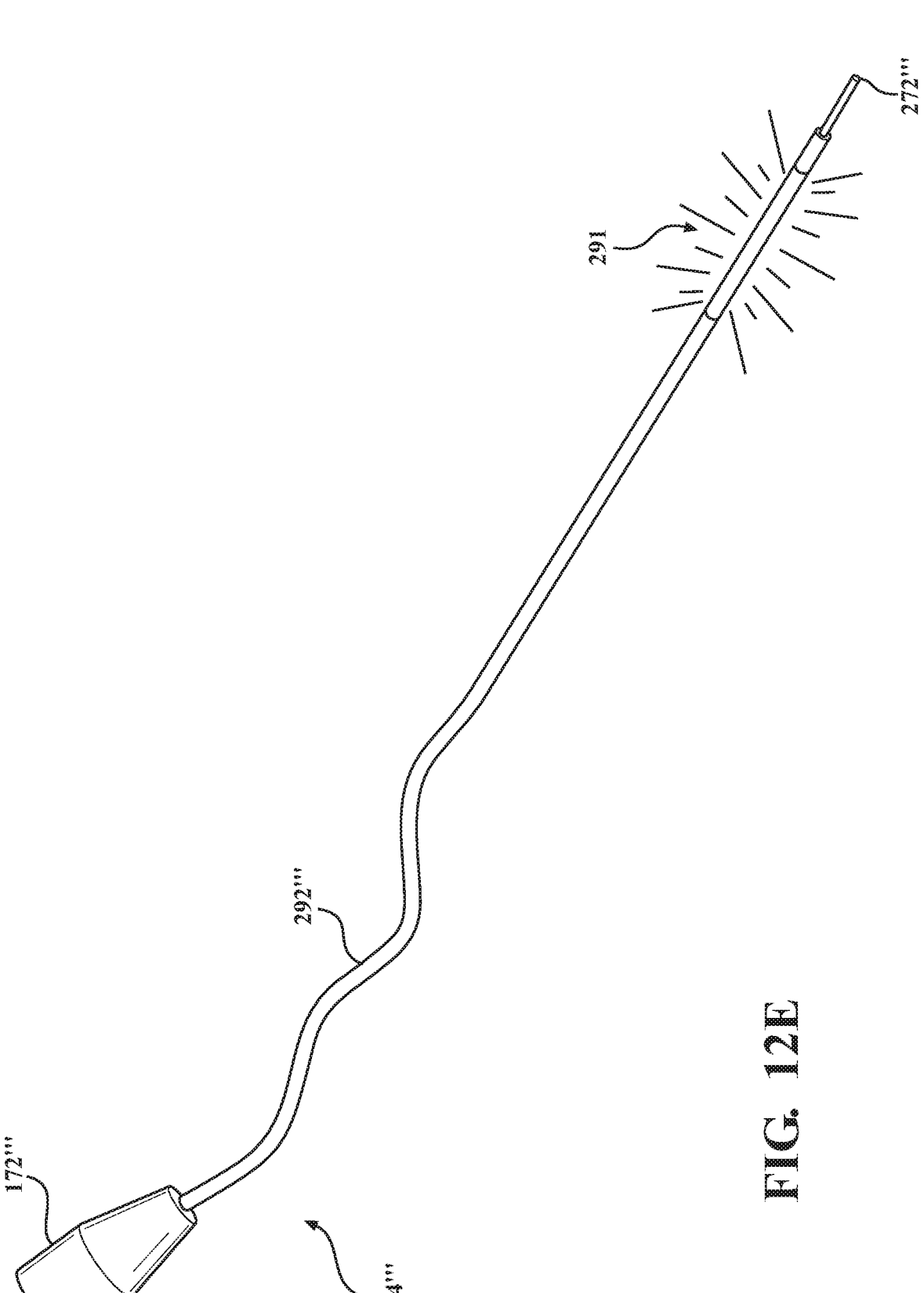

With reference to FIG. 12D, a third configuration for the sample element 164 is shown. The sample element 164" shown is functionally equivalent to the sample elements 164 and 164' shown in FIGS. 12A and 12B so a detailed discussion of the functionally of equivalent parts, is hereby omitted. In this configuration, the indicator element 296' is provided separate from the sample element 164' (i.e., the indicator element 296 is not integrated with the sample element 164'). The indicator element 296—may include a transmission member 297', such as a wire and/or a cable covered by a jacket, an indicator 298, and a connector 299 for connecting the transmission member 297 to the indicator port 175 of the control console 168. The indicator element 296 may include a connector 299 for connecting the indicator element 296 to the indicator port 175 of the control console 168.

With reference to FIG. 12D, a fourth configuration for the sample element 164 is shown. The sample element 164— shown is functionally equivalent to the sample elements 164, 164', and 164" shown in FIGS. 12A and 12B so a detailed discussion of the functionally of equivalent parts, is hereby omitted. Here, the transmission member 297'—of the indicator element 296''' and the indicator 298 may be replaced with an optical fiber hereinafter referred to as an indicator fiber. The indicator fiber serves to emit light in response to detection of target tissue by the controller 204. The sample element 264''' may also include an indicator portion 291 which is illuminated by the indicator fiber as light travels down the sample element 264'''. The indicator portion 291 may be situated proximal to the distal portion of the sample element 164 to ensure that the healthcare professional is able to view the indicator portion 291 as the healthcare professional is resecting tissue. The indicator portion 291 may be transparent or may also correspond to a removed portion of the jacket 292 of the sample element 164. The indicator fiber may be coupled to the optics block 216 via the optical connector and receive light from the excitation source 228 or another excitation source at a different wavelength than the excitation light. For example, the excitation source may generate green light (e.g., wavelengths of about 520-564 nm) when instructed by the controller 204 to indicate the detection of the target tissue.

The sample element 164''' may include a co-axial fiber with a central core and an outer channel covered by the jacket 292. The detection fiber 264—may be disposed within the central core while the indicator fiber is disposed within the outer channel. A portion of the jacket 292 of the sample element 164'''' may be removed such that the indicator fiber may illuminate light through the sidewalls of the outer channel to light up the indicator portion 291.

The controller 204 may transmit an activation signal to the indicator 298 in response to the detection of the target tissue. The indicator 298 may emit light in response to receiving the activating signal. The controller 204 may control the LED to emit various colors of light depending on whether the controller 204 detects PPIX or ICG (i.e., whether the brain tissue 111 corresponds to the target tissue or a blood vessel). For example, the controller 204 may control the LED to emit green light (e.g., wavelengths of about 520-564 nm) when PPIX above a threshold is detected or yellow light (e.g., wavelengths 565-590 nm) when ICG is detected.

The spectrometer 224 is configured to convert the filtered optical signals (i.e., filtered light) into spectral signals in the form of electrical signals. The microcontroller 220 is configured to control operation of the spectrometer 224. Examples of spectrometer systems that may be used are commercially available from Hamamatsu including Mini-spectrometer micro series C12880MA. Although a spectrometer 224 is contemplated throughout the disclosure, other optical instruments may be used instead of a spectrometer 224. The spectrometer 224 may include an entrance slit, a collimating lens/mirror, transmission grating element, a focusing mirror, and an image sensor. The entrance slit may receive the collected light from the optics block 216 which then passes through the collimating lens/mirror. The collimating lens/mirror collimates the collected light passed through the entrance slit and guides it onto the grating element. The grating element separates the incident light from the collimating lens into different wavelengths and lets the light at each wavelength pass through or reflect away at a different diffraction angle. The focusing lens or mirror forms an image of the light dispersed into wavelengths by the grating element onto linearly arranged pixels of the image sensor according to wavelength.

Each wavelength is photoelectrically converted into an electrical signal (i.e., a spectral signal). The image sensor outputs the signal of light incident on each pixel at a certain time interval (i.e., the image sensor converts the optical signals into electrical signals and outputs them). The time interval may be referred to as the integration timing. The microcontroller 220 may be configured to control operation of the spectrometer 224, for example, the integration timing based on instructions from the controller 204. The microcontroller 220 forwards the spectral signals via a communication interface (e.g., serial peripheral interface (SPI)) to the controller 204.

The controller 204 is configured to transform the spectral signals provided by the microcontroller 220 into simple/usable output variables via in real-time in order to provide the healthcare professional with an indication of presence of the target tissue within the sterile fields. The controller 204 may illuminate the indicator 298 of the sample element 164 in response to detecting the target tissue.

Since ambient light may be present in the optical signals collected at the target tissue and thus present in the spectral signals provided by spectrometer 224, the controller 204 is configured to perform one or more functions or methods of control to remove the ambient light from the spectral signals (i.e., the wavelengths associated with the ambient light) to accurately detect when the brain tissue 111 corresponds to the target tissue as evidence by the PPIX present in the target tissue.

The controller 204 may be configured to remove the ambient light from the spectral signals using any suitable method, function, or algorithm in in any suitable manner. In one example, the controller 204 may pulse the one or more excitation source 228. The controller 204 may be configured to pulse the excitation source 228 such that alternating spectral signals are collected. During a first period, the controller 204 may operate the excitation source 228 in a first illumination state (IS1) where the excitation source 228 is ON and illumining the target tissue via the detection fiber 264. During a second period of time, the controller 204 may be configured to operate the excitation source 228 in a second illumination state (IS2), where the excitation source 228 is OFF and not illuminating the target tissue via the detection fiber 264.

Figure 13:
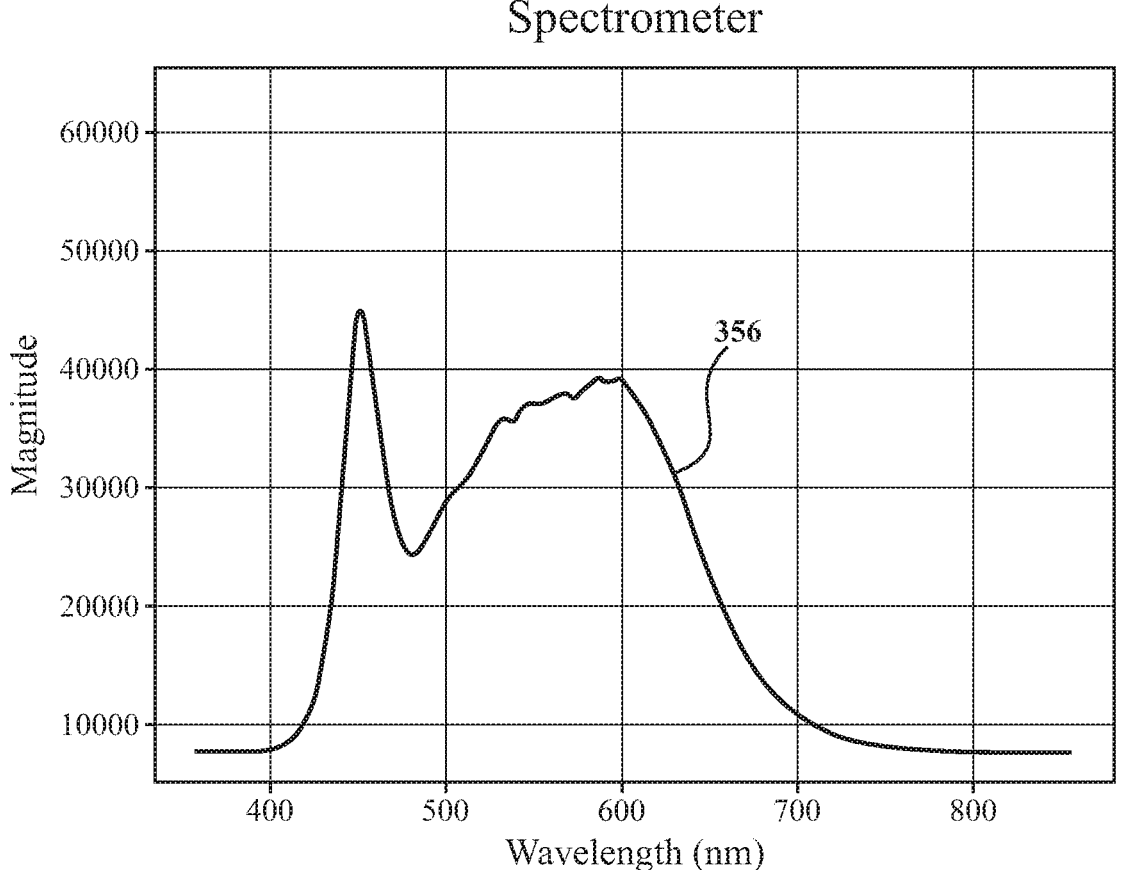
FIG. 13 depicts an excited spectral signal generated by a spectrometer of a tissue detection system according to the teachings of the present disclosure.

The spectral signals provided by the spectrometer 224 and generated as a result of the optical signals collected from the target tissue while the excitation source 228 is in the first illumination state (IS1) during the first period, should include the red fluorescence when the brain tissue 111 corresponds to the target tissue. The spectral signals received by the controller 204 during the first period of time while the excitation source 228 is in the first illumination state (IS1) may be referred to as excited spectral signals from this point forward. With reference to FIG. 13, an excited spectral signal 356 is shown corresponding to the red fluorescence collected during the first period of time. Due to the presence of ambient light and/or background light caused by various sources in the operating room such as the surgical microscope 108, surgical lamps, or any other devices in the operating room, the excited spectral signal 356 shows a wide range of wavelengths present in addition to the wavelengths associated with the red fluorescence. With reference to FIG. 8B, the light collected by the detection fiber 264 passes through the components 232, such as the long pass filter, of the second portion 284 of the optics block 216. After the light passes through the components 232, the light may enter the spectrometer 224 which is coupled to the optics block 216.

The spectral signals provided by the spectrometer 224 and generated as a result of the optical signals collected from the target tissue while the excitation source 228 is in the second illumination state (IS2), may contain ambient light and should not contain the red fluorescence generated by the target tissue even since the excitation light is required to be absorbed by the target in order for the tissue to emit the fluorescence. The spectral signals received by the controller 204 during the second period of time while the excitation source 228 is in the second illumination state (IS2) may be referred to as ambient spectral signals.

Figure 14A:
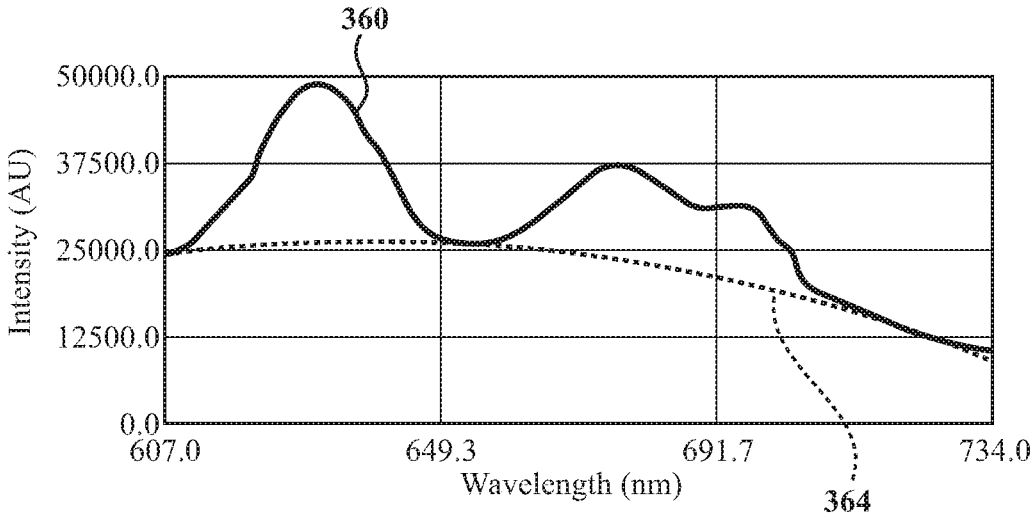
FIGS. 14A and 14B depict a first modified spectral signal and a second modified signal generated by a controller of a tissue detection system according to the teachings of the present disclosure.
Figure 14B:
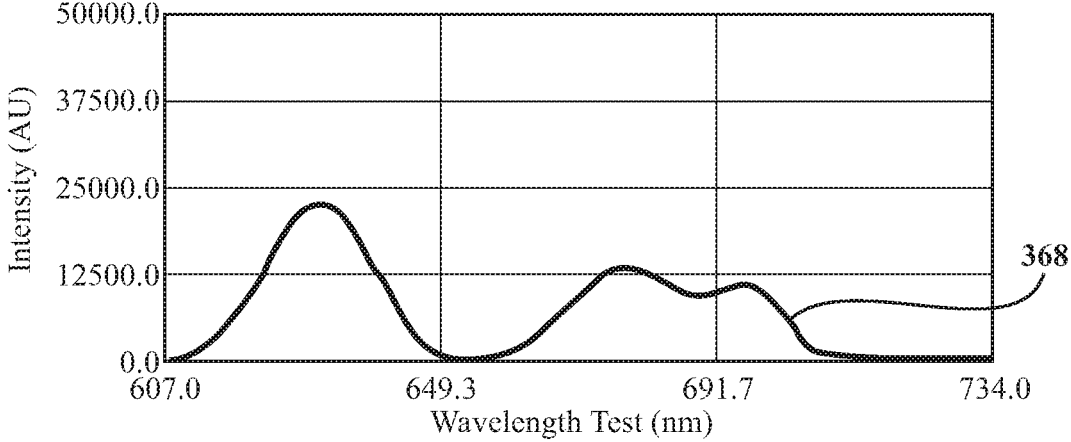

With reference to FIGS. 14A and 14B, a first modified spectral signal 360 and a second modified spectral signal 368 of the target tissue are shown. Fluorescence intensity is shown on one axis and emission wavelength is shown on the other axis. The controller 204 may be configured to generate the first modified spectral signal 360 in any suitable manner to remove ambient light (i.e., the ambient spectral signal) from consideration. For example, the controller 204 may be configured to subtract the ambient spectral signal from the excited spectral signal (i.e., subtract spectral signals provided over the second illumination state (IS2) from the spectral signals provided over the first illumination state (IS1)). After the first modified spectral signal 360 is generated, the controller 204 may be configured to further subtract any background signal still present from the first modified spectral signal 360.

The controller 204 may be configured to subtract any background signal still present in the first modified spectral signal to generate a second modified spectral signal. For example, the controller 204 may be configured to use an algorithm based on a polynomial, such as an automated polynomial fitting routine based on a modified version of least squares polynomial to obtain a baseline curve 364 representative of any background signal still present. The controller 204 using the algorithm may then subtract the baseline curve 364 from the first modified spectral signal 360 to obtain a second modified spectral signal 368 which is representative of the red fluorescence emitted from the target tissue with the ambient light and background light removed.

Figure 15:
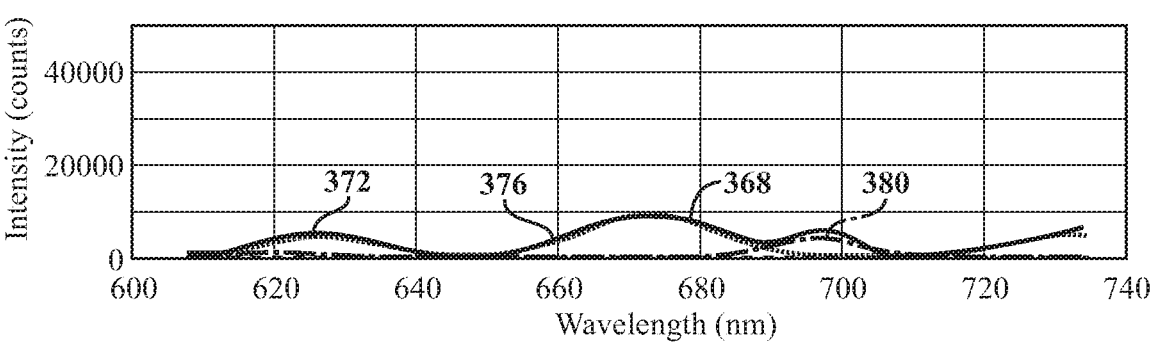
FIG. 15 depicts gaussian curves fit to a second modified signal generated by a controller of a tissue detection system according to the teachings of the present disclosure.

The controller 204 may be configured to fit at least one gaussian distribution/curve to the spectral signals. The controller 204 may fit the at least one gaussian distribution to raw spectral signal (i.e., the excited spectral signals and/or the ambient spectral signals), the first modified spectral signal, or to the second modified spectral signal. This may enable a level of confidence to be determined based on the results of the fitting. In FIG. 15, three gaussian curves (372, 376, 380) were fitted to the three remaining spectral bands of the second modified spectral signal 368 (i.e., the spectral signal remaining after the ambient light and the background light were removed).

Figure 16:
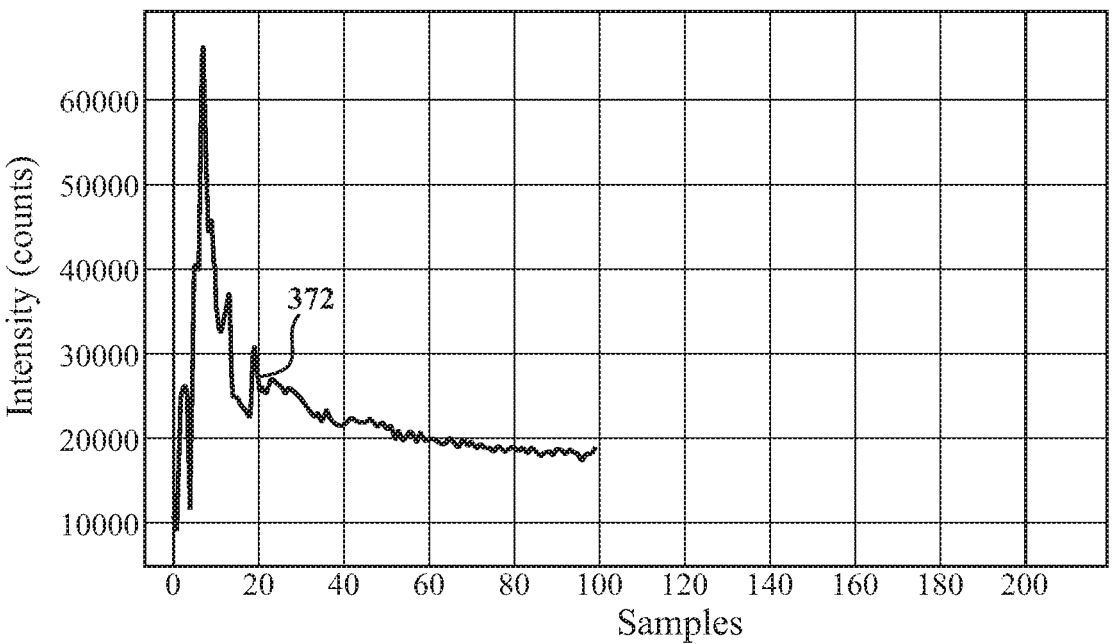
FIG. 16 depicts PPIX intensity generated by a controller of a tissue detection system according to the teachings of the present disclosure.

With reference to FIG. 16, the controller 204 may be configured to select the gaussian band that has been fitted to PPIX's emission band (i.e., a band including 635 nm) and generate the selected band 372 for display in real time such that the healthcare professional may view the PPIX intensity in real time as the sample element 164 collects the samples. The controller 204 may store a predetermined intensity threshold that has been associated with the target tissue.

The controller 204 may be configured to generate an activation signal based on a comparison of the PPIX intensity, for the PPIX emission band that was fitted to the gaussian band, to the predetermined intensity threshold. In response to the PPIX intensity exceeding the threshold, the controller 204 may generate an activation signal. Based on the activation signal, the indicator 298 of the sample element 164 may emit light thereby providing a real-time indication to the healthcare professional of the presence of target tissue.

The controller 204 may be configured to perform an error correction process prior to generating the activation signal. During the error correcting process, the controller 204 may be configured to determine a ratio of any of the spectral signals (raw spectral signal, the excited spectral signals, the ambient spectral signals, the first modified spectral signal, or the second modified spectral signal) to a gaussian band such as the gaussian band that has been fitted to the PPIX emission band. The controller 204 may be configured to calculate at least two full width at half maximum (FWHM) points for the gaussian band. The controller 204 may be configured to calculate how far the at least two FWHM points are from the any of the spectral signals (as a percentage of their intensity). When the ratio is above a threshold (e.g. 2 percent), the controller 204 may be configured to return that the PPIX intensity falls below the threshold and thus the controller 204 does not generate the activation signal even though the activation signal would have been generated prior to the error correction process being performed.

The controller 204 may communicate with the ultrasonic surgical console via a communication link established through the electrical port 174. For example, a cord may be plugged into the electrical port and also plugged into the ultrasonic control console 128 to establish the communication link. The communication link may also be established wirelessly. The controller 204 may inform the ultrasonic control console 128 based on a type of tissue detected. The controller 204 may inform the ultrasonic control console 128 when target tissue is present or absent. Based on the information provided from the controller 204, the ultrasonic control console 128 may adjust one or more operating parameters. For example, when target tissue is present, the resection rate may not be limited; however, when target tissue is not present, the resection rate may be limited such that the ultrasonic surgical handpiece is prevented from cutting the healthy tissue. In such an example, the ultrasonic console may control the drive signal, such as the voltage, current, or both supplied to the ultrasonic handpiece based on the whether the target tissue is detected. While the example is provided that the controller 204 may communicate with the ultrasonic control console 128, the controller 204 may alternatively communicate with the surgical control console 115 to control the various surgical tools (e.g., bipolar forceps 160, neuro stimulators, dissectors, ablation devices, etc.) based on the absence or presence of target tissue.

The controller 204 may be configured to perform one or more standardization routines and/or calibration routines. The controller 204 prompt the healthcare professional via the user interface 208 to perform the calibration routine at the beginning of the resection procedure to account for autofluorescence variations of brain tissue 111 from person to person. The controller 204 may instruct the healthcare professional to collect light from known healthy brain tissue 111 with the detection fiber 264 of the sample element 164 to use as a standard baseline. Based on the characteristics of the light collected, the controller 204 may adjust one or more parameters of an algorithm for determining whether brain tissue is tumorous or not such as the predetermined intensity threshold for PPIX.

In a standardization routine, during a first period of time, the controller 204 may instruct the healthcare professional to collect light from a light source (e.g., a nearby light) outputting light from a consistent spectral band with the detection fiber 264 of the sample element 164. After the optical system 215 has converted the light collected into an electrical signal (hereinafter, referred to as a first standardization electrical signal), the controller 204 may store the first standardization electrical signal representative of the characteristics of the light collected. During a second period of time occurring after the first period of time, the controller 204 may instruct the healthcare professional to collect light from the same light source. After the optical system 215 has converted the light collected into a second standardization signal, the controller 204 may compare the first standardization signal obtained during the first period of time to the second standardization signal obtained during the second period of time and use the results to account for any variations of the optical readings over time. For example, the controller 204 may adjust one or more parameters of an algorithm used to determine whether the brain tissue is tumorous or not or one or more settings of the spectrometer 224 to account for any variations of the optical readings over time.

Figure 17:
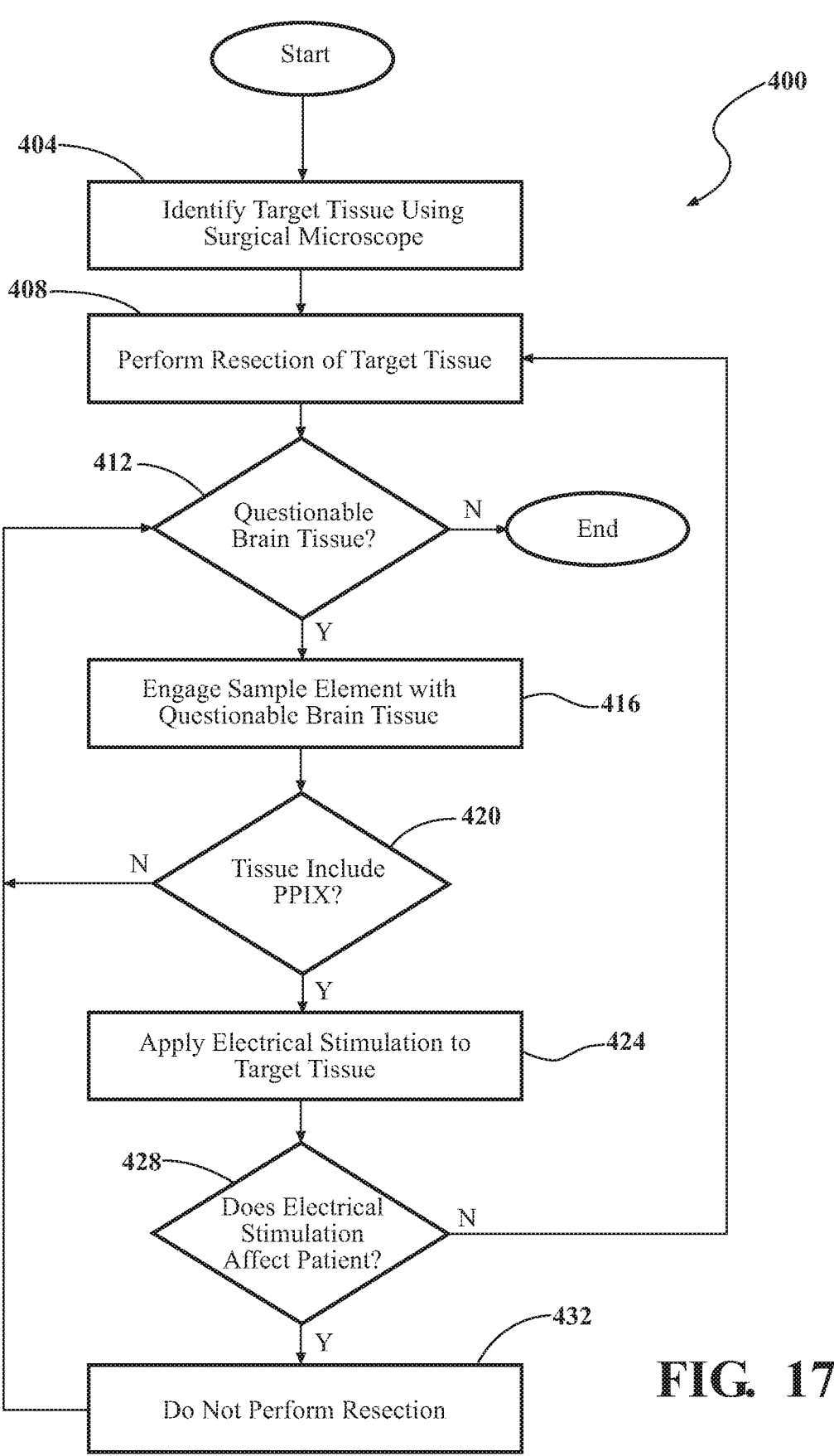
FIG. 17 depicts a flowchart for a surgical resection procedure performed with a neurosurgical system according to the teachings of the present disclosure.

FIG. 17 includes a flow chart 400 illustrating a surgical resection procedure in accordance with the teaching of the present disclosure. As will be appreciated from the subsequent description below, this flowchart merely represents an exemplary and non-limiting sequence of blocks to describe a typical resection procedure performed to resect target tissue and is in no way intended to serve as a complete functional block diagram of all of the steps of a resection procedure.

The resection procedure 400 begins at 404 where the healthcare professional may identify target tissue using the surgical microscope 108 under excitation light. At 408, after the target tissue has been identified, the healthcare professional may perform resection of the target tissue using one of the surgical tools described above. At 412, after resection of the target tissue identified via the surgical microscope, the healthcare professional determines whether there is any questionable brain tissue (e.g., tissue which does not emit visible light when viewed from the surgical microscope 108 under excitation but has characteristics associated with the target tissue) that may correspond to target tissue. If there is no questionable brain tissue, the resection procedure may end; otherwise, the resection procedure continues at 416.

At 416, the healthcare professional engages the sample element 164 with the questionable brain tissue (e.g., to excite the brain tissue and collect light from the brain tissue). At 420, the healthcare professional determines whether the tissue includes PPIX as evidenced by the indicator 298 of the sample element 164. If so, the resection procedure continues at 424; otherwise the resection procedure continues at back at 412. At 424, the healthcare professional applies electrical stimulation to the target tissue. At 428, the healthcare professional determines whether the electrical stimulation affected the patient. If so, the healthcare professional may choose not to perform resection of the target tissue; otherwise, the resection procedure continues back at 408.

With reference to FIGS. 18-21, the sample element 164 may be coupled to any surgical tool. The sample element 164 may be coupled to the ultrasonic handpiece assembly 130 as shown in FIGS. 18A and 18B, to the bipolar forceps 160 (or any surgical tool associated with the surgical system 112 such as dissector, etc.) as shown in FIGS. 19A and 19B, and the suction tool 156 as shown in FIGS. 20-22. The sample elements 164 and 164' and/or the indicator element 296 may be coupled to the surgical tools in any suitable manner. For example, the sample element 164 (or the sample element 164" and indicator element 296") may be coupled to the surgical tools via an adhesive. The adhesive may be in the form of a sticker or substance such as glue. Additionally or alternatively, the sample element 164 (or sample element 164" and indicator element 296") may also be coupled to the surgical tools via a fixation element discussed in greater detail with respect to FIG. 22 or a jacket discussed in greater detail with respect to FIGS. 21 and 22.

As shown in FIG. 18B, the sample element 164''' may be coupled to the ultrasonic handpiece assembly 130 in any manner as long as there is no direct contact between the tip 140 and distal portion of the sample element 164'''. For example, the sample element 164''' may terminate at a portion of the sleeve 136 proximal to the tip 140. In another example, the sample element 164''' may extend past the sleeve 136 but be arranged such that there is adequate empty space between the tip 140 and the sample element 164''' to prevent contact between the tip 140 and the sample element 164'''.

In the configuration shown in FIGS. 19A and 19B, the sample element 164" is shown coupled to an outer portion of a first pincer 302 the bipolar forceps 160 and the indicator element 296" is shown coupled to an inner portion of a second pincer 304 of the bipolar forceps 160. As shown the indicator is disposed near the tip of the second pincer such that the healthcare professional can view the indicator 298" while performing resection of the target tissue without having to look at another screen or portion of the tool.

With reference to FIGS. 20 and 21, the sample element 164 is shown coupled to the suction tool 156. The detection fiber 164 and a portion of the indicator element 296, (i.e., the transmission element 297 and indicator 298) may be guided through the through bore 171 of the handle 159. A distal end 272 of the detection fiber 264 may be positioned proximally to a distal end of the suction cannula 257. The indicator 298 may be positioned near the distal end of the detection fiber 264 but more proximal to a distal end 162 of the control portion 167 of the handle 159 than the distal end 272 of the detention fiber is. In other words, the distal end 162 of the detention fiber 264 may be disposed more proximal to the distal end of the suction cannula 157 than the indicator 298 is. With additional reference to FIG. 21, after the detection fiber 264 and the portion of the indicator element 296 is fed through the through bore 171, a jacket 306 may be fitted overtop of the suction cannula 157, the detection fiber 164, and the transmission element 297. The jacket 306 may be mated to the distal end 162 of the handle 159 so that the distal end 162 and the through bore 171 are covered. The jacket 306 may terminate just before where in the indicator 298 is coupled to the suction cannula 157. The detection fiber 264 may protrude from beneath the jacket 306 so that the jacket 306 does not interfere with the delivery of excitation light or collection of fluorescence from the tissue. Also as shown, the indicator 298 is exposed fully but may be partially covered by the jacket 306. In some configurations, the jacket 306 may be omitted.

With reference to FIG. 22, a different configuration of a suction tube 156' is shown. Specifically, the suction tube 156' does not include a through bore in a handle 159' of the suction tube 156'. Instead, the sample element 164''' is coupled to the suction tool 156' via fixation elements 308. Specifically, the sample element 164''' is shown coupled to the suction cannula 157' by two fixation elements. Although only two fixation elements 308 are illustrated, more than two fixation elements 308 may be used to couple the sample element 164 to the suction cannula 157' or the handle 159'. The fixation elements 308 may include a clip, a band, or anything that may secure the sample element 164 to the suction tool 156'.

Clauses

Clause 1—An ultrasonic surgical system comprising: an ultrasonic handpiece assembly configured to remove brain tissue, the ultrasonic handpiece assembly; a sample element coupled to the ultrasonic handpiece assembly and including at least one fiber configured to collect a fluorescent light emitted from the brain tissue; an indicator coupled to the ultrasonic handpiece assembly configured to selectively emit light; a controller configured to: detect a type of brain tissue based on the fluorescent light; activate the indicator based on the detected type of brain tissue; and control the ultrasonic handpiece assembly based on the detected type of brain tissue.

Clause 2—The ultrasonic surgical system of clause 1, wherein the at least one fiber is coupled to an excitation source, the at least one fiber configured to illuminate an excitation light from the excitation source to induce the fluorescent light and collect the fluorescent light emitted from the brain tissue.

Clause 3—The ultrasonic surgical system of clause 2, further comprising an optical system coupled to the controller and the sample element, the optical system including the excitation source and an optical detection system configured to convert the fluorescent light into an electrical signal wherein the controller detects the type of brain tissue from the electrical signal.

Clause 4—The ultrasonic surgical system of clause 3, wherein: the excitation source is further defined as a first excitation source, the fluorescent light is further defined as a first fluorescent light, and the electrical signal is further defined as a first electrical signal; the optical system further including a second excitation source; the at least one fiber configured to illuminate a second excitation light from the second excitation source to induce a second fluorescent light emitted from the brain tissue and collect the second fluorescent light; the optical detection system configured to convert the second fluorescent light into a second electrical signal; and the controller configured to determine a second type of brain tissue from the second electrical signal.

Clause 5—The ultrasonic surgical system of clause 3, wherein the controller is configured to detect the type of brain tissue based on an algorithm.

Clause 6—The ultrasonic surgical system of clause 5, wherein the algorithm includes a calibration routine to be performed with respect to healthy tissue or a baseline parameter.

Clause 7—The ultrasonic surgical system of clause 5, wherein the algorithm is configured to calculate a modified electrical signal by fitting a baseline polynomial curve to the electrical signal and subtract the baseline polynomial curve from the electrical signal to remove ambient light.

Clause 8—The ultrasonic surgical system of clause 7, wherein the algorithm includes fitting at least one gaussian distribution to the modified electrical signal.

Clause 9—The ultrasonic surgical system of clause 5, wherein: the controller is configured to cycle the excitation source on and off; the sample element is configured to collect ambient light when the excitation source is off and not illuminating the brain tissue with the fluorescent light; the sample element configured to collect ambient light and the fluorescent light when the excitation source is on and the sample element is illuminating the brain tissue with the fluorescent light; and wherein the algorithm includes subtracting the ambient light from the fluorescent light.

Clause 10—The ultrasonic surgical system of clause 1, wherein the ultrasonic handpiece assembly includes an ultrasonic handpiece and a sleeve, the indicator being coupled to the sleeve.

Clause 11—The ultrasonic surgical system of clause 1, further comprising an electrode configured to apply electrical stimulation to the brain tissue wherein the controller generates an alert when the electrical stimulation produces a predefined response from a patient.

Clause 12—A surgical system comprising: surgical tool configured to remove brain tissue; a sample element coupled to the surgical tool and including at least one fiber configured to collect (i) a fluorescent light emitted from the brain tissue; an indicator coupled to the surgical tool and configured to selectively emit light; a controller configured to: detect a type of brain tissue based on the fluorescent light;

activate the indicator based on the detected type of brain tissue; and control the surgical tool based on the detected type of brain tissue.

Clause 13—The surgical system of clause 12 further comprising an optical system coupled to the controller and the sample element, the optical system including: an excitation source coupled to the at least one fiber, the at least one fiber configured to illuminate the brain tissue with an excitation light from the excitation source to induce the fluorescent light and collect the fluorescent light emitted from the brain tissue; and an optical detection system configured to convert the fluorescent light into an electrical signal wherein the controller detects the type of brain tissue from the electrical signal.

Clause 14—The surgical system of clause 13, wherein: the excitation source is further defined as a first excitation source, the fluorescent light is further defined as a first fluorescent light, and the electrical signal is further defined as a first electrical signal; the optical system further including a second excitation source; the at least one fiber configured to illuminate a second excitation light from the second excitation source to induce a second fluorescent light emitted from the brain tissue and collect the second fluorescent light; the optical detection system configured to convert the second fluorescent light into a second electrical signal; and the controller configured to determine a second type of brain tissue from the second electrical signal.

Clause 15—The surgical system of clause 13, wherein the controller is configured to detect the type of brain tissue based on an algorithm.

Clause 16—The surgical system of clause 15, wherein the algorithm includes a calibration routine to be performed with respect to healthy tissue or a baseline parameter.

Clause 17—The surgical system of clause 15, wherein the algorithm is configured to calculate a modified electrical signal by fitting a baseline polynomial curve to the electrical signal and subtract the baseline polynomial curve from the electrical signal to remove ambient light.

Clause 18—The surgical system of clause 17, wherein the algorithm includes fitting at least one gaussian distribution to the modified electrical signal.

Clause 19—The surgical system of clause 15, wherein the controller is configured to cycle the excitation source on and off; the sample element is configured to collect ambient light when the excitation source is off and not illuminating the brain tissue with the fluorescent light;

the sample element is configured to collect ambient light and the fluorescent light when the excitation source is on and the sample element is illuminating the brain tissue with the fluorescent light; and wherein the algorithm includes subtracting the ambient light from the fluorescent light.

Clause 20—The surgical system of clause 12, wherein the surgical tool comprises bipolar forceps.

Clause 21—The surgical system of clause 12, wherein the surgical tool comprises a neuro stimulator.

Clause 22—The surgical system of clause 12, wherein the surgical tool comprises a neuro dissector.

Clause 23—The surgical system of clause 12, wherein the surgical tool comprises an ablation device.

Clause 24—The surgical system of clause 12, wherein the controller is configured to control the surgical tool by adjusting an operating parameter of the surgical tool based on the detection of the type of brain tissue.

Clause 25—The surgical system of clause 12, further comprising an electrode configured to apply electrical stimulation to the brain tissue.

Clause 26—The surgical system of clause 25, wherein the controller generates an alert when the electrical stimulation produces a predefined response from a patient.

Clause 27—A surgical suction system comprising: suction tool configured to apply suction to brain tissue; a sample element coupled to the suction tool including at least one optical fiber configured to collect a fluorescent light emitted from the brain tissue; an indicator coupled to the suction tool and configured to selectively emit light; a controller configured to: detect a type of brain tissue based on the fluorescent light; and activate the indicator on the detected type of brain tissue.

Clause 28—The surgical suction system of clause 27, wherein the at least one optical fiber is coupled to an excitation source, the at least one fiber configured to illuminate an excitation light from the excitation source to induce the fluorescent light and collect the fluorescent light emitted from the brain tissue.

Clause 29—The surgical suction system of clause 28, further comprising an optical system coupled to the controller and the sample element, the optical system including the excitation source and an optical detection system configured to convert the fluorescent light into a electrical signal wherein the controller detects the type of brain tissue from the electrical signal.

Clause 30—The surgical suction system of clause 29, wherein: the excitation source is further defined as a first excitation source, the fluorescent light is further defined as a first fluorescent light, and the electrical signal is further defined as a first electrical signal: the optical system further including a second excitation source; the at least one fiber configured to illuminate a second excitation light from the second excitation source to induce a second fluorescent light emitted from the brain tissue and collect the second fluorescent light; the optical detection system configured to convert the second fluorescent light into a second electrical signal; and the controller configured to determine a second type of brain tissue from the second electrical signal.

Clause 31—The surgical suction system of clause 29, wherein the controller is configured to detect the type of brain tissue based on an algorithm.

Clause 32—The surgical suction system of clause 31, wherein the algorithm includes a calibration routine to be performed with respect to healthy tissue or a baseline parameter.

Clause 33—The surgical suction system of clause 31, wherein the algorithm is configured to calculate a modified electrical signal by fitting a baseline polynomial curve to the electrical signal and subtract the baseline polynomial curve from the electrical signal to remove ambient light.

Clause 34—The surgical suction system of clause 33, wherein the algorithm includes fitting at least one gaussian distribution to the modified electrical signal.

Clause 35—The surgical suction system of clause 31, wherein: the controller is configured to cycle the excitation source on and off; the sample element is configured to collect ambient light when the excitation source is off and not illuminating the brain tissue with the fluorescent light; the sample element is configured to collect ambient light and the fluorescent light when the excitation source is on and the sample element is illuminating the brain tissue with the fluorescent light; and wherein the algorithm includes subtracting the ambient light from the fluorescent light.

Clause 36—The surgical suction system of clause 27, further comprising an electrode configured to apply electrical stimulation to the brain tissue, wherein the controller generates an alert when the electrical stimulation produces a predefined response from a patient.

Clause 37—The surgical suction system of clause 27, the suction tool including a handle portion and an elongated portion, the sample element being coupled to the elongated portion.

Clause 38—A method for detecting target tissue under ambient light conditions in an operating room, the method comprising: positioning, an optical fiber, in a sterile field that includes brain tissue being illuminated by ambient light; collecting, with the optical fiber, fluorescent light emitted from the brain tissue; detecting, with a controller coupled to the optical fiber, target tissue of the brain tissue based on fluorescent light emitted from the brain tissue; and activating an indicator positioned within the sterile field to produce a visual alert in response to the detection of the target tissue.

Clause 39—The method of clause 38, wherein the fluorescent light is emitted from the brain tissue in response to illuminating the brain tissue with excitation light from an excitation source coupled to the optical fiber.

Clause 40—The method of clause 39, wherein the detecting the fluorescent light emitted from the target tissue during the surgical procedure is based on an algorithm.

Clause 41—The method of clause 40, wherein the algorithm includes a calibration routine to be performed with respect to healthy tissue or a baseline parameter.

Clause 42—The method of clause 40, further comprising an optical system coupled to the optical fiber and the controller, the optical system configured to convert the fluorescent light collected from the target tissue into an electrical fluorescent signal.

Clause 43—The method of clause 42, wherein the optical system includes a spectrometer.

Clause 44—The method of clause 42, wherein the algorithm includes calculating a modified electrical fluorescent signal by fitting a baseline polynomial curve to the electrical fluorescent signal and subtracting the baseline polynomial curve from an electrical fluorescent signal to remove the ambient light.

Clause 45—The method of clause 44, wherein the algorithm includes fitting at least one gaussian distribution to the modified electrical fluorescent signal.

Clause 56—The method of clause 40, further comprising: cycling the excitation light from an excitation source on and off; collecting ambient light, with the optical fiber, when the excitation light is off and the brain tissue is not illuminated by the excitation light; and wherein the algorithm includes subtracting the ambient light from the fluorescent light.

Clause 47—The method of clause 38, wherein the optical fiber is integrated into at least one of a surgical tool and a standalone device.

Clause 48—The method of clause 38, wherein the indicator comprises a light emitting device coupled to a surgical instrument.

Clause 49—A method for detecting target tissue under ambient light conditions in an operating room using a surgical system, the surgical system comprising a working tool including at least one optical fiber, an indicator an optical system coupled to the working tool, and an excitation source coupled to the at least one optical fiber, the method for detecting target tissue comprising: positioning the working tool in a sterile field that includes brain tissue illuminated by ambient light; detecting, with the optical system, fluorescence light emitted from the target tissue during a surgical procedure with the least one optical fiber of the working tool, wherein detecting the fluorescence light includes: illuminating tissue with blue light from the excitation source with the at least one optical fiber; collecting, with the at least one optical fiber, the ambient light and the fluorescence light; generating a fluorescence signal based on the fluorescence light emitted from the target tissue with the ambient light removed; determining that the target tissue is present based on the detected fluorescence light; and activating the indicator of the working tool in response to detection of the target tissue.

Clause 50—The method for detecting target tissue of clause 49, wherein: illuminating tissue with blue light from the excitation source with the at least one optical fiber is performed over a first period of time and illuminating tissue with blue light is not performed over a second period of time; collecting the ambient light and the fluorescence light is performed over the first period of time; detecting the fluorescence light further includes: collecting, with the at least one optical fiber, the ambient light over a second period of time; generating (i) a first signal based on the ambient light and the fluorescence light collected during the first period of time, (ii) a second signal based on the ambient light collected during the second period of time; and the ambient light is removed from the fluorescence signal using an algorithm based on the first signal and the second signal.

Clause 51—The method for detecting target tissue of clause 50, wherein the algorithm includes calculating a baseline curve using a least-squares polynomial based on the difference of the first signal and the second signal.

Clause 52—The method for detecting target tissue of clause 51, wherein the algorithm includes subtracting the baseline curve from the difference of the first signal and the second signal to obtain the fluorescence signal.

Clause 53—The method for detecting target tissue of clause 52, wherein the algorithm includes calculating at least one gaussian curve for at least one spectral band of the fluorescence signal.

Clause 54—The method for detecting target tissue of clause 49, wherein the working tool is a suction handle.

Clause 55—The method for detecting target tissue of clause 49, wherein the working tool is an ablation device.

Clause 56—The method for detecting target tissue of clause 55, further comprising removing, with the working tool, the target tissue based on the indicator.

Clause 57—The method for detecting target tissue of clause 49, wherein the ambient light includes light generated by a surgical microscope and light generated by one or more surgical lamps.

Clause 58—The method for detecting target tissue of clause 49, the surgical system including a display, the method further comprising displaying the fluorescence signal at the display.

Clause 59—The method for detecting target tissue of clause 49, wherein the working tool includes at least one electrode configured to apply a stimulating current to target tissue, the method for detecting target tissue further comprising:

applying electrical stimulation to the target tissue; and
determining whether the electrical stimulation of the target tissue affects a patient.

Clause 60—The method for detecting target tissue of clause 59, wherein in response to the determination that the electrical stimulation affects the patient, controlling operation of the working tool in order to prevent the working tool from operating on the target tissue.

Clause 61—The method for detecting target tissue of clause 60, wherein controlling operation of the working tool includes changing an operation parameter of the working tool.

Clause 62—The method for detecting target tissue of clause 61, wherein the operation parameter includes at least one of an applied voltage, a current drawn, and power consumption.

Clause 63—The method for detecting target tissue of clause 59, wherein the indicator is further defined as a first indicator, the working tool includes a second indicator, the method for detecting target tissue further comprising activating the second indicator in response to the determination that the electrical stimulation affects the patient.

Clause 64—The method for detecting target tissue of clause 49, wherein the target tissue is further defined as a first target tissue, the method further comprising detecting, with the optical system, a second target tissue based on a second fluorescence light emitted from the second target tissue.

Clause 65—The method for detecting target tissue of clause 64, further comprising in response to detecting the second target tissue, controlling operation of the working tool in order to prevent the working tool from operating on the second target tissue.

Clause 66—The method for detecting target tissue of clause 64, wherein the second target tissue corresponds to a blood vessel.

Clause 67—The method for detecting target tissue of clause 49, wherein detecting the fluorescence light is performed in less than one second.

Clause 68—A method for detecting and removing target tissue under ambient light conditions in an operating room using a surgical system, the surgical system comprising a first working tool, a second working tool, an attachment including at least one optical fiber, an indicator, an optical system, and an excitation source coupled to the at least one optical fiber, the method for detecting target tissue comprising: coupling the attachment to at least one of the first working tool and the second working tool; detecting, with the optical system, a target tissue during a surgical procedure based on fluorescence light emitted from the target tissue; activating the indicator of the attachment, while at least one of the first working tool and the second working tool is in a sterile field, in response to detection of the target tissue; viewing the indicator of the attachment while at least one of the first working tool and at least one of the second working tool is within the sterile field; performing a first surgical operation at a surgical site while the first working tool is in a first hand of the operator; and performing a second surgical operation at the surgical site while the second working tool is in a second hand of the operator in response to the indicator while maintaining the first working tool in the first hand.

Clause 69—The method for detecting and removing target tissue of clause 68, wherein the first working tool corresponds to a suction cannula, the first surgical operation includes suctioning fluid from the surgical site.

Clause 70—The method for detecting and removing target tissue of clause 68, wherein the second working tool corresponds to bipolar forceps.

Clause 71—A method for detecting and removing target tissue under ambient or microscope light conditions in an operating room using a surgical system, the surgical system comprising a suction cannula including at least one optical fiber, an indicator, a working tool, an optical system, and an excitation source coupled to the at least one optical fiber, comprising: positioning the working tool and the suction cannula in a sterile field that includes brain tissue illuminated by ambient light; detecting, with the optical system, a target tissue during a surgical procedure based on fluorescence light emitted from the target tissue; activating the indicator of the suction cannula, while the suction cannula is in a sterile field, in response to detection of the target tissue; viewing the indicator of the suction cannula while the suction cannula is within the sterile field; suctioning fluid from a surgical site with the suction cannula while the suction cannula is in a first hand of an operator; and operating on the target tissue, with the working tool in a second hand of the operator, in response to the indicator while maintaining the suction cannula in the first hand of the operator.

Clause 72—A method for detecting target tissue under ambient light conditions in an operating room using a surgical system, the surgical system comprising a working tool including at least one optical fiber, an indicator, an optical system coupled to the working tool, and an excitation source coupled to the at least one optical fiber, the method for detecting target tissue comprising: detecting, with the optical system, fluorescence light emitted from the target tissue during a surgical procedure with the least one optical fiber of the working tool, wherein detecting the fluorescence light includes: illuminating tissue with blue light from the excitation source with the at least one optical fiber; collecting, with the at least one optical fiber, the ambient light and the fluorescence light; generating a fluorescence signal based on the fluorescence light emitted from the target tissue with the ambient light removed; determining that the target tissue is present based on the detected fluorescence light; and activating the indicator of the working tool in response to detection of the target tissue.

Clause 73—An optical probe system for determining whether brain tissue of a patient is tumorous. The optical probe system including a sample element including an optical fiber configured to transmit a fluorescence emitted by the brain tissue and an indicator configured to selectively emit visible light, the visible light being different from the fluorescence transmitted by the optical fiber. The optical probe system including an excitation source configured to emit an excitation light, the excitation light having a wavelength to induce the fluorescence in the tumorous tissue. The optical probe system including an optical instrument coupled to the optical fiber, the optical instrument configured to convert the fluorescence emitted by the brain tissue and transmitted by the optical fiber into an electrical signal; and a controller coupled to the indicator and the optical instrument, the controller configured to: determine that the brain tissue is tumorous based on the electrical signal; and activate the indicator based on the determination that the brain tissue is tumorous.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the examples is described above as having certain features, any one or more of those features described with respect to any example of the disclosure can be implemented in and/or combined with features of any of the other examples, even if that combination is not explicitly described. In other words, the described examples are not mutually exclusive, and permutations of one or more examples with one another remain within the scope of this disclosure.

Spatial and functional relationships between elements (for example, between controllers, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

As used herein, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "controller" or "module" may be replaced with the term "circuit." The term "controller" may refer to, be part of, or include: an Application Specific Integrated Circuit (ASIC); a programmable system on a chip (PSoC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller may include one or more interface circuits with one or more transceivers. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The controller may communicate with other controllers using the interface circuit(s). Although the controller may be depicted in the present disclosure as logically communicating directly with other controllers, in various implementations the controller may actually communicate via a communications system. The communications system may include physical and/or virtual networking equipment such as hubs, switches, routers, gateways and transceivers. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the controller may be distributed among multiple controllers that are connected via the communications system. For example, multiple controllers may implement the same functionality distributed by a load balancing system. In a further example, the functionality of the controller may be split between a server (also known as remote, or cloud) controller and a client (or, user) controller.

Some or all hardware features of a controller may be defined using a language for hardware description, such as IEEE Standard 1364-2005 (commonly called "Verilog") and IEEE Standard 1076-2008 (commonly called "VHDL"). The hardware description language may be used to manufacture and/or program a hardware circuit. In some implementations, some or all features of a controller may be defined by a language, such as IEEE 1666-2005 (commonly called "SystemC"), that encompasses both code, as described below, and hardware description.

The term code, as used above, may include software, firmware, and/or microcode, and may refer to programs, routines, functions, classes, data structures, and/or objects. The term shared processor circuit encompasses a single processor circuit that executes some or all code from multiple controllers. The term group processor circuit encompasses a processor circuit that, in combination with additional processor circuits, executes some or all code from one or more controllers. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple controllers. The term group memory circuit encompasses a memory circuit that, in combination with additional memories, stores some or all code from one or more controllers.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above may serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A neurosurgery system for probing brain tissue of a patient for tumorous tissue, the neurosurgery system comprising:

a suction tool configured to apply suction to tissue of the patient, the suction tool including:

a suction cannula defining a lumen;

an optical fiber, coupled to the suction cannula, the optical fiber being configured to transmit a fluorescence emitted by the brain tissue; and an indicator coupled to the suction cannula and configured to selectively emit visible light, the visible light being different from the fluorescence transmitted by the optical fiber;

an excitation source configured to emit an excitation light, the excitation light having a wavelength to induce the fluorescence in the tumorous tissue;

an optical instrument coupled to the optical fiber, the optical instrument configured to convert the fluorescence emitted by the brain tissue and transmitted by the optical fiber into an electrical signal; and a controller coupled to the optical instrument, the controller configured to:

fit a baseline polynomial curve to the electrical signal;

calculate a modified electrical signal by subtracting the baseline polynomial curve from the electrical signal to remove ambient light;

fit at least one gaussian band to the modified electrical signal;

perform an error correction process by determining a ratio of the modified electrical signal to the at least one gaussian band that has been fitted to the modified electrical signal;

determine that the brain tissue is tumorous based on the modified electrical signal and the ratio; and activate the indicator based on the determination that the brain tissue is tumorous.

2. The neurosurgery system of claim 1, wherein:

the suction tool includes a handle coupled to the suction cannula; and wherein the handle defines a connector to receive a suction tube.

3. The neurosurgery system of claim 1, wherein the optical fiber includes a distal end, the distal end of the optical fiber positioned distal of the indicator.

4. The neurosurgery system of claim 3, wherein the suction cannula includes a distal end, the distal end of the optical fiber positioned proximally the distal end of the suction cannula.

5. The neurosurgery system of claim 1, wherein the indicator is coupled to a light source.

6. The neurosurgery system of claim 5, wherein the light source of the indicator is configured to emit a first color, the first color being a different color than a color emitted by the excitation source.

7. The neurosurgery system of claim 1, wherein the suction tool includes a handle that defines a control portion including an input control for controlling operation of the suction tool.

8. The neurosurgery system of claim 7, the neurosurgery system further comprising a jacket that surrounds a portion of the suction cannula and a portion of the optical fiber, wherein the suction cannula includes a distal end and the optical fiber includes a distal end, the distal end of the optical fiber and the distal end of the suction cannula being exposed.

9. The neurosurgery system of claim 8, the control portion defining a through bore for receiving the optical fiber and the indicator.

10. The neurosurgery system of claim 9, wherein the jacket is positioned to cover at least a portion of the through bore.

11. The neurosurgery system of claim 7, wherein the suctional suction cannula includes a proximal end and a distal end, the handle includes a proximal end and a distal end, the proximal end of the suction cannula is coupled to the distal end of the handle and the distal end of the suction cannula is configured to contact the patient.

12. The neurosurgery system of claim 1, wherein the controller is configured to compare the ratio to a threshold and determine whether the brain tissue is tumorous based on the comparison.

13. The neurosurgery system of claim 1, wherein the controller is configured to:
during a first period of time:
instruct a healthcare professional to collect light from a light source, the light source outputting the light from a consistent spectral band over time;
receive a second electrical signal from the optical instrument, the second electrical signal representing the light emitted from the light source during the first period of time; and
store the second electrical signal;
during a second period of time occurring after the first period of time:
instruct the healthcare professional to collect light from the light source;
receive a third electrical signal from the optical instrument, the third electrical signal representing the light emitted from the light source during the second period of time; and
store the third electrical signal;
determine a variation of the optical instrument over time based on a comparison of the second electrical signal to the third electrical signal; and
adjust one or more parameters of an algorithm used to determine that the brain tissue is tumorous based on the variation.

14. A neurosurgery system for probing brain tissue of a patient for tumorous tissue, the neurosurgery system comprising:
a suction tool configured to apply suction to tissue of the patient, the suction tool including:
a suction cannula defining a lumen;
an optical fiber, coupled to the suction cannula, the optical fiber being configured to transmit a fluorescence emitted by the brain tissue; and
an indicator coupled to the suction cannula and configured to selectively emit visible light, the visible light being different from the fluorescence transmitted by the optical fiber;
an excitation source configured to emit an excitation light, the excitation light having a wavelength to induce the fluorescence in the tumorous tissue;
an optical instrument coupled to the optical fiber, the optical instrument configured to convert the fluorescence emitted by the brain tissue and transmitted by the optical fiber into a first electrical signal; and
a controller coupled to the optical instrument, the controller configured to:
during a first period of time:
instruct a healthcare professional to collect light from a light source, the light source outputting the light from a consistent spectral band over time;
receive a second electrical signal from the optical instrument, the second electrical signal representing the light emitted from the light source during the first period of time; and
store the second electrical signal;
during a second period of time occurring after the first period of time:
instruct the healthcare professional to collect light from the light source;
receive a third electrical signal from the optical instrument, the third electrical signal representing the light emitted from the light source during the second period of time; and
store the third electrical signal;
determine a variation of the optical instrument over time based on a comparison of the second electrical signal to the third electrical signal; and
adjust one or more parameters of an algorithm used to determine that the brain tissue is tumorous based on the variation;
determine that the brain tissue is tumorous based on the first electrical signal and the adjusted algorithm; and
activate the indicator based on the determination that the brain tissue is tumorous.

15. The neurosurgery system of claim 14, wherein:
the suction tool includes a handle coupled to the suction cannula; and
wherein the handle defines a connector to receive a suction tube.

16. The neurosurgery system of claim 14, wherein the optical fiber includes a distal end, the distal end of the optical fiber positioned distal of the indicator.

17. The neurosurgery system of claim 16, wherein the suction cannula includes a distal end, the distal end of the optical fiber positioned proximally the distal end of the suction cannula.

18. The neurosurgery system of claim 14, wherein:
the indicator is coupled to a light source; and
the light source of the indicator is configured to emit a first color, the first color being a different color than a color emitted by the excitation source.

19. The neurosurgery system of claim 14, wherein the suction tool includes a handle that defines a control portion including an input control for controlling operation of the suction tool.

20. The neurosurgery system of claim 19, the neurosurgery system further comprising a jacket that surrounds a portion of the suction cannula and a portion of the optical fiber, wherein the suction cannula includes a distal end and the optical fiber includes a distal end, the distal end of the optical fiber and the distal end of the suction cannula being exposed.

21. A neurosurgery system for probing brain tissue of a patient for tumorous tissue, the neurosurgery system comprising:
  a suction tool configured to apply suction to tissue of the patient, the suction tool including:
    a suction cannula defining a lumen;
    an optical fiber, coupled to the suction cannula, the optical fiber being configured to transmit a fluorescence emitted by the brain tissue; and
    an indicator coupled to the suction cannula and configured to selectively emit visible light, the visible light being different from the fluorescence transmitted by the optical fiber;
  an excitation source configured to emit an excitation light, the excitation light having a wavelength to induce the fluorescence in the tumorous tissue;
  an optical instrument coupled to the optical fiber, the optical instrument configured to convert the fluorescence emitted by the brain tissue and transmitted by the optical fiber into an excited spectral signal; and
  a controller coupled to the optical instrument, the controller configured to:
    fit a first gaussian band to an ambient electrical signal;
    fit a second gaussian band to the excited spectral signal;
    perform an error correction process by determining a ratio of the second gaussian band to the first gaussian band;
    determine that the brain tissue is tumorous based on the excited spectral signal and the ratio; and
    activate the indicator based on the determination that the brain tissue is tumorous.

22. The neurosurgery system of claim 21, wherein the controller is configured to:

determine a ratio of a width of the second gaussian band to a width of the first gaussian band; and
compare the ratio to a threshold and determine whether the brain tissue is tumorous based on the comparison.

23. A neurosurgical method for detecting whether brain tissue of a patient includes tumorous tissue under ambient light conditions in an operating room using a surgical system, the surgical system comprising an excitation source, an optical instrument, a controller coupled to the optical instrument, and a suction tool configured to apply suction to tissue of the patient and including a suction cannula defining a lumen, an optical fiber coupled to the suction cannula and the optical instrument, and an indicator coupled to the suction cannula and configured to selectively emit visible light that is different from a fluorescence transmitted by the optical fiber, the method comprising:
  emitting, from the excitation source, an excitation light having a wavelength to induce the fluorescence in the tumorous tissue;
  transmitting, with the optical fiber, the fluorescence emitted by the brain tissue in response to the excitation light;
  converting, with the optical instrument, the fluorescence emitted by the brain tissue and transmitted by the optical fiber into an electrical signal;
  fitting, with the controller, a baseline polynomial curve to the electrical signal;
  calculating, with the controller, a modified electrical signal by subtracting the baseline polynomial curve from the electrical signal to remove ambient light;
  fitting, with the controller, at least one gaussian band to the modified electrical signal;
  performing, with the controller, an error correction process by determining a ratio of the modified electrical signal to the at least one gaussian band that has been fitted to the modified electrical signal;
  determining, with the controller, that the brain tissue is tumorous based on the modified electrical signal and the ratio; and
  activating, with the controller, the indicator based on the determination that the brain tissue is tumorous.

\* \* \* \* \*